(12) United States Patent
Donde et al.

(10) Patent No.: US 7,091,231 B2
(45) Date of Patent: Aug. 15, 2006

(54) 12-ARYL PROSTAGLANDIN ANALOGS

(75) Inventors: Yariv Donde, Dana Point, CA (US); Jeremiah H. Nguyen, La Puente, CA (US)

(73) Assignee: Allergan, Inc., Irvine, CA (US)

( * ) Notice: Subject to any disclaimer, the term of this patent is extended or adjusted under 35 U.S.C. 154(b) by 31 days.

(21) Appl. No.: 11/009,298

(22) Filed: Dec. 10, 2004

(65) Prior Publication Data

US 2006/0148894 A1    Jul. 6, 2006

(51) Int. Cl.
*A61K 31/24* (2006.01)
*A61K 31/41* (2006.01)
*A61K 31/165* (2006.01)
*A61K 31/192* (2006.01)
*A61K 31/221* (2006.01)
*A61K 31/222* (2006.01)

(52) U.S. Cl. .................. 514/381; 514/507; 514/513; 514/563; 514/570; 548/250; 560/121; 562/503; 564/161; 564/170; 564/189

(58) Field of Classification Search ............... 514/381, 514/507, 513, 563, 570; 560/121; 548/250; 562/503; 564/161, 170, 189
See application file for complete search history.

(56) References Cited

U.S. PATENT DOCUMENTS

| | | | | |
|---|---|---|---|---|
| 4,166,452 | A | 9/1979 | Generales, Jr. | 128/741 |
| 4,256,108 | A | 3/1981 | Theeuwes | 128/260 |
| 4,265,874 | A | 5/1981 | Bonsen et al. | 424/15 |
| 5,462,968 | A | 10/1995 | Woodward | 514/568 |
| 5,698,598 | A | 12/1997 | Woodward | 514/530 |
| 6,090,847 | A | 7/2000 | Woodward | 514/530 |
| 6,437,146 | B1 | 8/2002 | Hattori et al. | 548/236 |
| 6,710,072 | B1 | 3/2004 | Burk et al. | 514/438 |
| 6,747,037 | B1 | 6/2004 | Old et al. | 514/277 |

FOREIGN PATENT DOCUMENTS

WO    2005/061449 A1    7/2005

OTHER PUBLICATIONS

Dragoli, D., et al., "Parallel Synthesis of Prostaglandin E1 Analogues", J. Comb. Chem. 1999. pp. 534-539.*
Francis A. Carey, Organic Chemistry, New York: McGraw-Hill Book Company 1987, p. 63.
Remington's Pharmaceutical Sciences, Mack Publishing Company, Easton, Pa., 16th Edition, 1980.

* cited by examiner

*Primary Examiner*—Kamal A. Saeed
*Assistant Examiner*—Michael P. Barker
(74) *Attorney, Agent, or Firm*—Brent A. Johnson; Robert J. Baran; Martin A. Voet

(57) ABSTRACT

Compounds comprising

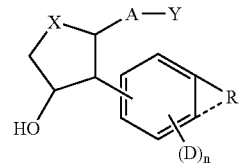

are disclosed, wherein Y, A, X, R, D, and n are as described.

Figure 1:
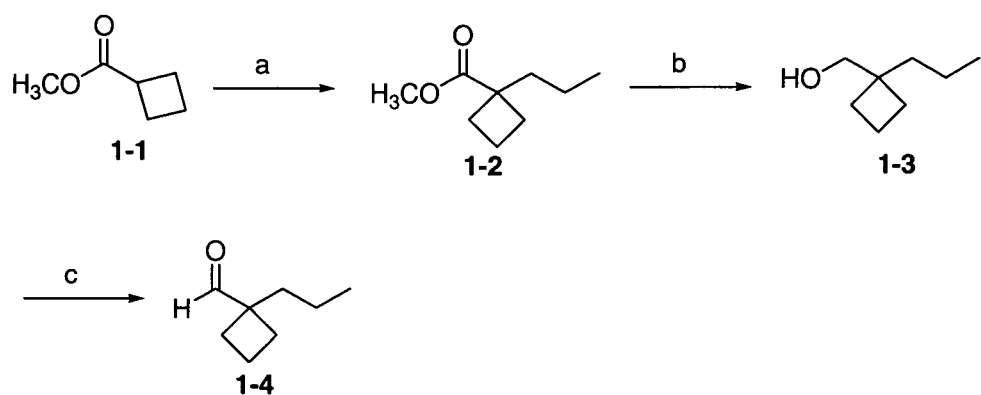

A compound comprising a prostaglandin $EP_2$ selective agonist wherein the ω-chain comprises a substituted phenyl, wherein at least one substituent consists of hydrocarbyl or non-linear hydroxyhydrocarbyl is also disclosed herein.

Methods, compositions, and medicaments related thereto are also disclosed.

46 Claims, 17 Drawing Sheets

(a) LDA; propyl iodide; (b) LiBH$_4$; (c) TPAP, NMO, 4Å sieves.

(a) LiBH₄; (b)TBSOTf, 2,6-lutidine.

(a) *n*-BuLi; cyclobutanone; (b)TBSOTf, 2,6-lutidine.

(a) *n*-BuLi; RCHO; (b)TBSOTf, 2,6-lutidine.

(a) t-BuLi; (b) lithium 2-thienylcuprate; (c) 5-2, THF -78 °C; (d) HF-pyridine, 0 °C; (e) rabbit liver esterase; (f) H₂, Pd/C.

(a) HOAc/H₂O/THF.

eq. 1

(a) EtOCOCl, TEA;RNH₂ or N-hydroxysuccinimide, EDCI, RNH₂, DMF.

eq. 2

(a) L-Selectride; (b) MsCl, TEA; (c) (n-Bu)$_4$NCl 40 °C; (d) HF-pyridine, 0 °C; (e) LiOH, H$_2$O, THF (f) i-PrI, DBU; (g) H$_2$, Pd/C.

(a) NaH; MPMCl; (b) *t*-BuLi; (c) lithium 2-thienylcuprate; (d) DDQ; (e) HF-pyridine 0 °C;
(f) Rabbit Liver Esterase; (g) H₂, Pd/C, EtOAc; (h) Wilkinson's catalyst, H₂, THF.

(a) L-selectride; H$_2$O$_2$; (b) MsCl, Et$_3$N; (c) (n-Bu)$_4$NCl 40 °C; (d) DDQ; (e) 1 M LiOH; (f) H$_2$, Pd/C, ethyl acetate.

(a) DDQ; (b) TPAP, NMO; (c) i-PrMgCl or t-BuMgBr; (d) HF-pyridine 0 °C; (e) 1 M LiOH;
(f) $H_2$, Pd/C, ethyl acetate.

(a) *t*-BuLi; (b) Me$_2$Zn; (c) L-selectride; H$_2$O$_2$; (d) MsCl, TEA; (e) *n*-Bu$_4$NCl (f) HF-pyridine, 0 °C; (g) Rabbit Liver Esterase.

(a) $H_2$, $NiCl_2$, $NaBH_4$, $H_2NCH_2CH_2NH_2$; (b) rabbit liver esterase; (c) $H_2$, Pd/C.

a) $K_2CO_3$, methyl bromoacetate; (b) $Ph_3P$, $I_2$, imidazole, $CH_2Cl_2$.

a) *t*-BuLi; (b)Me₂Zn; (c) HF-pyridine, 0 °C; (d) rabbit liver esterase.

(a) L-Selectride; (b) MsCl, TEA; (n-Bu)₄NCl; (c) HF-pyridine, 0 °C; (d) LiOH, H₂O, THF.

(a) NaBH$_4$; (b) MPMCl, NaH; (c) t-BuLi; (d) 2-thienylCuCNLi; (e) HOAc/H$_2$O/THF;
(f) DDQ; (g) rabbit lever esterase; (h) H$_2$, Pd/C.

(a) L-selectride; $H_2O_2$; (b) MsCl, TEA;(c)TBAC 40 °C; (d) HOAc/$H_2O$/THF;
(e) DDQ; (f) rabbit liver esterase; (g) i-PrI, DBU (h) $H_2$, Pd/C.

(a) DAST, $CH_2Cl_2$ -78 °C; (b) 1 M LiOH, THF.

12-ARYL PROSTAGLANDIN ANALOGS

FIELD OF THE INVENTION

This invention relates to compounds which are useful for treatment of diseases. In particular, the compounds related to the invention are useful for the treatment of diseases or conditions related to prostaglandins or to the activity of prostaglandin receptors.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

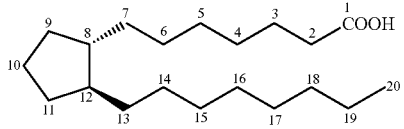

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; U.S. Pat. No. 5,698,598; and U.S. Pat. No. 6,090,847.

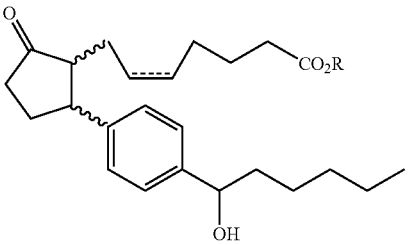

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, post-menopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

BRIEF DESCRIPTION OF THE INVENTION

Disclosed herein are compounds comprising

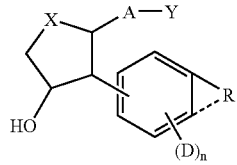

or a pharmaceutically acceptable salt or a prodrug thereof, wherein a dashed line represents the presence or absence of a covalent bond;

Y is a carboxylic acid, sulfonic acid, or phosphonic acid; or an amide or ester thereof comprising from 0 to 12 carbon atoms; or Y is a hydroxymethyl, or tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is substituted or unsubstituted phenyl or monocyclic heteroaryl, the sum of m and o is from 1 to 4, and wherein one $CH_2$ may be substituted with S or O;

X is C=O, CHF, $CF_2$, CHCl, or CHOH; wherein if X is CHOH, then OH is in the β-configuration;

R is a hydrocarbyl or a hydroxyhydrocarbyl moiety comprising from 1 to 12 carbon atoms;

D is independently a moiety comprising from 1 to 6 non-hydrogen atoms; and n is an integer from 0 to 4.

A compound comprising a prostaglandin $EP_2$ selective agonist wherein the ω-chain comprises a substituted phenyl, wherein at least one substituent consists of hydrocarbyl or non-linear hydroxyhydrocarbyl, is also disclosed herein.

Methods, compositions, and medicaments related thereto are also disclosed.

BRIEF DESCRIPTION OF THE DRAWING FIGURES

Figure 2:
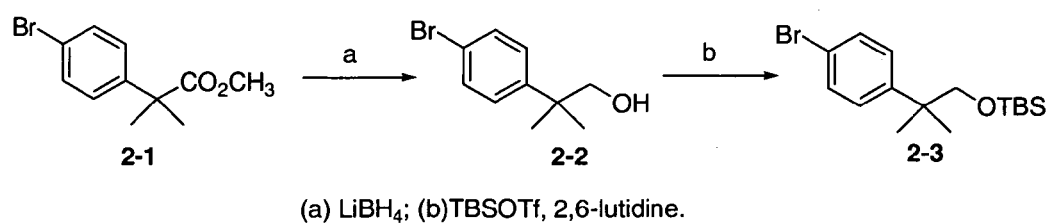
Figure 3:
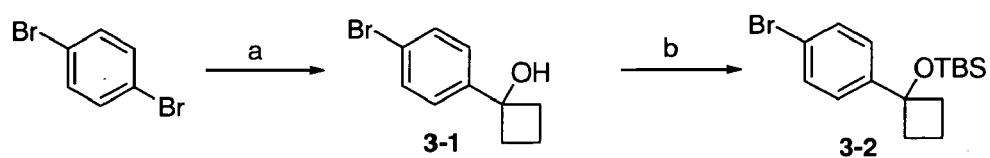
Figure 4:
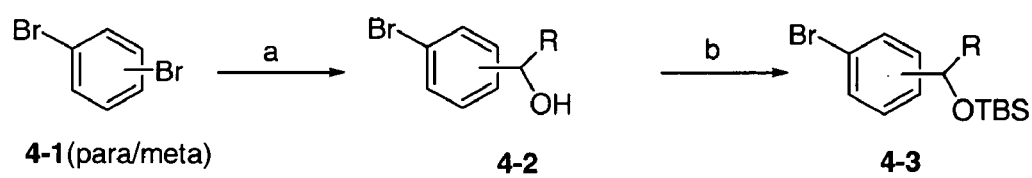
Figure 5:
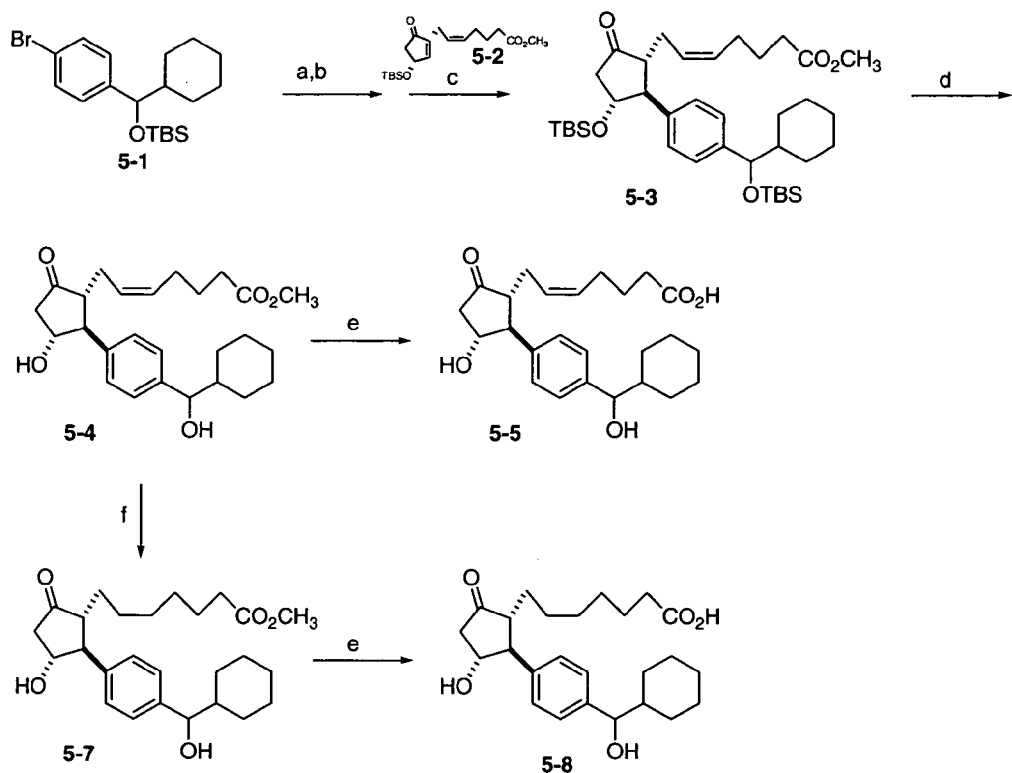
Figure 5:
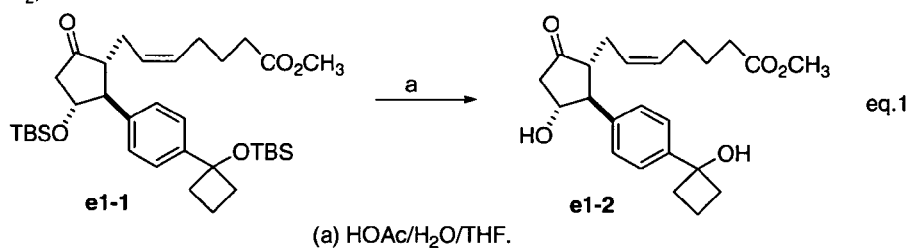
Figure 5:
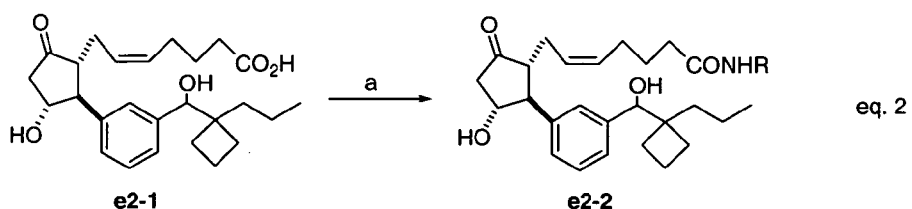
Figure 6:
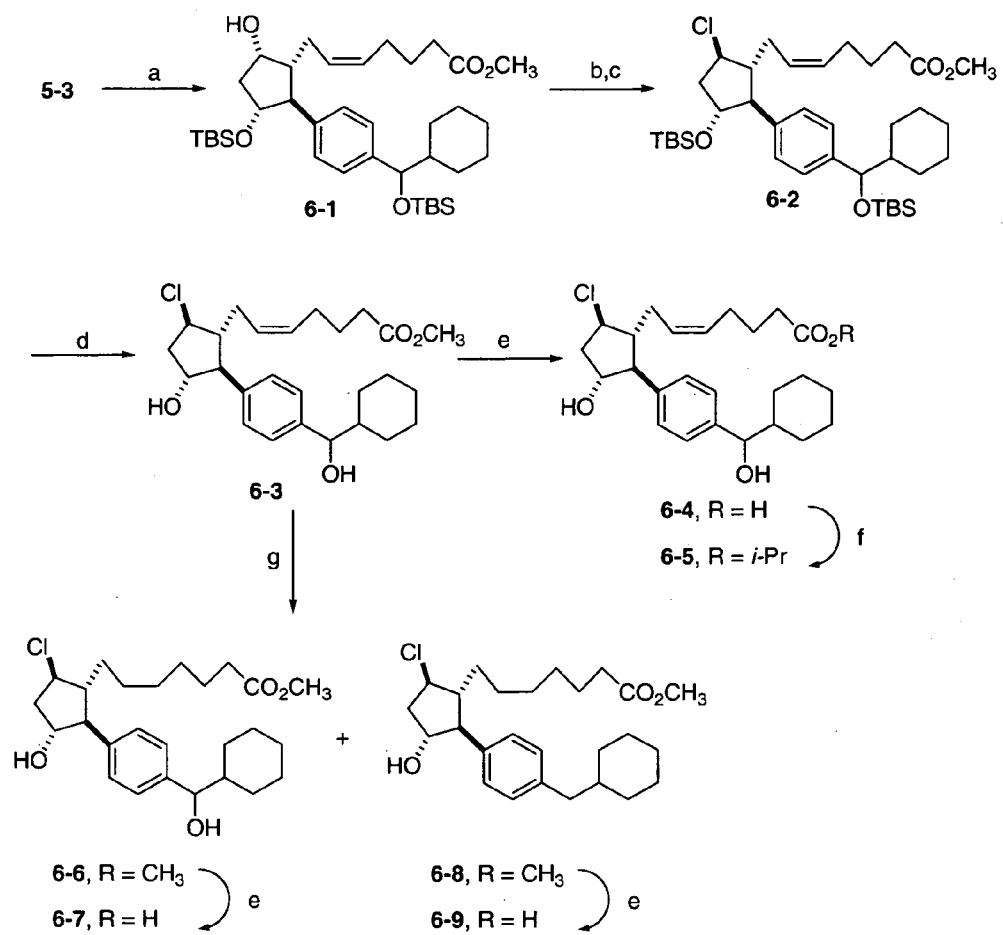
Figure 7:
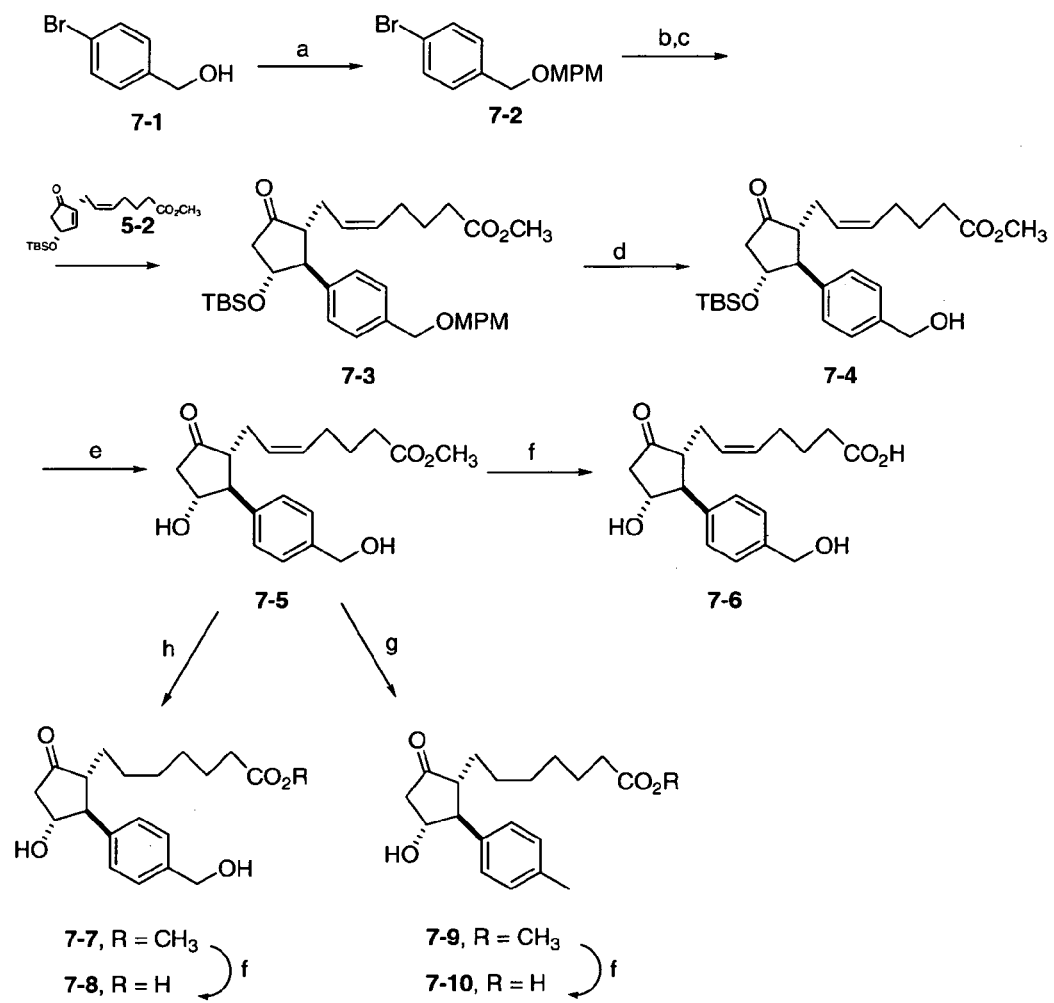
Figure 8:
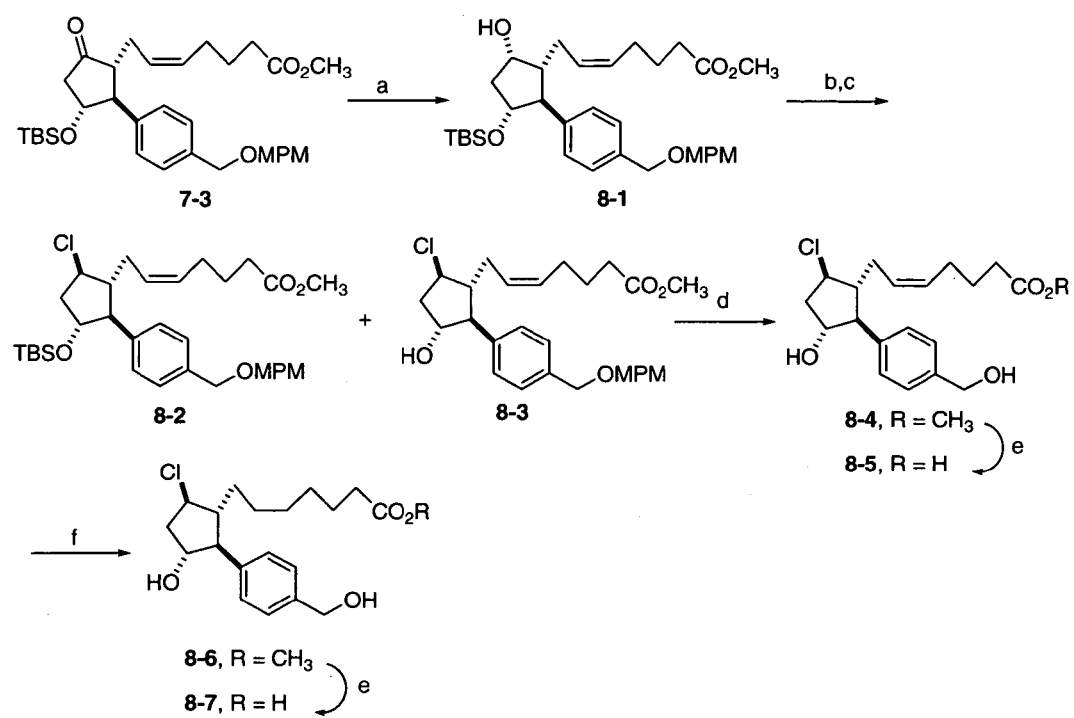
Figure 9:
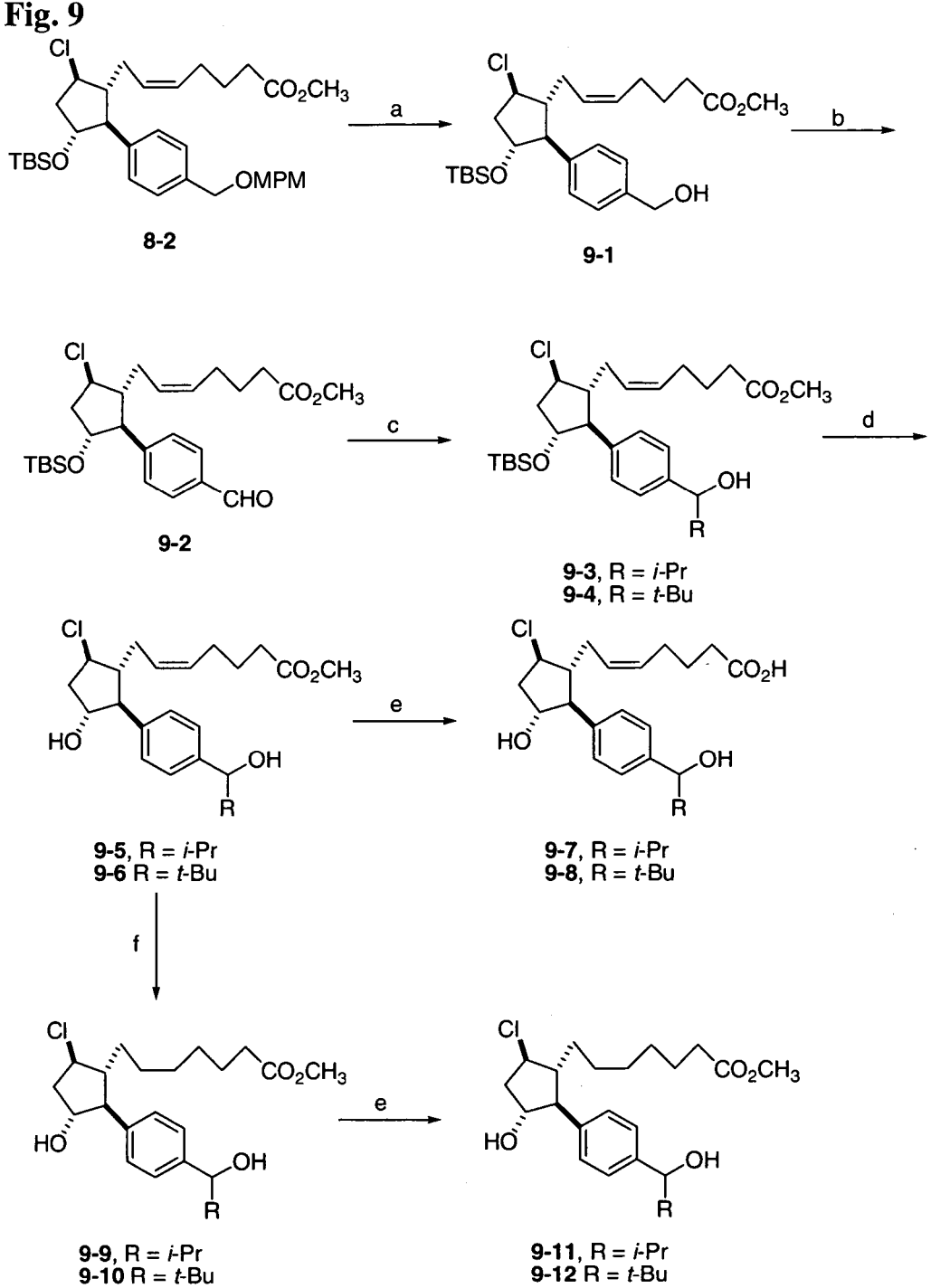
Figure 10:
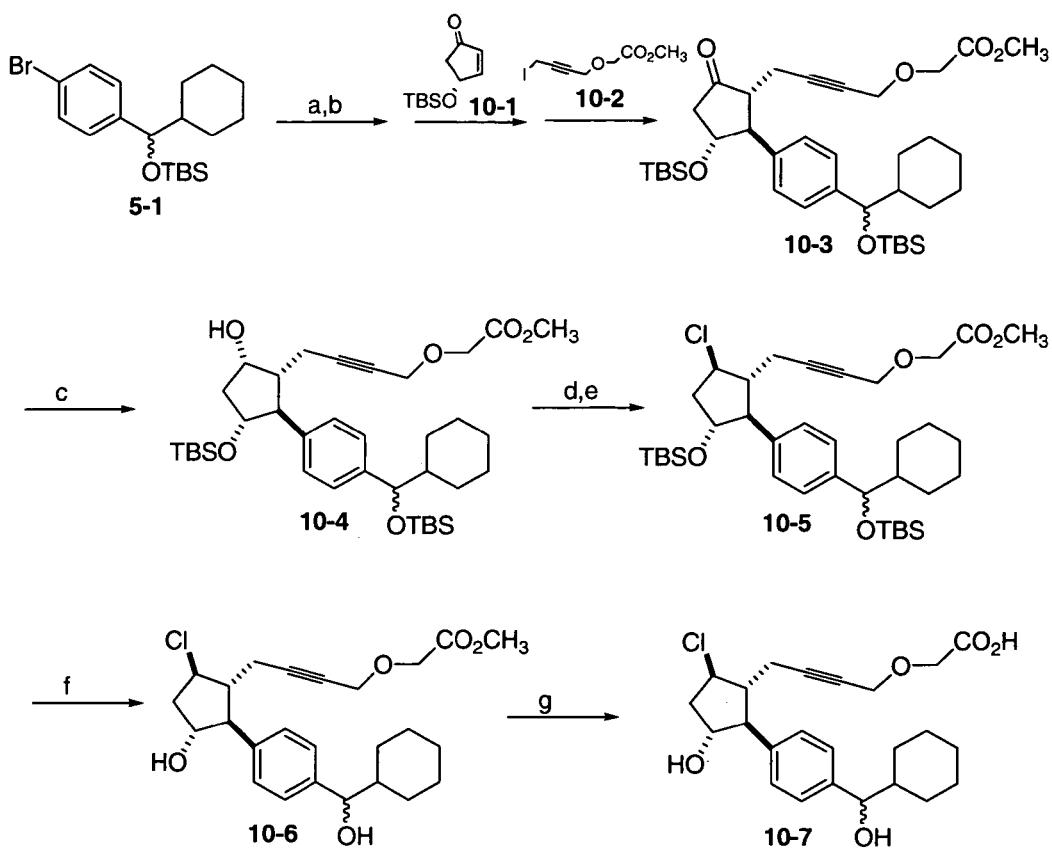
Figure 11:
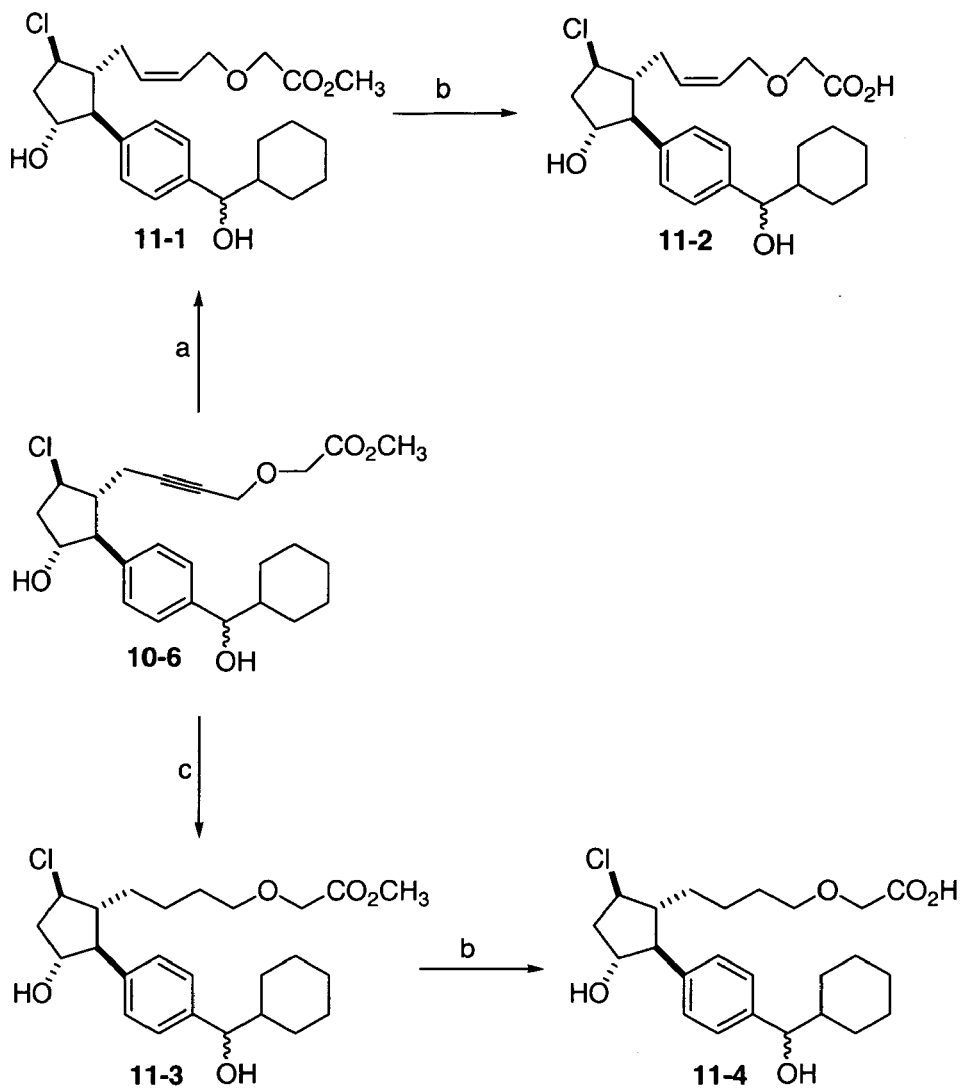
Figure 12:
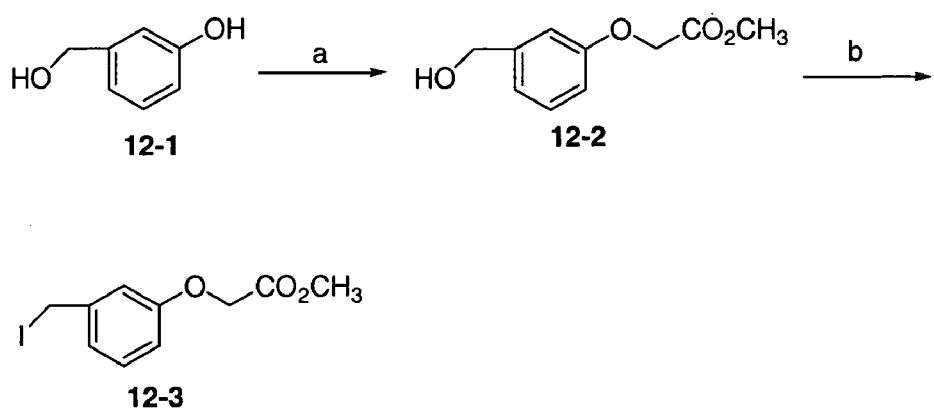
Figure 13:
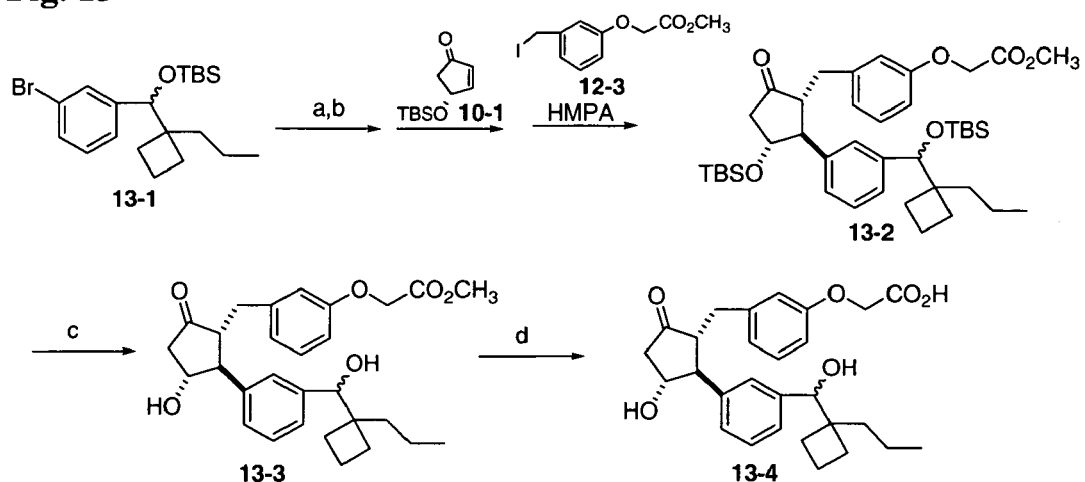
Figure 14:
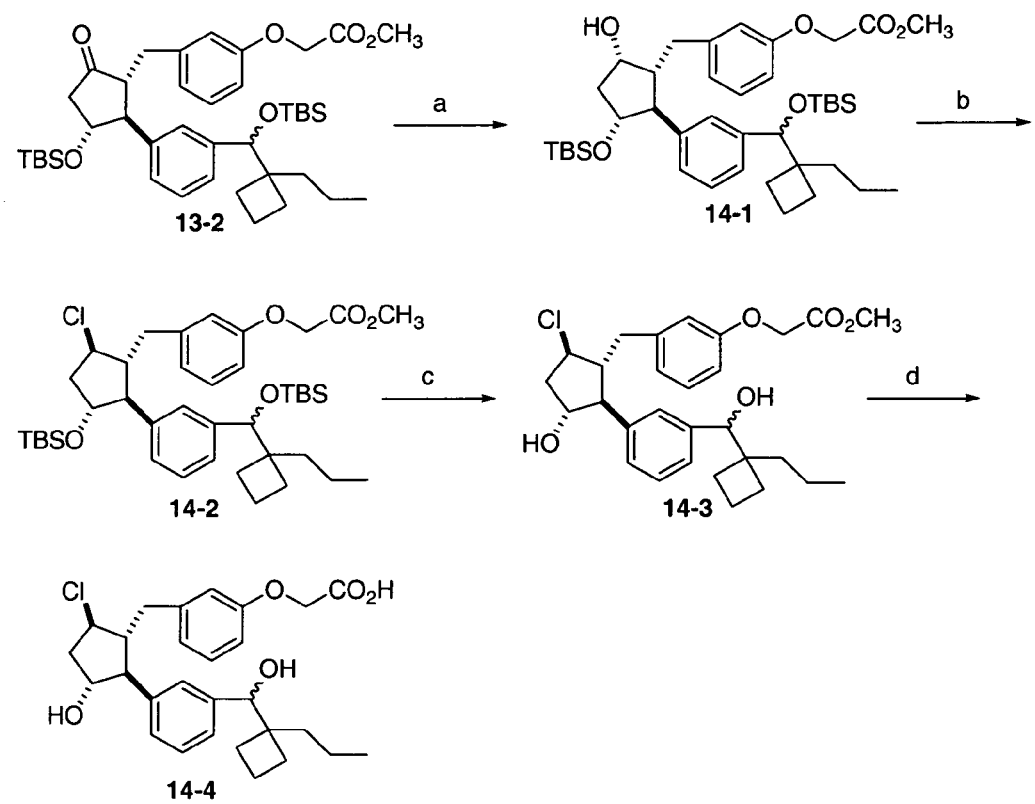
Figure 15:
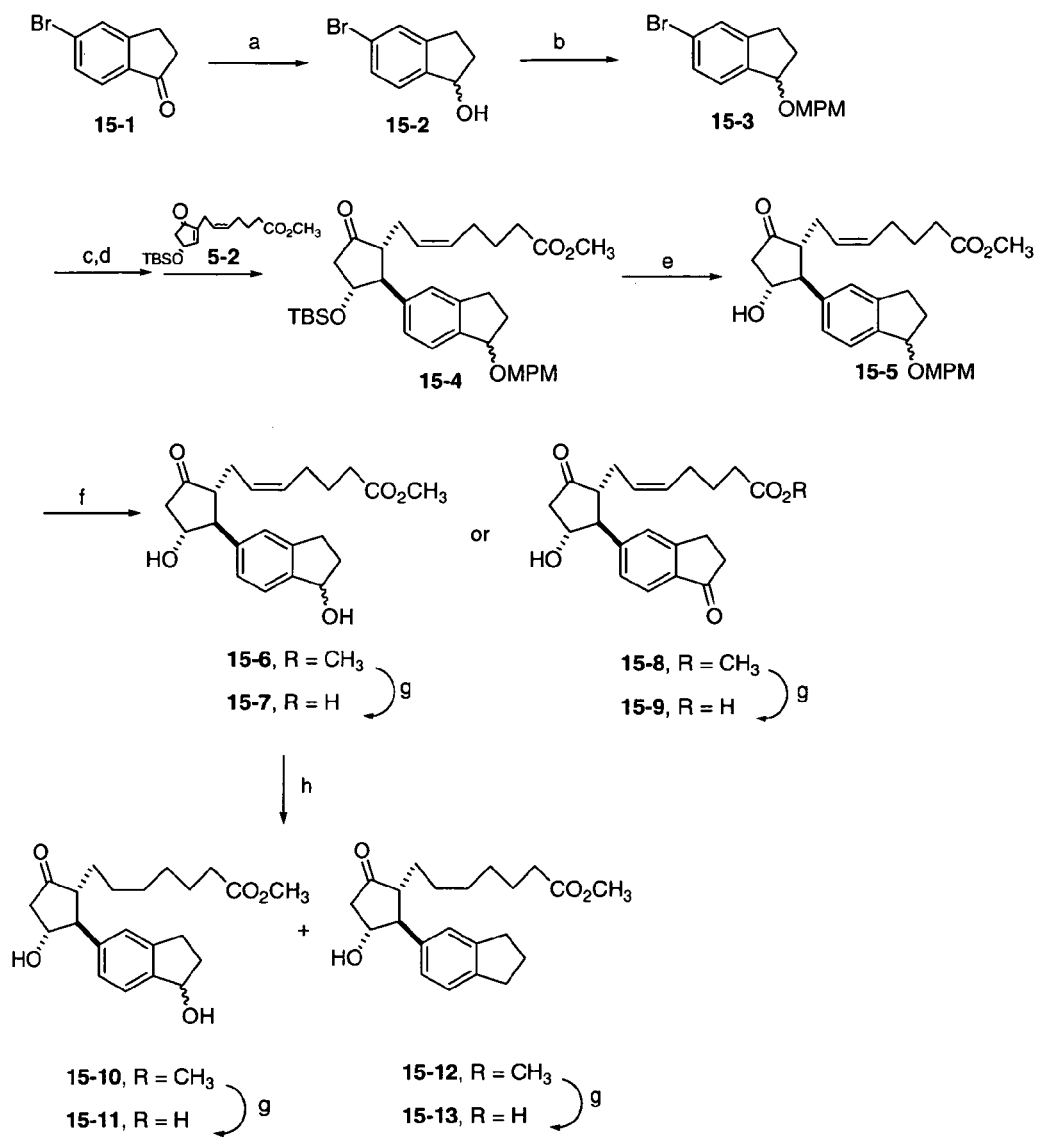
Figure 16:
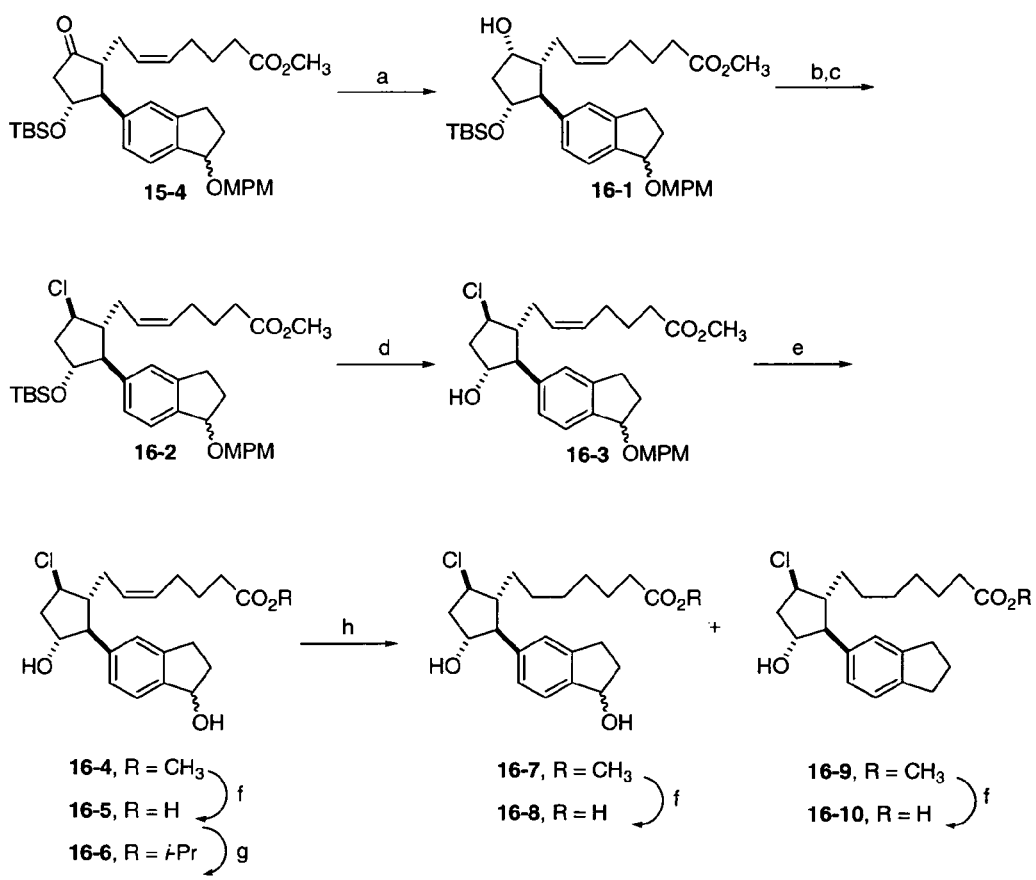
Figure 17:
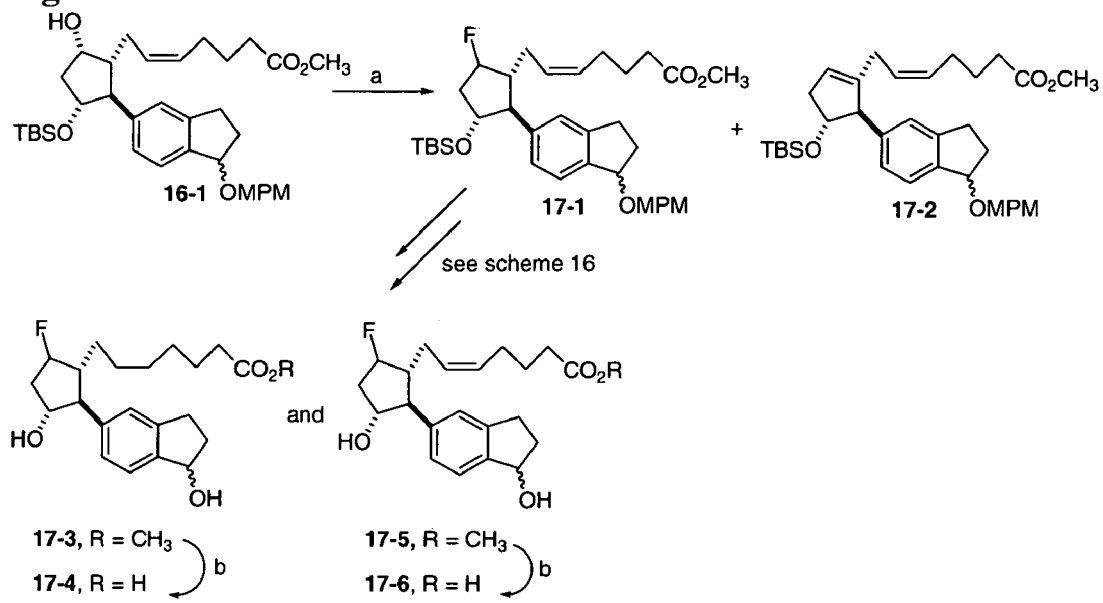

FIGS. 1–17 illustrate one way of preparing the compounds disclosed herein.

DETAILED DESCRIPTION OF THE INVENTION

Several of the carbon atoms on these compounds are chiral centers. While not intending to limit the scope of the invention in any way, or be bound in any way by theory, it is believed that many compounds and pharmaceutically active salts or prodrugs thereof having the stereochemistry shown below are particularly useful.

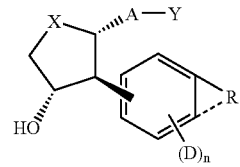

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

However, it is also advantageous if one or more of the bonds has the indicated stereochemistry, while the stereochemistry of other bonds to chiral centers may vary. Thus, while not intending to limit the scope of the invention in any way, compounds comprising

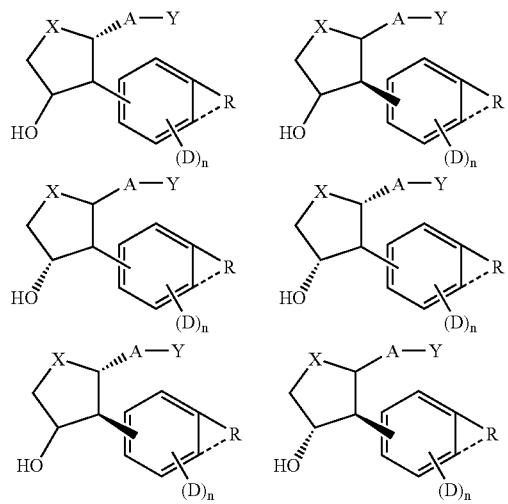

and the like, and pharmaceutically acceptable salts and prodrugs thereof, are particularly useful in the context disclosed herein.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Y is a carboxylic acid, sulfonic acid, or phosphonic acid functional group; or an amide or ester thereof comprising from 0 to 12 carbon atoms; or Y is a hydroxymethyl, or tetrazolyl functional group. Thus, while not intending to limit the scope of the invention in any way, in certain compounds Y is a carboxylic acid, sulfonic acid, or phosphonic acid functional group, i.e. one of the structures shown below.

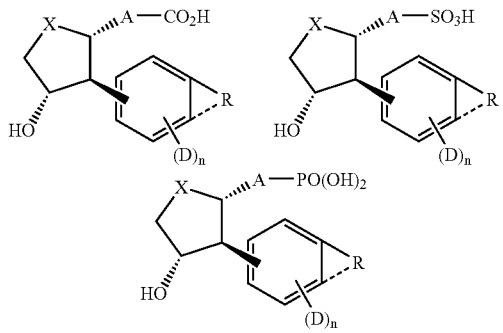

Salts of any of these acids of any pharmaceutically acceptable form may also be present.

Additionally, an amide or ester of one of the organic acids shown above comprising from 0 to 12 carbon atoms is also contemplated. In an ester, a hydrocarbyl moiety replaces a hydrogen of an acid such as in a carboxylic acid ester, e.g. $CO_2R^3$. In an amide, an amine group replaces an OH of the acid. An amine is a moiety having a central nitrogen which has exactly three bonds to C or H. Examples of amides include $CON(R^3)_2$, $CON(OR^3)R^3$, $CONH(CH_2CH_2OH)_2$, and $CONH(CH_2CH_2OH)$. Moieties such as $CONHSO_2R^3$ are also amides of the carboxylic acid notwithstanding the fact that they may also be considered to be amides of the sulfonic acid $R^3$—$SO_3H$.

Finally, while not intending to limit the scope of the invention in any way, Y may also be a hydroxymethyl, or a tetrazolyl functional group, i.e. compounds having a structure such as one of those shown below.

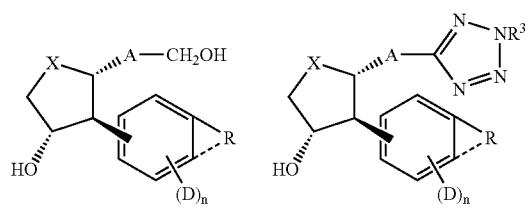

When $R^3$ is hydrogen, the tetrazolyl functional group has two tautomeric forms, which can rapidly interconvert in aqueous or biological media, and are thus equivalent to one another. These tautomers are shown below.

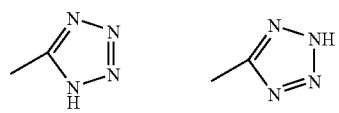

Additionally, if $R^3$ is $C_1$–$C_6$ alkyl, phenyl, or biphenyl, other isomeric forms of the tetrazolyl functional group such as the one shown below are also possible, all of these are considered to be within the scope of the term "tetrazolyl."

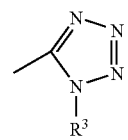

While not intending to limit the scope of the invention in any way, in one embodiment, Y is selected from the group consisting of $CO_2(R^3)$, $CON(R^3)_2$, $CON(OR^3)R^3$, $CON(CH_2CH_2OH)_2$, $CONH(CH_2CH_2OH)$, $CH_2OH$, $P(O)(OH)_2$, $CONHSO_2R^3$, $SO_2N(R^3)_2$, $SO_2NHR^3$, and tetrazolyl-$R^3$; wherein $R^3$ is independently H, $C_1$–$C_6$ alkyl, phenyl, or biphenyl.

In relation to the identity of A disclosed in the chemical structures presented herein, in the broadest sense, A is —$(CH_2)_6$—, cis —$CH_2CH$=$CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is substituted or unsubstituted phenyl or monocyclic heteroaryl, the sum of m and o is from 1 to 3, and wherein one $CH_2$ may be substituted with S or O.

In other words, while not intending to be limiting, A may be —$(CH_2)_6$—, cis —$CH_2CH$=$CH$—$(CH_2)_3$—, or —$CH_2C\equiv C$—$(CH_2)_3$—.

Alternatively, A may be a group which is related to one of these three moieties in that any carbon is substituted with S or O. For example, while not intending to limit the scope of the invention in any way, A may be an S substituted moiety such as one of the following or the like.

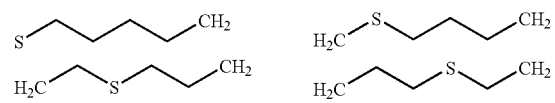

-continued

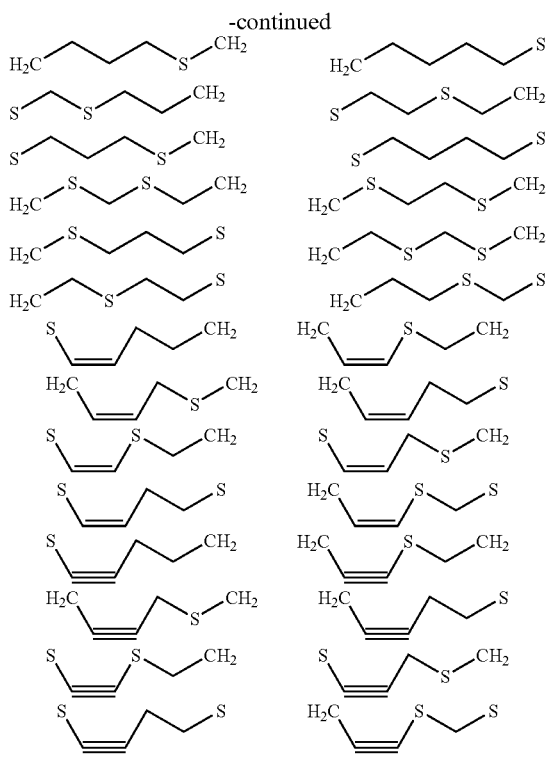

Alternatively, while not intending to limit the scope of the invention in any way, A may be an O substituted moiety such as one of the following or the like.

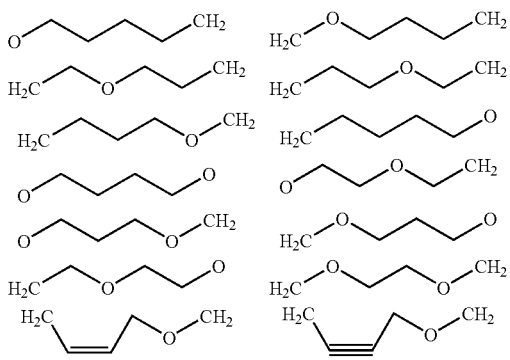

Alternatively, while not intending to limit the scope of the invention in any way, A may have both an O and an S substituted in the chain, such as one of the following or the like.

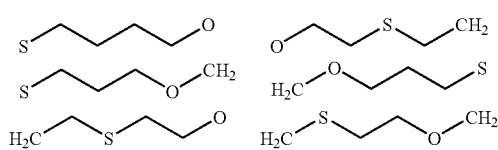

Alternatively, while not intending to limit the scope of the invention in any way, in certain embodiments A is —(CH$_2$)$_n$—Ar—(CH$_2$)$_o$— wherein Ar is substituted or unsubstituted phenyl or monocyclic heteroaryl, the sum of m and o is from 1 to 4, and wherein one CH$_2$ may be substituted with S or O. In other words, while not intending to limit the scope of the invention in any way, A comprises from 1 to 4 CH$_2$ moieties and Ar, e.g. —CH$_2$—Ar—, —(CH$_2$)$_2$—Ar—, —CH$_2$—ArCH$_2$—, —CH$_2$Ar(CH$_2$)$_2$—, —(CH$_2$)$_2$—Ar(CH$_2$)$_2$—, and the like; or A comprises O, from 0 to 3 CH$_2$ moieties, and Ar, as in for example, —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, as in for example, —S—Ar—, Ar—CH$_2$—S—, —S—Ar—(CH$_2$)$_2$—, —S—CH$_2$—Ar—, —S—CH$_2$—Ar—(CH$_2$)$_2$, and the like.

Ar is substituted or unsubstituted phenyl or substituted or unsubstituted monocyclic heteroaryl. In one embodiment, Ar is substituted or unsubstituted phenyl, thienyl, furyl, or pyridinyl. In another embodiment Ar is phenyl (Ph). In another embodiment A is —(CH$_2$)$_2$—Ph. While not intending to limit scope of the invention in any way, substituents may have 4 or less heavy atoms, or in other words, non hydrogen atoms. Any number of hydrogen atoms required for a particular substituent will also be included. Thus, the substituent may be C4 or lower hydrocarbyl, including C4 or lower alkyl, alkenyl, alkynyl, and the like; C3 or lower hydrocarbyloxy; CF$_3$; halo, such as F, Cl, or Br; hydroxyl; NH$_2$ and alkylamine functional groups up to C3; other N or S containing substituents; and the like.

In one embodiment A is —CH$_2$)$_m$—Ar—(CH$_2$)$_o$— wherein Ar is phenyl, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is phenyl.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$—Ph— wherein one CH$_2$ may be substituted with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$—Ph—.

D is a moiety comprising from 1 to 6 non-hydrogen atoms, in other words, there are from 1 to 6 atoms which are not hydrogen, and any number of hydrogen atoms required to form the complete substituent. For example, a methyl substituent has 1 carbon atom and 3 hydrogen atoms. Other example substituents include other hydrocarbyl moieties comprising from 1 to 6 carbon atoms including alkyl such as ethyl, propyl, isopropyl, butyl and isomers thereof, pentyl and isomers thereof, hexyl and isomers thereof; cyclic and unsaturated hydrocarbyls having 1 to 6 carbon atoms; CO$_2$H and salts thereof; alkoxy up to C$_5$ such as methoxy, ethoxy, propoxy, isopropoxy, a butoxy isomer, or a pentoxy isomer; carboxylic acid esters; CN; NO$_2$; CF$_3$; F; Cl; Br; I; sulfonyl esters; SO$_3$H and salts thereof; and the like. D may be in any reasonable position on the phenyl ring.

In certain compounds, n is 0. In other compounds n is 1, in other compounds n is 2, and in other compounds n is 3.

A hydrocarbyl moiety refers to a moiety consisting of only carbon and hydrogen. While not intending to limit the scope of the invention in any way, examples of different types of hydrocarbyl moiety are as follows.

One type of hydrocarbyl is alkyl including:

a) linear alkyl such as methyl, ethyl, propyl, n-butyl, n-pentyl, n-hexyl, and the like;

b) branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

c) cycloalkyl such as cyclopropyl, cyclobutyl, cyclopentyl, cyclohexyl, cycloheptyl, etc.; and d) alkyl fragments consisting of both cyclic and noncyclic components, whether linear or branched, which may be attached to the remainder of the molecule at any available position including terminal, internal, or ring carbon atoms.

In analogy to alkyl, there is linear, branched, cycloalkyl, and combination hydrocarbyl.

Another type of hydrocarbyl is alkenyl, which is similar to alkyl with the exception that a double bond is present.

Another type of hydrocarbyl is alk(poly)enyl, which is similar to alkenyl, except that more than one double bond is present.

Another type of hydrocarbyl is alkynyl or an alk(poly)ynyl, which is similar to alkenyl or alk(poly)ynyl except that one or more triple bonds are present.

Another type of hydrocarbyl is aryl, which includes phenyl, naphthyl and other aromatic hydrocarbyls.

Additionally, combinations of any of the above in any manner imaginable to those of ordinary skill in the art are also hydrocarbyl.

A hydrocarbyl moiety comprising a cyclic structure comprises a cycloalkyl, cycloalkenyl, cycloalkynyl, cycloalkyl(poly)enyl, cycloalkyl(poly)ynyl, aryl, and the like; and may consist of only the ring or may be a combination of the ring and one or more of the linear, branched, or cyclic hydrocarbyl fragments; or may be a fused polycyclic structure.

A hydroxyhydrocarbyl moiety consists of a combination of a hydrocarbyl moiety and a hydroxyl group. In other words, a hydrogen atom of the hydrocarbyl moiety is substituted with a hydroxyl group. The hydroxyhydrocarbyl moiety attaches to the remainder of the molecule at a carbon atom.

Thus, while not intending to limit the scope of the invention in any way, as R is a hydrocarbyl or a hydroxyhydrocarbyl moiety comprising from 1 to 12 atoms, embodiments having R as any of the hydrocarbyl or hydroxycarbyl moieties listed above are specifically contemplated herein. R may also be a different moiety which may be considered hydrocarbyl or hydroxyhydrocarbyl according to the description given herein.

In certain compounds, R is a hydroxyhydrocarbyl having the hydroxyl group attached to the carbon atom which is also attached to the remainder of the molecule. In other words the hydroxyl group and the remainder of the molecule are on geminal positions on the hydrocarbyl moiety. This type of hydroxyhydrocarbyl moiety is referred to as a 1-hydroxyhydrocarbyl moiety herein. Non-linear hydroxyhydrocarbyl is hydroxyhydrocarbyl wherein the hydrocarbyl portion is not linear, i.e. it has branching and/or a ring.

In other compounds R is hydroxyhydrocarbyl having the hydroxyl group attached to a carbon atom which is directly attached to the remaining part of the molecule. These particular hydroxyhydrocarbyl are called 2-hydroxyhydrocarbyl herein. For example, —C(CH$_3$)$_2$CH$_2$OH is 2-hydroxyhydrocarbyl. While not intending to limit the scope of the invention in any way, a general structure where R is 2-hydrocarbyl is shown below.

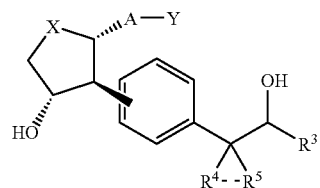

As with all other structures shown herein, pharmaceutically acceptable salts and prodrugs of compounds represent by these structures are also contemplated.

In one embodiment related to the above structure, R$^3$, R$^4$, and R$^5$ are independently H or C$_{1-6}$ alkyl. As the dashed line indicates the presence or absence of a bond, R$^4$ and R$^5$ may be two separate moieties. For example, while not intending to be limiting, R$^4$ and R$^5$ may be methyl, and no bond would be present where indicated by the dashed line. Alternatively, while not intending to limit the scope of the invention in any way, R$^4$ and R$^5$ may form a ring. In other words, a compound such as the one shown below is possible, wherein x is from 1 to 6.

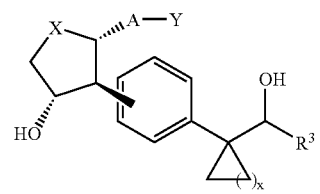

Pharmaceutically acceptable salts and prodrugs of compounds represent by these structures are also contemplated.

In certain compounds, R comprises from 6 to 9 carbon atoms and a cyclic structure. In other compounds, R comprises from 1 to 5 carbon atoms. In certain compounds R is hydroxyalkyl having from 1 to 5 carbon atoms. In other compounds R is a 1-hydroxyhydrocarbyl moiety comprising from 6 to 9 carbon atoms and a cyclic structure. In other compounds R is a 1-hydroxyhydrocarbyl moiety comprising from 6 to 9 carbon atoms and a cyclic structure comprising from 4–7 carbon atoms. In other words, the cyclic structure part of R is a cyclobutyl, cyclopentyl, cyclohexyl, or cycloheptyl fragment. The cyclic structure part of R may also be a cycloalkenyl or cycloalkynyl fragment such as cyclopentene or cyclohexene. In other compounds R is a hydrocarbyl moiety comprising from 1 to 5 carbon atoms. In other words, R is methyl, ethyl, propyl, isopropyl, a butyl isomer such as t-butyl, or a pentyl isomer. In certain compounds R is t-butyl.

Certain R groups are specifically contemplated herein. These are shown below, where PR represents the remaining part of the molecule.

 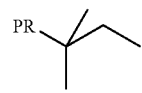 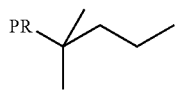

-continued

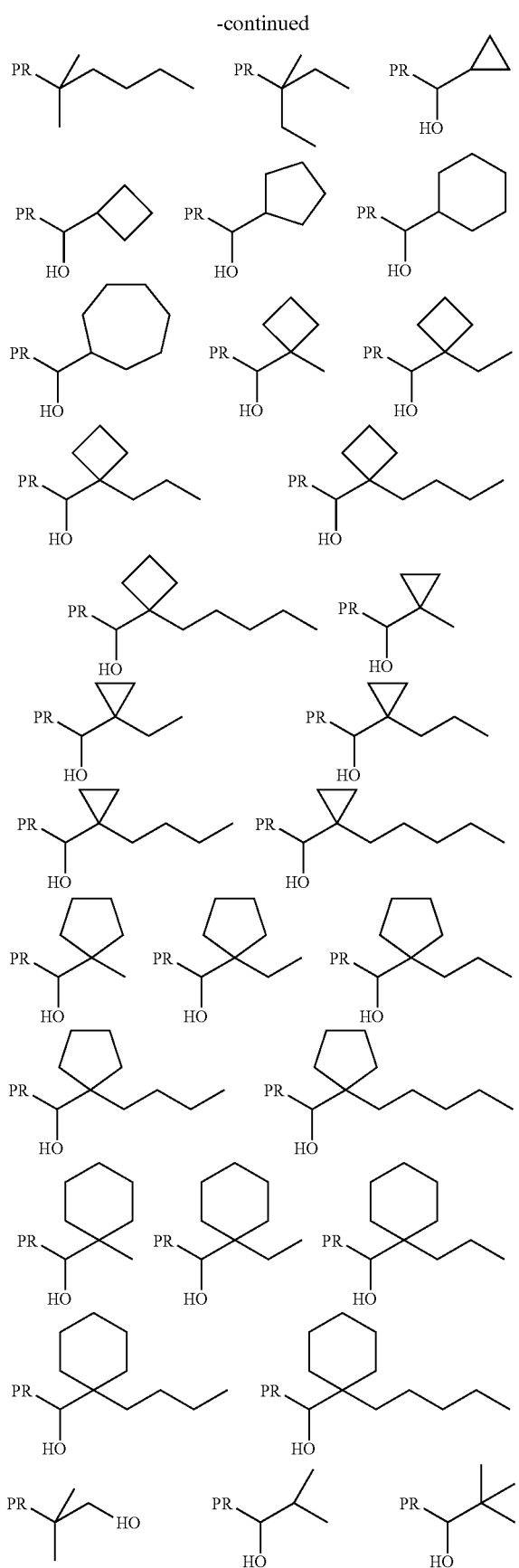

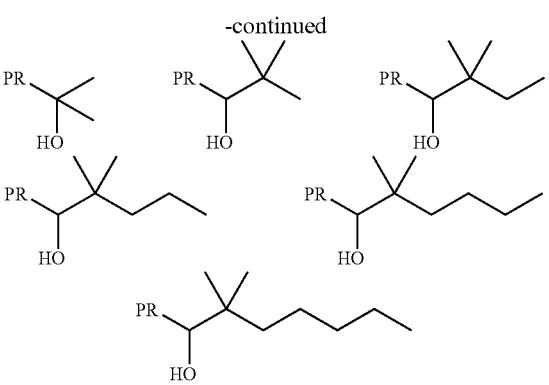

As there is a dashed line between R and the phenyl ring, cyclic structures having two carbon atoms of the phenyl ring are possible. While not intending to limit the scope of the invention in any way, compounds such as those represented by the structure below are therefore possible.

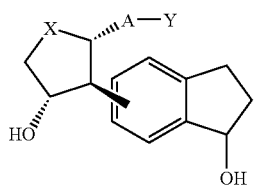

Pharmaceutically acceptable salts and prodrugs thereof are also contemplated.

Other useful compounds comprise

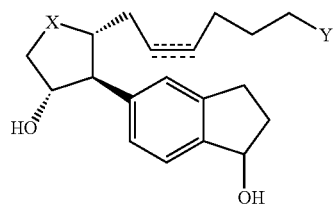

or a pharmaceutically acceptable salt, or a prodrug thereof.

Other useful compounds comprise.

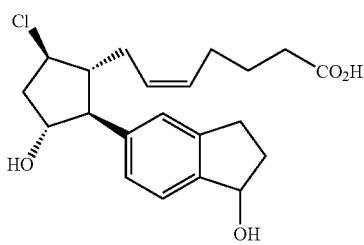

or a pharmaceutically acceptable salt, or a prodrug thereof.

Those of ordinary skill in the art understand that any value which refers to the number of atoms, moieties, etc., on a small molecule will be an integer, i.e. 0, 1, 2, 3, etc.

Certain useful compounds comprise

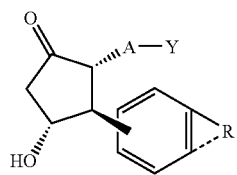

or a pharmaceutically acceptable salt, or a prodrug thereof.

Other useful compounds comprise

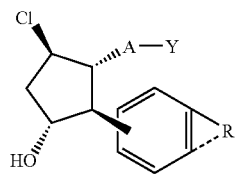

or a pharmaceutically acceptable salt, or a prodrug thereof.

Other useful examples of compounds comprise

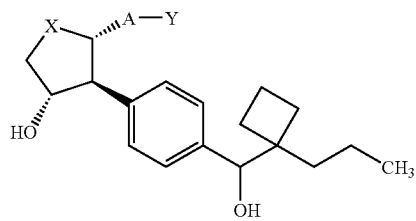

or a pharmaceutically acceptable salt, or a prodrug thereof.

Other compounds comprise

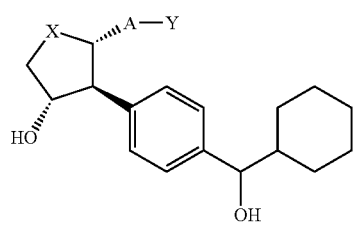

or a pharmaceutically acceptable salt, or a prodrug thereof.

Other embodiments comprise

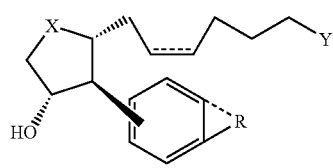

or a pharmaceutically acceptable salt, or a prodrug thereof, wherein a dashed line indicates the presence or absence of a bond.

Other compounds comprise

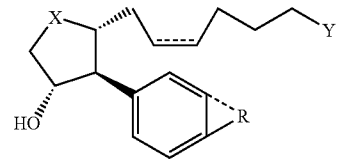

wherein X is C=O or CHCl; and

R is alkyl having from 3 to 6 carbon atoms.

Other compounds comprise

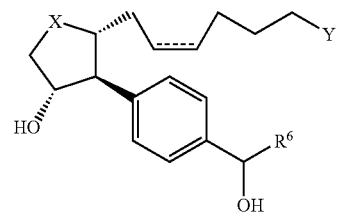

or a pharmaceutically acceptable salt, or a prodrug thereof, wherein $R^6$ is cycloalkyl comprising from 3 to 10 carbon atoms; and X is C=O or CHCl.

Other compounds comprise

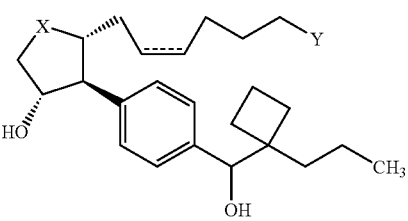

or a pharmaceutically acceptable salt, or a prodrug thereof.

Other embodiments comprise

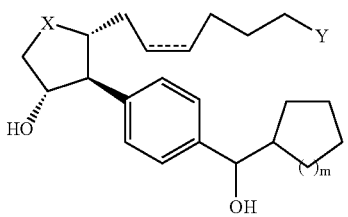

or a pharmaceutically acceptable salt, or a prodrug thereof wherein m is an integer having a value of from 0 to 3.

Other compounds comprise

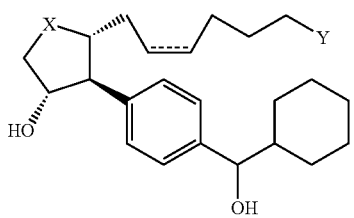

or a pharmaceutically acceptable salt, or a prodrug thereof. Other compounds comprise

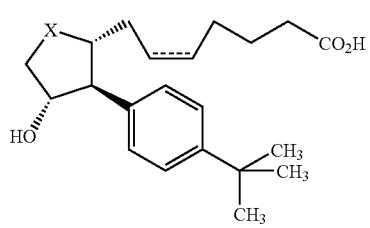

or a pharmaceutically acceptable salt, or a prodrug thereof. Other useful compounds comprise

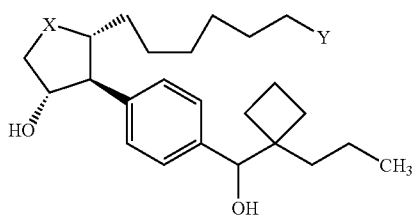

or a pharmaceutically acceptable salt, or a prodrug thereof. Other useful embodiments comprise

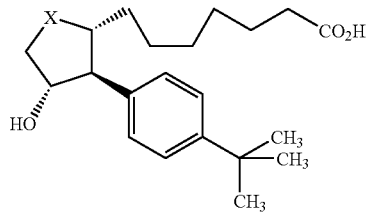

or a pharmaceutically acceptable salt, or a prodrug thereof.

Another useful compound is

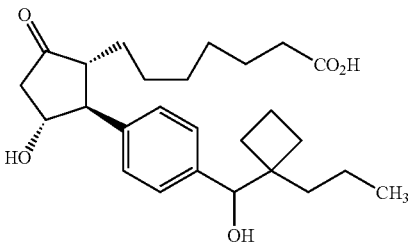

or a pharmaceutically acceptable salt, or a prodrug thereof. Another useful compound is

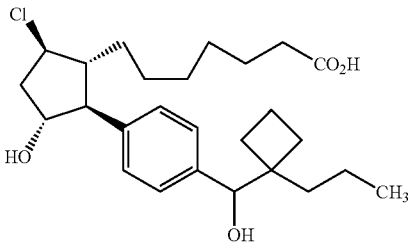

or a pharmaceutically acceptable salt, or a prodrug thereof. Another useful compound is

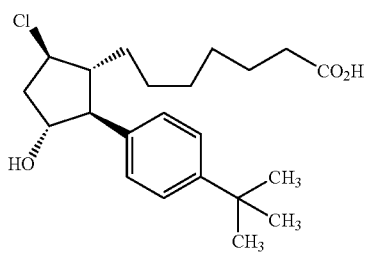

or a pharmaceutically acceptable salt, or a prodrug thereof. Another useful compound is

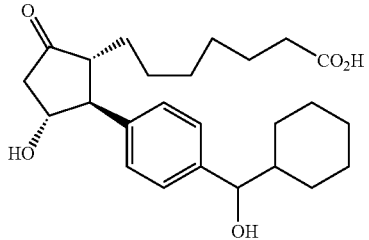

or a pharmaceutically acceptable salt, or a prodrug thereof.

Another useful compound is

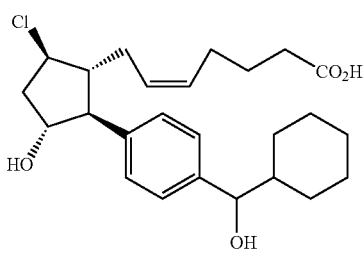

or a pharmaceutically acceptable salt, or a prodrug thereof. Certain compounds comprise

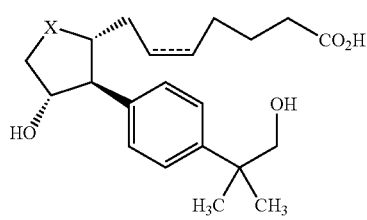

or a pharmaceutically acceptable salt or a prodrug thereof. Other compounds comprise

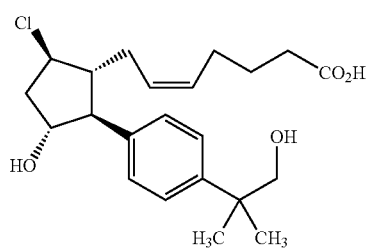

or a pharmaceutically acceptable salt or a prodrug thereof. Another useful compound is

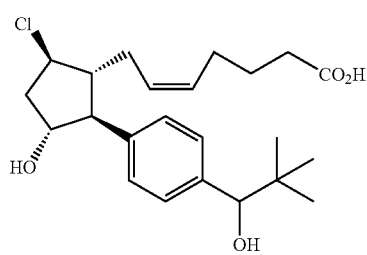

or a pharmaceutically acceptable salt, or a prodrug thereof.

Another useful compound is

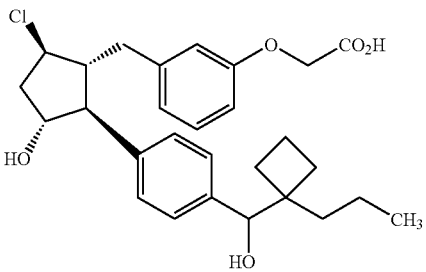

or a pharmaceutically acceptable salt or a prodrug thereof. Another useful compound is

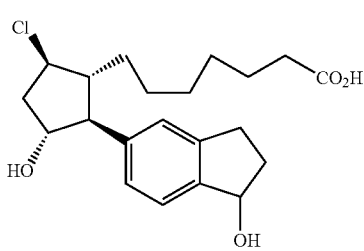

or a pharmaceutically acceptable salt or a prodrug thereof. Other compounds comprise

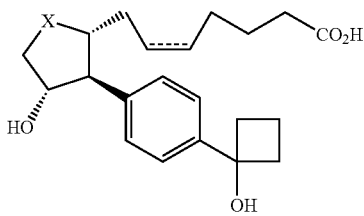

or a pharmaceutically acceptable salt or a prodrug thereof wherein X is C=O or CHCl.

Another useful compound is

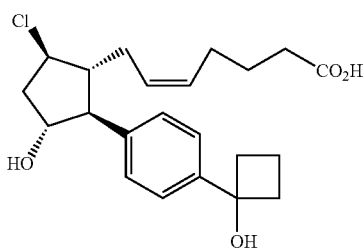

or a pharmaceutically acceptable salt or a prodrug thereof.

Other compounds comprise
(Z)-7-{(1R,2S,3R)-2-[4-(Cyclohexyl-hydroxy-methyl)-phenyl]-3-hydroxy-5-oxo-cyclopentyl}-hept-5-enoic acid methyl ester (5-4);
(Z)-7-{(1R,2S,3R)-2-[4-(Cyclohexyl-hydroxy-methyl)-phenyl]-3-hydroxy-5-oxo-cyclopentyl}-hept-5-enoic acid (5—5);
7-{(1R,2S,3R)-2-[4-(Cyclohexyl-hydroxy-methyl)-phenyl]-3-hydroxy-5-oxo-cyclopentyl}-heptanoic acid methyl ester (5-7);
7-{(1R,2S,3R)-2-[4-(Cyclohexyl-hydroxy-methyl)-phenyl]-3-hydroxy-5-oxo-cyclopentyl}-heptanoic acid (5-8);
(Z)-7-((1R,2S,3R)-3-Hydroxy-2-{4-[hydroxy-(1-propyl-cyclobutyl)-methyl]-phenyl}-5-oxo-cyclopentyl)-hept-5-enoic acid methyl ester;
(Z)-7-((1R,2S,3R)-3-Hydroxy-2-{4-[hydroxy-(1-propyl-cyclobutyl)-methyl]-phenyl}-5-oxo-cyclopentyl)-hept-5-enoic acid;
7-((1R,2S,3R)-3-Hydroxy-2-{4-[hydroxy-(1-propyl-cyclobutyl)-methyl]-phenyl}-5-oxo-cyclopentyl)-heptanoic acid methyl ester;
7-((1R,2S,3R)-3-Hydroxy-2-{4-[hydroxy-(1-propyl-cyclobutyl)-methyl]-phenyl}-5-oxo-cyclopentyl)-heptanoic acid;
(Z)-7-[(1R,2S,3R)-2-(4-tert-Butyl-phenyl)-3-hydroxy-5-oxo-cyclopentyl]-hept-5-enoic acid methyl ester;
(Z)-7-[(1R,2S,3R)-2-(4-tert-Butyl-phenyl)-3-hydroxy-5-oxo-cyclopentyl]-hept-5-enoic acid;
7-[(1R,2S,3R)-2-(4-tert-Butyl-phenyl)-3-hydroxy-5-oxo-cyclopentyl]-heptanoic acid methyl ester;
7-[(1R,2S,3R)-2-(4-tert-Butyl-phenyl)-3-hydroxy-5-oxo-cyclopentyl]-heptanoic acid. (Z)-7-{(1R,2S,3R)-3-Hydroxy-2-[4-(2-hydroxy-1,1-dimethyl-ethyl)-phenyl]-5-oxo-cyclopentyl}-hept-5-enoic acid methyl ester;
(Z)-7-{(1R,2S,3R)-3-Hydroxy-2-[4-(2-hydroxy-1,1-dimethyl-ethyl)-phenyl]-5-oxo-cyclopentyl}-hept-5-enoic acid;
7-{(1R,2S,3R)-3-Hydroxy-2-[4-(2-hydroxy-1,1-dimethyl-ethyl)-phenyl]-5-oxo-cyclopentyl}-heptanoic acid methyl ester;
7-{(1R,2S,3R)-3-Hydroxy-2-[4-(2-hydroxy-1,1-dimethyl-ethyl)-phenyl]-5-oxo-cyclopentyl}-heptanoic acid;
(Z)-7-{(1R,2S,3R)-3-Hydroxy-2-[4-(1-hydroxy-cyclobutyl)-phenyl]-5-oxo-cyclopentyl}-hept-5-enoic acid methyl ester (e1-2);
7-{(1R,2S,3R)-3-Hydroxy-2-[4-(1-hydroxy-cyclobutyl)-phenyl]-5-oxo-cyclopentyl}-heptanoic acid methyl ester;
7-{(1R,2S,3R)-3-Hydroxy-2-[4-(1-hydroxy-cyclobutyl)-phenyl]-5-oxo-cyclopentyl}-heptanoic acid;
(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid methyl ester;
(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid (e2-1);
7-((1R,2S,3R)-3-Hydroxy-2-{3-[hydroxy-(1-propyl-cyclobutyl)-methyl]-phenyl}-5-oxo-cyclopentyl)-heptanoic acid methyl ester;
7-((1R,2S,3R)-3-Hydroxy-2-{3-[hydroxy-(1-propyl-cyclobutyl)-methyl]-phenyl}-5-oxo-cyclopentyl)-heptanoic acid;
(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid (2-hydroxy-ethyl)-amide (e2—2, R=2-hydroxyethyl);
(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid ethyl amide (e2—2, R=ethyl);
(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid ethyl amide (e2—2, R=H);
(Z)-7-{(1R,2S,3R,5R)-5-Chloro-2-[4-(cyclohexyl-hydroxy-methyl)-phenyl]-3-hydroxy-cyclopentyl}-hept-5-enoic acid methyl ester (6-3);
(Z)-7-{(1R,2S,3R,5R)-5-Chloro-2-[4-(cyclohexyl-hydroxy-methyl)-phenyl]-3-hydroxy-cyclopentyl}-hept-5-enoic acid (6-4);
(Z)-7-{(1R,2S,3R,5R)-5-Chloro-2-[4-(cyclohexyl-hydroxy-methyl)-phenyl]-3-hydroxy-cyclopentyl}-hept-5-enoic acid isopropyl ester (6-5);
7-{(1R,2S,3R,5R)-5-Chloro-2-[4-(cyclohexyl-hydroxy-methyl)-phenyl]-3-hydroxy-cyclopentyl}-heptanoic acid methyl ester (6—6);
7-[(1R,2S,3R,5R)-5-Chloro-2-(4-cyclohexylmethyl-phenyl)-3-hydroxy-cyclopentyl]-heptanoic acid methyl ester (6-8);
7-{(1R,2S,3R,5R)-5-Chloro-2-[4-(cyclohexyl-hydroxy-methyl)-phenyl]-3-hydroxy-cyclopentyl}-heptanoic acid (6-7);
7-[(1R,2S,3R,5R)-5-Chloro-2-(4-cyclohexylmethyl-phenyl)-3-hydroxy-cyclopentyl]-heptanoic acid (6-9);
(Z)-7-((1R,2S,3R,5R)-5-Chloro-3-hydroxy-2-{3-[hydroxy-(1-propyl-cyclobutyl)-methyl]-phenyl}-cyclopentyl)-hept-5-enoic acid methyl ester;
(Z)-7-((1R,2S,3R,5R)-5-Chloro-3-hydroxy-2-{3-[hydroxy-(1-propyl-cyclobutyl)-methyl]-phenyl}-cyclopentyl)-hept-5-enoic acid;
7-((1R,2S,3R,5R)-5-Chloro-3-hydroxy-2-{3-[hydroxy-(1-propyl-cyclobutyl)-methyl]-phenyl}-cyclopentyl)-heptanoic acid methyl ester;
7-((1R,2S,3R,5R)-5-Chloro-3-hydroxy-2-{3-[hydroxy-(1-propyl-cyclobutyl)-methyl]-phenyl}-cyclopentyl)-heptanoic acid;
(Z)-7-((1R,2S,3R,5R)-5-Chloro-3-hydroxy-2-{4-[hydroxy-(1-propyl-cyclobutyl)-methyl]-phenyl}-cyclopentyl)-hept-5-enoic acid methyl ester;
(Z)-7-((1R,2S,3R,5R)-5-Chloro-3-hydroxy-2-{4-[hydroxy-(1-propyl-cyclobutyl)-methyl]-phenyl}-cyclopentyl)-hept-5-enoic acid;
7-((1R,2S,3R,5R)-5-Chloro-3-hydroxy-2-{4-[hydroxy-(1-propyl-cyclobutyl)-methyl]-phenyl}-cyclopentyl)-heptanoic acid methyl ester;
7-((1R,2S,3R,5R)-5-Chloro-3-hydroxy-2-{4-[hydroxy-(1-propyl-cyclobutyl)-methyl]-phenyl}-cyclopentyl)-heptanoic acid;
(Z)-7-[(1R,2S,3R,5R)-2-(4-tert-Butyl-phenyl)-5-chloro-3-hydroxy-cyclopentyl]-hept-5-enoic acid methyl ester;
(Z)-7-[(1R,2S,3R,5R)-2-(4-tert-Butyl-phenyl)-5-chloro-3-hydroxy-cyclopentyl]-hept-5-enoic acid;
7-[(1R,2S,3R,5R)-2-(4-tert-Butyl-phenyl)-5-chloro-3-hydroxy-cyclopentyl]-heptanoic acid methyl ester;
7-[(1R,2S,3R,5R)-2-(4-tert-Butyl-phenyl)-5-chloro-3-hydroxy-cyclopentyl]-heptanoic acid;
(Z)-7-[(1R,2S,3R,5R)-2-(4-tert-Butyl-phenyl)-5-chloro-3-hydroxy-cyclopentyl]-hept-5-enoic acid isopropyl ester;
(Z)-7-{(1R,2S,3R,5R)-5-Chloro-3-hydroxy-2-[4-(1-hydroxy-cyclobutyl)-phenyl]-cyclopentyl}-hept-5-enoic acid methyl ester;
(Z)-7-{(1R,2S,3R,5R)-5-Chloro-3-hydroxy-2-[4-(1-hydroxy-cyclobutyl)-phenyl]-cyclopentyl}-hept-5-enoic acid;

7-{(1R,2S,3R,5R)-5-Chloro-3-hydroxy-2-[4-(1-hydroxy-cyclobutyl)-phenyl]-cyclopentyl}-heptanoic acid methyl ester;

7-{(1R,2S,3R,5R)-5-Chloro-3-hydroxy-2-[4-(1-hydroxy-cyclobutyl)-phenyl]-cyclopentyl}-heptanoic acid;

(Z)-7-{(1R,2S,3R,5R)-5-Chloro-3-hydroxy-2-[4-(2-hydroxy-1,1-dimethyl-ethyl)-phenyl]-cyclopentyl}-hept-5-enoic acid methyl ester;

(Z)-7-{(1R,2S,3R,5R)-5-Chloro-3-hydroxy-2-[4-(2-hydroxy-1,1-dimethyl-ethyl)-phenyl]-cyclopentyl}-hept-5-enoic acid;

7-{(1R,2S,3R,5R)-5-Chloro-3-hydroxy-2-[4-(2-hydroxy-1,1-dimethyl-ethyl)-phenyl]-cyclopentyl}-heptanoic acid methyl ester;

7-{(1R,2S,3R,5R)-5-Chloro-3-hydroxy-2-[4-(2-hydroxy-1,1-dimethyl-ethyl)-phenyl]-cyclopentyl}-heptanoic acid;

7-{(1R,2S,3R,5R)-5-Chloro-3-hydroxy-2-[4-(2-hydroxy-1,1-dimethyl-ethyl)-phenyl]-cyclopentyl}-heptanoic acid isopropyl ester;

(Z)-7-[(1R,2S,3R)-3-Hydroxy-2-(4-hydroxymethyl-phenyl)-5-oxo-cyclopentyl]-hept-5-enoic acid methyl ester (7-5);

(Z)-7-[(1R,2S,3R)-3-Hydroxy-2-(4-hydroxymethyl-phenyl)-5-oxo-cyclopentyl]-hept-5-enoic acid (7-6);

7-[(1R,2S,3R)-3-Hydroxy-2-(4-hydroxymethyl-phenyl)-5-oxo-cyclopentyl]-heptanoic acid methyl ester (7—7);

7-((1R,2S,3R)-3-Hydroxy-5-oxo-2-p-tolyl-cyclopentyl)-heptanoic acid methyl ester (7-9);

7-[(1R,2S,3R)-3-Hydroxy-2-(4-hydroxymethyl-phenyl)-5-oxo-cyclopentyl]-heptanoic acid (7-8);

(Z)-7-[(1R,2S,3R,5R)-5-Chloro-3-hydroxy-2-(4-hydroxymethyl-phenyl)-cyclopentyl]-hept-5-enoic acid methyl ester (8-4);

(Z)-7-[(1R,2S,3R,5R)-5-Chloro-3-hydroxy-2-(4-hydroxymethyl-phenyl)-cyclopentyl]-hept-5-enoic acid (8-5);

7-[(1R,2S,3R,5R)-5-Chloro-3-hydroxy-2-(4-hydroxymethyl-phenyl)-cyclopentyl]-heptanoic acid methyl ester (8-6);

7-[(1R,2S,3R,5R)-5-Chloro-3-hydroxy-2-(4-hydroxymethyl-phenyl)-cyclopentyl]-heptanoic acid (8-7);

(Z)-7-{(1R,2S,3R,5R)-5-Chloro-3-hydroxy-2-[4-(1-hydroxy-2-methyl-propyl)-phenyl]-cyclopentyl}-hept-5-enoic acid methyl ester (9-5);

(Z)-7-{(1R,2S,3R,5R)-5-Chloro-3-hydroxy-2-[4-(1-hydroxy-2,2-dimethyl-propyl)-phenyl]-cyclopentyl}-hept-5-enoic acid methyl ester (9-6);

(Z)-7-{(1R,2S,3R,5R)-5-Chloro-3-hydroxy-2-[4-(1-hydroxy-2-methyl-propyl)-phenyl]-cyclopentyl}-hept-5-enoic acid (9-7);

(Z)-7-{(1R,2S,3R,5R)-5-Chloro-3-hydroxy-2-[4-(1-hydroxy-2,2-dimethyl-propyl)-phenyl]-cyclopentyl}-hept-5-enoic acid (9-8);

7-{(1R,2S,3R,5R)-5-Chloro-3-hydroxy-2-[4-(1-hydroxy-2-methyl-propyl)-phenyl]-cyclopentyl}-heptanoic acid methyl ester (9—9);

7-{(1R,2S,3R,5R)-5-Chloro-3-hydroxy-2-[4-(1-hydroxy-2,2-dimethyl-propyl)-phenyl]-cyclopentyl}-heptanoic acid methyl ester (9-10);

7-{(1R,2S,3R,5R)-5-Chloro-3-hydroxy-2-[4-(1-hydroxy-2-methyl-propyl)-phenyl]-cyclopentyl}-heptanoic acid (9-11);

7-{(1R,2S,3R,5R)-5-Chloro-3-hydroxy-2-[4-(1-hydroxy-2,2-dimethyl-propyl)-phenyl]-cyclopentyl}-heptanoic acid (9-12);

(4-{(1R,2S,3R,5R)-5-Chloro-2-[4-(cyclohexyl-hydroxy-methyl)-phenyl]-3-hydroxy-cyclopentyl}-but-2-ynyloxy)-acetic acid methyl ester (10-6);

(4-{(1R,2S,3R,5R)-5-Chloro-2-[4-(cyclohexyl-hydroxy-methyl)-phenyl]-3-hydroxy-cyclopentyl}-but-2-ynyloxy)-acetic acid (10-7);

((Z)-4-{(1R,2S,3R,5R)-5-Chloro-2-[4-(cyclohexyl-hydroxy-methyl)-phenyl]-3-hydroxy-cyclopentyl}-but-2-enyloxy)-acetic acid methyl ester (11-1);

((Z)-4-{(1R,2S,3R,5R)-5-Chloro-2-[4-(cyclohexyl-hydroxy-methyl)-phenyl]-3-hydroxy-cyclopentyl}-but-2-enyloxy)-acetic acid (11-2);

(4-{(1R,2S,3R,5R)-5-Chloro-2-[4-(cyclohexyl-hydroxy-methyl)-phenyl]-3-hydroxy-cyclopentyl}-butoxy)-acetic acid methyl ester (11-3);

(4-{(1R,2S,3R,5R)-5-Chloro-2-[4-(cyclohexyl-hydroxy-methyl)-phenyl]-3-hydroxy-cyclopentyl}-butoxy)-acetic acid (11-4);

[3-((1R,2S,3R)-3-Hydroxy-2-{3-[(S)-hydroxy-(1-propyl-cyclobutyl)-methyl]-phenyl}-5-oxo-cyclopentylmethyl)-phenoxy]-acetic acid methyl ester (13-3);

[3-((1R,2S,3R)-3-Hydroxy-2-{3-[(S)-hydroxy-(1-propyl-cyclobutyl)-methyl]-phenyl}-5-oxo-cyclopentylmethyl)-phenoxy]-acetic acid (13-4);

[3-((1R,2S,3R,5R)-5-Chloro-3-hydroxy-2-{3-[(S)-hydroxy-(1-propyl-cyclobutyl)-methyl]-phenyl}-cyclopentylmethyl)-phenoxy]-acetic acid methyl ester (14-3);

[3-((1R,2S,3R,5R)-5-Chloro-3-hydroxy-2-{3-[(S)-hydroxy-(1-propyl-cyclobutyl)-methyl]-phenyl}-cyclopentylmethyl)-phenoxy]-acetic acid (14-4);

(Z)-7-[(1R,2S,3R)-3-Hydroxy-2-(1-hydroxy-indan-5-yl)-5-oxo-cyclopentyl]-hept-5-enoic acid methyl ester (15-6);

(Z)-7-[(1R,2S,3R)-3-Hydroxy-2-(1-hydroxy-indan-5-yl)-5-oxo-cyclopentyl]-hept-5-enoic acid (15-7);

(Z)-7-[(1R,2S,3R)-3-Hydroxy-5-oxo-2-(1-oxo-indan-5-yl)-cyclopentyl]-hept-5-enoic acid methyl ester (15-8);

(Z)-7-[(1R,2S,3R)-3-Hydroxy-5-oxo-2-(1-oxo-indan-5-yl)-cyclopentyl]-hept-5-enoic acid (15-9);

7-[(1R,2S,3R)-3-Hydroxy-2-(1-hydroxy-indan-5-yl)-5-oxo-cyclopentyl]-heptanoic acid methyl ester (15-10);

7-((1R,2S,3R)-3-Hydroxy-2-indan-5-yl-5-oxo-cyclopentyl)-heptanoic acid methyl ester (15-12);

7-[(1R,2S,3R)-3-Hydroxy-2-(1-hydroxy-indan-5-yl)-5-oxo-cyclopentyl]-heptanoic acid (15-11);

7-((1R,2S,3R)-3-Hydroxy-2-indan-5-yl-5-oxo-cyclopentyl)-heptanoic acid (15-13);

(Z)-7-[(1R,2S,3R,5R)-5-Chloro-3-hydroxy-2-(1-hydroxy-indan-5-yl)-cyclopentyl]-hept-5-enoic acid methyl ester (16-4);

(Z)-7-[(1R,2S,3R,5R)-5-Chloro-3-hydroxy-2-(1-hydroxy-indan-5-yl)-cyclopentyl]-hept-5-enoic acid (16-5);

(Z)-7-[(1R,2S,3R,5R)-5-Chloro-3-hydroxy-2-(1-hydroxy-indan-5-yl)-cyclopentyl]-hept-5-enoic acid isopropyl ester (16-6);

7-[(1R,2S,3R,5R)-5-Chloro-3-hydroxy-2-(1-hydroxy-indan-5-yl)-cyclopentyl]-heptanoic acid methyl ester (16-7);

7-((1R,2S,3R,5R)-5-Chloro-3-hydroxy-2-indan-5-yl-cyclopentyl)-heptanoic acid methyl ester (16-9);

7-[(1R,2S,3R,5R)-5-Chloro-3-hydroxy-2-(1-hydroxy-indan-5-yl)-cyclopentyl]-heptanoic acid (16-8);

7-((1R,2S,3R,5R)-5-Chloro-3-hydroxy-2-indan-5-yl-cyclopentyl)-heptanoic acid (16-10);

7-[(1R,2S,3R)-5-Fluoro-3-hydroxy-2-(1-hydroxy-indan-5-yl)-cyclopentyl]-heptanoic acid methyl ester (17-3);

7-[(1R,2S,3R)-5-Fluoro-3-hydroxy-2-(1-hydroxy-indan-5-yl)-cyclopentyl]-heptanoic acid (17-4);

(Z)-7-[(1R,2S,3R)-5-Fluoro-3-hydroxy-2-(1-hydroxy-indan-5-yl)-cyclopentyl]-hept-5-enoic acid methyl ester (17-5); or (Z)-7-[(1R,2S,3R)-5-Fluoro-3-hydroxy-2-(1-hydroxy-indan-5-yl)-cyclopentyl]-hept-5-enoic acid (17-6).

A prostaglandin $EP_2$ selective agonist is a compound which is more active at a prostaglandin $EP_2$ receptor than at any other prostaglandin receptor. In one embodiment, the compound has an $IC_{50}$ value less than 1 µM. In another embodiment, the compound is more than 100 times more active at the $EP_2$ receptor than at any other receptor. In another embodiment, the compound is more than 1000 times more active at the $EP_2$ receptor than at any other receptor.

The (ω-chain has the meaning normally understood in the art. In prostaglandin $E_2$, the (ω-chain is in the third position of the cyclopentanone ring, where the position 1 is the carbonyl and the α-chain is at position 2. However, the meaning of the term α-chain should be adapted according to synthetic variations that are made to prostaglandin $E_2$. A person of ordinary skill in the art can readily discern the ω-chain in synthetic analogs and derivatives of prostaglandin $E_2$. For example, while not intending to limit the scope of the invention in any way, the (ω-chain could be at the third position in a 1-chlorocyclopentane having the α-chain in the 2 position.

A substituted phenyl, wherein at least one substituent consists of hydrocarbyl or non-linear hydroxyhydrocarbyl may have additional substituents which are not hydrocarbyl or non-linear hydroxyhydrocarbyl, i.e. at least one substituent is hydrocarbyl or non-linear hydroxyhydrocarbyl and at least one substituent is not.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

EXAMPLE 1

1-Propyl-cyclobutanecarboxylic acid methyl ester (1-2). Ester 1—1 (2.043 g, 15.9 mmol) was added to a −78° C. solution of LDA (8 mL, 16 mmol, 2 M in heptane/THF/ethyl benzene) in THF (16 mL), rinsing with 1 mL THF. The reaction was stirred for 30 min. at −78° C. and then was allowed to warm to room temperature. The enolate solution was then added, by cannula, to a solution of n-propyl iodide (4.087 g, 24 mmol) in 8 mL DMSO. The internal temperature was maintained between 16–20° C. by cooling with an ice-bath. After 1 h, The solvent was removed and the residue diluted with $H_2O$ (150 mL). The resulting mixture was extracted with hexanes (2×120 mL) and the combined organic solution was washed with 2% HCl (100 mL) and brine (100 mL). The organic solution was then dried ($Na_2SO_4$), filtered and evaporated. The crude product was combined with the crude product from another reaction run (starting with 14.858 g, 116 mmol of 1—1) and the combined product was purified by simple distillation under reduced pressure to give 1-2 (9.744 g, 49%).

(1-Propyl-cyclobutyl)-methanol (1-3). $LiBH_4$ (524 mg, 24 mmol) and methanol (1 mL) were added to a 0° C. solution of 1-2 (1.935 g, 11.4 mmol) in ether (22 mL). After 1 h at 0° C. and 1.5 h at room temperature, 41 mL 2 M NaOH was slowly added and the resulting mixture was stirred for 1 h. The mixture was then extracted with dichloromethane (3×40 mL) and the combined dichloromethane solution was washed with saturated $NH_4Cl$ solution and brine (150 mL each). The organic solution was then dried ($Na_2SO_4$), filtered and evaporated. Purification by flash chromatography on silica gel (dichloromethane) gave 1-3 (1.229 g, 87%).

1-Propyl-cyclobutanecarbaldehyde (1-4). An ice-cold mixture of 4-methylmorpholine N-oxide (NMO) (1.683 g, 14.4 mmol), 1-3 (1.229 g, 9.59 mmol) and 4 Å molecular sieves (5.5 g) in dichloromethane (20 mL) was treated with tetrapropylammonium perruthenate (TPAP) (179 mg, 0.51 mmol). The mixture was stirred at 0° C. for 5 min. and then was allowed to warm to room temperature. After 1 h, the mixture was filtered through a pad of silica gel (dichloromethane) and the dichloromethane was evaporated. The crude product was combined with the crude product from another batch (starting with 4.986 g, 38.9 mmol of 1-3) and the combined product was purified by distillation under reduced pressure followed by flash chromatography on silica gel (15% ether/pentane) to give 1-4 (2.649 g, 43%).

2-(4-Bromo-phenyl)-2-methyl-propan-1-ol (2—2). $LiBH_4$ (387 mg, 17.8 mmol) and methanol (0.75 mL) were added to a 0° C. solution of 2-1 (2.07 g, 8.05 mmol) in ether (75 mL). After 30 min. at 0° C. and 1.5 h at room temperature, the reaction was quenched by slow addition of 40 mL 2 M NaOH. The layers were separated and the aqueous layer was further extracted with dichloromethane (3×40 mL). The combined organic solution was washed with brine and then was dried ($Na_2SO_4$), filtered and evaporated. Purification by flash chromatography on silica gel (20% ethyl acetate/hexanes) gave 2—2 (1.780 g, 97%).

[2-(4-Bromo-phenyl)-2-methyl-propoxy]-tert-butyl-dimethyl-silane (2-3). TBSOTf (2.9 mL, 12.6 mmol) was added to a 0° C. solution of 2—2 (1.893 g, 8.26 mmol) and 2,6-lutidine (2.9 mL, 24.9 mmol) in dichloromethane (24 mL). The reaction was allowed to warm to room temperature and after 1 h, 50 mL saturated $NaHCO_3$ solution was added. The resulting mixture was extracted with ethyl acetate (3×60 mL) and the combined ethyl acetate solution was washed with brine. The solution was then dried ($Na_2SO_4$), filtered and evaporated. Purification by flash chromatography on silica gel (hexanes) gave 2-3 (2.767 g, 98%).

1-(4-Bromo-phenyl)-cyclobutanol (3-1). n-Butyllithium (1.2 mL 1.92 mmol, 1.6 M/hexanes) was added to a −78° C. solution of 1,4-dibromobenzene (489 mg, 2.07 mmol) in THF (4.2 mL). After 30 min., a solution of cyclobutanone (141 mg, 2.01 mmol) in 1 mL THF was added by cannula, rinsing with 0.5 mL THF. The reaction was allowed to warm to room temperature and after 2 h, saturated $NH_4Cl$ solution was added. The resulting mixture was extracted with ethyl acetate (3×30 mL) and the combined ethyl acetate solution was washed with brine. The solution was then dried ($Na_2SO_4$), filtered and evaporated. Purification by flash chromatography on silica gel (5%→10% ethyl acetate/hexanes) gave 3-1 (235 mg, 54%).

[1-(4-Bromo-phenyl)-cyclobutoxy]-tert-butyl-dimethyl-silane (3-2). TBSOTf (360 µL, 1.57 mmol) was added to a 0° C. solution of 3-1 (235 mg, 1.04 mmol) and triethylamine (450 µL, 3.23 mmol) in dichloromethane (3 mL). The reaction was allowed to warm to room temperature and after 1 h, saturated $NaHCO_3$ solution was added. The resulting mixture was extracted with ethyl acetate (3×30 mL) and the combined ethyl acetate solution was washed with brine. The solution was then dried ($Na_2SO_4$), filtered and evaporated. Purification by flash chromatography on silica gel (hexanes) gave 3-2 (329 mg, 93%).

Representative procedure for reaction of dibromobenzene with aldehydes: (4-Bromo-phenyl)-cyclohexyl-methanol (4-2, R=cyclohexyl, para substitution)-. n-BuLi (14.4 mL, 23 mmol) was added to a −78° C. solution of 1,4-dibromobenzene (5.442 g, 23.1 mmol) in THF (48 mL). The resulting mixture was stirred for 30 min. and then a solution of cyclohexanecarboxaldehyde (2.9 mL, 24.1 mmol) in THF (10 mL) was added by cannula. The resulting cloudy solution was allowed to warm to room temperature and was stirred further for 2 h. Saturated NH$_4$Cl solution (200 mL) was then added and the mixture was extracted with ethyl acetate (3×100 mL). The combined ethyl acetate solution was washed with brine (150 mL) and then was dried (Na$_2$SO$_4$), filtered and evaporated. Purification by flash chromatography on silica gel (10% ethyl acetate/hexanes→15%→20%) gave the title alcohol (5.095 g, 18.9 mmol, 82%).

Representative procedure for TBS protection of bottom chain alcohols: [(4-Bromo-phenyl)-cyclohexyl-methoxy]-tert-butyl-dimethyl-silane (4-3, R=cyclohexyl, para substitution). An ice-cold solution of 4-2 (5.095 g, 18.9 mmol) was treated with 2,6-lutidine (2.9 mL, 24.9 mmol) and TBSOTf (5.2 mL, 22.6 mmol). After 2 h, 100 mL saturated NaHCO$_3$ solution was added and the resulting mixture was extracted with 50 mL dichloromethane. The dichloromethane solution was washed with 1 M HCl (100 mL) and 100 mL brine and then was dried (Na$_2$SO$_4$), filtered and evaporated. Purification by flash chromatography on silica gel gave the title TBS ether (6.772 g, 17.7 mmol, 94%).

[(4-Bromo-phenyl)-(1-propyl-cyclobutyl)-methoxy]-tert-butyl-dimethyl-silane (4-3, R=1-propylcyclobutyl, para substitution). This compound was prepared using the representative sequence (FIG. 4), starting with 1,4-dibromobenzene and aldehyde 1-4.

[(3-Bromo-phenyl)-(1-propyl-cyclobutyl)-methoxy]-tert-butyl-dimethyl-silane (4-3, R=1-propylcyclobutyl, meta substitution). This compound was prepared using the representative sequence (FIG. 4), starting with 1,3-dibromobenzene and aldehyde 1-4.

Representative procedure for 2-component coupling: (Z)-7-((1R,2S,3R)-3-(tert-Butyl-dimethyl-silanyloxy)-2-{4-[(tert-butyl-dimethyl-silanyloxy)-cyclohexyl-methyl]-phenyl}-5-oxo-cyclopentyl)-hept-5-enoic acid methyl ester (5-3). n-BuLi (1.1 mL, 1.76 mmol, 1.6 M/hexanes) was added to a −78° C. solution of thiophene (195 mg, 2.32 mmol) in ether (2 mL). The reaction was allowed to stir at 0° C. for 1 h and then was recooled to −78° C. The resulting solution of the lithio thiophene was cannula transferred to a mixture of CuCN (226 mg) in ether (2 mL). The resulting suspension was allowed to stir at room temperature for 30 min. and at −78° C. for 30 min.

In another flask, t-BuLi (2.3 mL, 3.91 mmol) was added to a −78° C. solution of 5-1 (747 mg, 1.95 mmol) in ether (2 mL). The suspension was stirred for 1 h and then cannula transferred to the lithium 2-thienylcyanocuprate mixture, rinsing with 1 mL ether. The resulting mixture was stirred for 15 min. at 0° C. and then was recooled to −78° C. A solution of enone 5-2 (578 mg, 1.64 mmol, obtained from Nissan Chemical Industries, LTD, Chemicals Division 3-7-1 Kanda-Nishiki-cho, Chiyoda-ku, Tokyo 101-0054, Japan) in ether (2 mL) was then added by cannula, rinsing with 1 mL ether. The reaction was stirred for 1 h at −78° C., 1 h at 0° C. and for 15 min. at room temperature.

The reaction was then quenched by addition of a 10% solution of concentrated NH$_4$OH in saturated NH$_4$Cl. The resulting mixture was extracted with ethyl acetate (3×) and the combined ethyl acetate solution was washed with brine. The organic solution was dried (Na$_2$ SO$_4$), filtered and evaporated. Purification by flash chromatography on silica gel (4% ethyl acetate/hexanes→5%) gave the title ketone (760 mg, 71%).

Representative prodecure for TBS deprotection with HF-pyridine: (Z)-7-{(1R,2S,3R)-2-[4-(Cyclohexyl-hydroxy-methyl)-phenyl]-3-hydroxy-5-oxo-cyclopentyl}-hept-5-enoic acid methyl ester (5-4). HF-pyridine (1.8 mL) was added to an ice-cold CH$_3$CN (9 mL) solution of 5-3 (196 mg, 0.30 mmol). The reaction was stirred for 1 h and then was quenched by addition of saturated NaHCO$_3$ solution. The resulting mixture was extracted with dichloromethane and the combined dichloromethane solution was dried (Na$_2$SO$_4$), filtered and evaporated. Purification by flash chromatography on silica gel (50% ethyl acetate/hexanes) gave the title diol 5-4 (117 mg, 91%).

Representative procedure for hydrolysis of methyl esters with rabbit liver esterase: (Z)-7-{(1R,2S,3R)-2-[4-(Cyclohexyl-hydroxy-methyl)-phenyl]-3-hydroxy-5-oxo-cyclopentyl}-hept-5-enoic acid (5—5). A mixture of 5-4 (46 mg, 0.11 mmol) and rabbit liver esterase (8 mg) in CH$_3$CN (0.45 mL)/pH 7.2 phosphate buffer (9 mL) was stirred overnight. The mixture was co-evaporated with CH$_3$CN and the residue purified by flash chromatography on silica gel (5% methanol/dichloromethane) to give the title acid 5—5 (36 mg, 80%). 300 MHz $^1$H NMR (CDCl$_3$, ppm) δ 7.3–7.1 (4H, m) 5.3–5.2 (2H, m) 5.5–4.5 (3H, broad s) 4.4–4.3 (2H, m) 3.0–2.7 (2H, m) 2.6–0.8 (21H, overlapping m).

Representative procedure for hydrogenation of the top chain: 7-{(1R,2S,3R)-2-[4-(Cyclohexyl-hydroxy-methyl)-phenyl]-3-hydroxy-5-oxo-cyclopentyl}-heptanoic acid methyl ester (5-7). A mixture of ester 5-4 (67 mg, 0.16 mmol) and 5% Pd/C (49 mg) in methanol (12 mL) was stirred under 1 atm H$_2$ for 4 h. The mixture was filtered through celite and the solvent evaporated. Purification by flash chromatography on silica gel (50% ethyl acetate/hexanes) gave the title ester (15 mg, 22%).

7-{(1R,2S,3R)-2-[4-(Cyclohexyl-hydroxy-methyl)-phenyl]-3-hydroxy-5-oxo-cyclopentyl}-heptanoic acid (5-8). The representative procedure using rabbit liver esterase was followed.

(Z)-7-((1R,2S,3R)-3-Hydroxy-2-{4-[hydroxy-(1-propyl-cyclobutyl)-methyl]-phenyl}-5-oxo-cyclopentyl)-hept-5-enoic acid methyl ester. A sequence analogous to the one used to prepare 5-4 (FIGS. 4,5) was followed, starting from [(4-Bromo-phenyl)-(1-propyl-cyclobutyl)-methoxy]-tert-butyl-dimethyl-silane (4-3).

(Z)-7-((1R,2S,3R)-3-Hydroxy-2-{4-[hydroxy-(1-propyl-cyclobutyl)-methyl]-phenyl}-5-oxo-cyclopentyl)-hept-5-enoic acid. The representative procedure using rabbit liver esterase was followed, starting from the corresponding methyl ester.

7-((1R,2S,3R)-3-Hydroxy-2-{4-[hydroxy-(1-propyl-cyclobutyl)-methyl]-phenyl}-5-oxo-cyclopentyl)-heptanoic acid methyl ester. A sequence analogous to the one used to prepare 5-7 (FIG. 5) was followed.

7-((1R,2S,3R)-3-Hydroxy-2-{4-[hydroxy-(1-propyl-cyclobutyl)-methyl]-phenyl}-5-oxo-cyclopentyl)-heptanoic acid. The representative procedure using rabbit liver esterase was followed, starting from the corresponding methyl ester.

(Z)-7-[(1R,2S,3R)-2-(4-tert-Butyl-phenyl)-3-hydroxy-5-oxo-cyclopentyl]-hept-5-enoic acid methyl ester. A sequence analogous to the one used to prepare 5-4 (FIG. 5) was followed, starting from 1-bromo-4-tert-butylbenzene in the place of 5-1.

(Z)-7-[(1R,2S,3R)-2-(4-tert-Butyl-phenyl)-3-hydroxy-5-oxo-cyclopentyl]-hept-5-enoic acid. The representative procedure using rabbit liver esterase was followed, starting from the corresponding methyl ester.

7-[(1R,2S,3R)-2-(4-tert-Butyl-phenyl)-3-hydroxy-5-oxo-cyclopentyl]-heptanoic acid methyl ester. The representative hydrogenation procedure was followed.

7-[(1R,2S,3R)-2-(4-tert-Butyl-phenyl)-3-hydroxy-5-oxo-cyclopentyl]-heptanoic acid. The representative procedure using rabbit liver esterase was followed, starting from the corresponding methyl ester.

(Z)-7-{(1R,2S,3R)-3-Hydroxy-2-[4-(2-hydroxy-1,1-dimethyl-ethyl)-phenyl]-5-oxo-cyclopentyl}-hept-5-enoic acid methyl ester. A sequence analogous to the one used to prepare 5-4 (FIGS. 2, 5) was followed, starting with 2-3 instead of 5-1.

(Z)-7-{(1R,2S,3R)-3-Hydroxy-2-[4-(2-hydroxy-1,1-dimethyl-ethyl)-phenyl]-5-oxo-cyclopentyl}-hept-5-enoic acid. The representative procedure using rabbit liver esterase was followed, starting from the corresponding methyl ester.

7-{(1R,2S,3R)-3-Hydroxy-2-[4-(2-hydroxy-1,1-dimethyl-ethyl)-phenyl]-5-oxo-cyclopentyl}-heptanoic acid methyl ester. The representative hydrogenation procedure was followed, using ethyl acetate as solvent and stirring overnight.

7-{(1R,2S,3R)-3-Hydroxy-2-[4-(2-hydroxy-1,1-dimethyl-ethyl)-phenyl]-5-oxo-cyclopentyl}-heptanoic acid. The representative procedure using rabbit liver esterase was followed, starting from the corresponding methyl ester.

(Z)-7-{(1R,2S,3R)-3-Hydroxy-2-[4-(1-hydroxy-cyclobutyl)-phenyl]-5-oxo-cyclopentyl}-hept-5-enoic acid methyl ester (e1-2). A sequence analogous to the one used to prepare 5-4 was followed [starting from 3-2 instead of 5-1 (FIGS. 3, 5)] with the exception of the TBS deprotection step, which was done using the following procedure (see equation 1): A mixture of e1-1 (46 mg, 0.075 mmol) in AcOH/$H_2O$/THF 3:1:1 (0.6 mL) was allowed to stir at room temperature. After 2 days, saturated $NaHCO_3$ solution was added and the resulting mixture was extracted with dichloromethane (3×25 mL). The combined dichloromethane solution was dried ($Na_2SO_4$), filtered and evaporated. Purification by flash chromatography on silica gel (50% ethyl acetate/hexanes) gave the title diol e1-2 (6 mg, 21%).

(Z)-7-{(1R,2S,3R)-3-Hydroxy-2-[4-(1-hydroxy-cyclobutyl)-phenyl]-5-oxo-cyclopentyl}-hept-5-enoic acid. The representative procedure using rabbit liver esterase was followed, starting with e1-2.

7-{(1R,2S,3R)-3-Hydroxy-2-[4-(1-hydroxy-cyclobutyl)-phenyl]-5-oxo-cyclopentyl}-heptanoic acid methyl ester. The representative hydrogenation procedure was followed, using ethyl acetate as solvent and stirring overnight.

7-{(1R,2S,3R)-3-Hydroxy-2-[4-(1-hydroxy-cyclobutyl)-phenyl]-5-oxo-cyclopentyl}-heptanoic acid. The representative procedure using rabbit liver esterase was followed, starting from the corresponding methyl ester.

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid methyl ester. A sequence analogous to the one used to prepare 5-4 (FIGS. 4,5) was followed, starting from [(3-Bromo-phenyl)-(1-propyl-cyclobutyl)-methoxy]-tert-butyl-dimethyl-silane (4-3).

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid (e2-1). The representative procedure using rabbit liver esterase was followed, starting from the corresponding methyl ester.

7-((1R,2S,3R)-3-Hydroxy-2-{3-[hydroxy-(1-propyl-cyclobutyl)-methyl]-phenyl}-5-oxo-cyclopentyl)-heptanoic acid methyl ester. The representative hydrogenation procedure was used.

7-((1R,2S,3R)-3-Hydroxy-2-{3-[hydroxy-(1-propyl-cyclobutyl)-methyl]-phenyl}-5-oxo-cyclopentyl)-heptanoic acid. The representative procedure using rabbit liver esterase was followed, starting from the corresponding methyl ester.

Representative procedure for secondary amide formation: (Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid (2-hydroxy-ethyl)-amide (e2-2, R=2-hydroxyethyl, equation 2). DMF (0.5 mL) and N-hydroxysuccinimide (12 mg, 0.10 mmol) were added to acid e2-1 (8 mg, 0.02 mmol). The mixture was stirred for 5 min. and 1-(3-dimethylaminopropyl)-3-ethylcarbodiimide hydrochloride (EDCI) (39 mg, 0.20 mmol) was added. This mixture was stirred for 4 h at room temperature and 2-aminoethanol (6 μL, 0.10 mmol) was added. After stirring overnight, the reaction was diluted with ethyl acetate and the resulting mixture was washed with $H_2O$ (3×15 mL) and brine. The organic solution was then dried ($Na_2SO_4$), filtered and evaporated. Purification of the residue by flash chromatography on silica gel (5%→7% methanol/dichloromethane) gave the title amide (5.4 mg, 63%).

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid ethyl amide (e2-2, R=ethyl). A procedure analogous to the one used above was followed.

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid ethyl amide (e2-2, R=H). Dichloromethane (0.2 mL) and triethylamine (15 μL, 0.11 mmol) were added to e2-1 (8 mg, 0.02 mmol). The reaction was stirred for 10 min., cooled in an ice bath and ethyl chloroformate (7 μL, 0.073 mmol) was added. After 1 h at 0° C., concentrated $NH_4OH_{aq}$ (10 μL, 0.26 mmol) was added. The reaction was stirred overnight at room temperature and then 0.5 M HCl (5 mL) was added. The resulting mixture was extracted with ethyl acetate (3×25 μL) and the combined ethyl acetate solution was washed with saturated $NaHCO_3$ solution and brine. The solution was then dried ($Na_2SO_4$), filtered and evaporated. Purification of the residue by flash chromatography on silica gel (5% methanol/dichloromethane) gave the title amide (2.2 mg, 28%).

Representative procedure for reduction of the C9 ketone: (Z)-7-((1R,2S,3R,5S)-3-(tert-Butyl-dimethyl-silanyloxy)-2-{4-[(tert-butyl-dimethyl-silanyloxy)-cyclohexyl-methyl]-phenyl}-5-hydroxy-cyclopentyl)-hept-5-enoic acid methyl ester (6-1). L-selectride (300 μL, 0.3 mmol, 1 M/THF) was added to a −78° C. solution of ketone 5-3 (159 mg, 0.24 mmol) in 12 mL THF. The reaction was stirred for 30 min. at −78° C. and then 3% $H_2O_2$ (7 mL) was added. The reaction was stirred for 2 h at room temperature and then was poured into saturated $NH_4Cl$ solution. The mixture was extracted with ethyl acetate (3×50 mL) and the combined ethyl acetate solution was washed with brine and then was dried ($Na_2SO_4$), filtered and evaporated. Purification by flash chromatography on silica gel (8% ethyl acetate/hexanes) gave the title alcohol (149 mg, 93%).

Representative procedure for conversion of the C9 alcohol to the C9 chloride: (Z)-7-((1R,2S,3R,5R)-3-(tert-Butyl-dimethyl-silanyloxy)-2-{4-[(tert-butyl-dimethyl-silanyloxy)-cyclohexyl-methyl]-phenyl}-5-chloro-cyclopentyl)-hept-5-enoic acid methyl ester (6-2). MsCl (125 μL, 1.62 mmol) was added to a solution of 6-1 (117 mg, 0.18 mmol) and triethylamine (250 μL, 1.79 mmol) in 1,2-dichloroethane (0.5 mL). The reaction was stirred for 3 h and then was quenched by addition of saturated $NaHCO_3$. The mixture was extracted with dichloromethane (3×40 mL) and the combined dichloromethane solution was dried (Na$_2$SO$_4$), filtered and evaporated to give the crude mesylate (196 mg).

A mixture of the crude mesylate and (n-Bu)$_4$NCl (214 mg, 0.077 mmol) in toluene (1.8 mL) was stirred at 40° C. overnight. The mixture was then filtered through silica gel, washing with ethyl acetate and the ethyl acetate evaporated. The residue was purified by flash chromatography on silica gel to give the title chloride 6-2 (24 mg, 20%) along with a mono TBS containing compound (36 mg, 36%).

(Z)-7-{(1R,2S,3R,5R)-5-Chloro-2-[4-(cyclohexyl-hydroxy-methyl)-phenyl]-3-hydroxy-cyclopentyl}-hept-5-enoic acid methyl ester (6-3). HF-pyridine (0.60 mL) was added to a 0° C. CH$_3$CN solution of chloride 6-2 (24 mg, 20%) and the mono TBS derivative (36 mg, 36%). The reaction was stirred for 1 h, and then was quenched by addition of saturated NaHCO$_3$ solution. The mixture was extracted with dichloromethane (3×30 mL) and the combined dichloromethane solution dried (Na$_2$SO$_4$), filtered and evaporated. Purification by flash chromatography on silica gel (20% ethyl acetate/hexanes) gave the title diol 6-3 (37 mg, 93%).

Representative procedure for hydrolysis of the C1 methyl ester with LiOH: (Z)-7-{(1R,2S,3R,5R)-5-Chloro-2-[4-(cyclohexyl-hydroxy-methyl)-phenyl]-3-hydroxy-cyclopentyl}-hept-5-enoic acid (6-4). Aqueous LiOH (0.75 mL, 0.75 mmol, 1 M) was added to a solution of ester 6-3 (32 mg, 0.07 mmol) in THF (4 mL). The reaction was stirred overnight and then 1 M HCl was added. The resulting mixture was extracted with dichloromethane and the combined dichloromethane solution was dried (Na$_2$SO$_4$), filtered and evaporated. Purification by flash chromatography on silica gel (3% methanol/dichloromethane) followed by preparative thin layer chromatography (5% methanol/dichloromethane) gave the title acid (26 mg, 83%). 300 MHz $^1$H NMR (CDCL$_3$, ppm) δ 7.3–7.2 (4H, m) 5.41–5.35 (2H, m) 4.42–4.36 (1H, m) 4.34 (1H, d, J=7.3 Hz) 4.2–4.1 (1H, m) 2.7–0.8 (23H, overlapping m's).

(Z)-7-{(1R,2S,3R,5R)-5-Chloro-2-[4-(cyclohexyl-hydroxy-methyl)-phenyl]-3-hydroxy-cyclopentyl}-hept-5-enoic acid isopropyl ester (6-5). A procedure analogous to the one used to prepare 16-6 was followed.

7-{(1R,2S,3R,5R)-5-Chloro-2-[4-(cyclohexyl-hydroxymethyl)-phenyl]-3-hydroxy-cyclopentyl}-heptanoic acid methyl ester (6—6) and 7-[(1R,2S,3R,5R)-5-Chloro-2-(4-cyclohexylmethyl-phenyl)-3-hydroxy-cyclopentyl]-heptanoic acid methyl ester (6-8). The representative hydrogenation procedure was used, starting with 6-3 (52 mg, 0.12 mmol), 5% Pd/C (32 mg) in 6 mL methanol. Purification by flash chromatography on silica gel (50% ethyl acetate/hexanes) gave 6—6 (18 mg, 35%) and deoxygenated product 6-8 (27 mg, 52%).

7-{(1R,2S,3R,5R)-5-Chloro-2-[4-(cyclohexyl-hydroxymethyl)-phenyl]-3-hydroxy-cyclopentyl}-heptanoic acid (6-7). The representative LiOH procedure was used.

7-[(1R,2S,3R,5R)-5-Chloro-2-(4-cyclohexylmethyl-phenyl)-3-hydroxy-cyclopentyl]-heptanoic acid (6-9). The representative LiOH procedure was used.

(Z)-7-((1R,2S,3R,5R)-5-Chloro-3-hydroxy-2-{3-[hydroxy-(1-propyl-cyclobutyl)-methyl]-phenyl}-cyclopentyl)-hept-5-enoic acid methyl ester. A sequence analogous to the one used to prepare 6-3 (FIG. 6) was followed.

(Z)-7-((1R,2S,3R,5R)-5-Chloro-3-hydroxy-2-{3-[hydroxy-(1-propyl-cyclobutyl)-methyl]-phenyl}-cyclopentyl)-hept-5-enoic acid. The representative LiOH procedure was used, starting with the corresponding methyl ester.

7-((1R,2S,3R,5R)-5-Chloro-3-hydroxy-2-{3-[hydroxy-(1-propyl-cyclobutyl)-methyl]-phenyl}-cyclopentyl)-heptanoic acid methyl ester. A sequence analogous to the one used to prepare 6—6 (FIG. 6) was followed.

7-((1R,2S,3R,5R)-5-Chloro-3-hydroxy-2-{3-[hydroxy-(1-propyl-cyclobutyl)-methyl]-phenyl}-cyclopentyl)-heptanoic acid. The representative LiOH procedure was used, starting with the corresponding methyl ester.

(Z)-7-((1R,2S,3R,5R)-5-Chloro-3-hydroxy-2-{4-[hydroxy-(1-propyl-cyclobutyl)-methyl]-phenyl}-cyclopentyl)-hept-5-enoic acid methyl ester. A sequence analogous to the one used to prepare 6-3 (FIG. 6) was followed.

(Z)-7-((1R,2S,3R,5R)-5-Chloro-3-hydroxy-2-{4-[hydroxy-(1-propyl-cyclobutyl)-methyl]-phenyl}-cyclopentyl)-hept-5-enoic acid. The representative LiOH procedure was used, starting with the corresponding methyl ester.

7-((1R,2S,3R,5R)-5-chloro-3-hydroxy-2-{4-[hydroxy-(1-propyl-cyclobutyl)-methyl]-phenyl)-cyclopentyl}-heptanoic acid methyl ester. A sequence analogous to the one used to prepare 6—6 (FIG. 6) was followed.

7-((1R,2S,3R,5R)-5-Chloro-3-hydroxy-2-{4-[hydroxy-(1-propyl-cyclobutyl)-methyl]-phenyl}-cyclopentyl)-heptanoic acid. The representative LiOH procedure was used, starting with the corresponding methyl ester.

(Z)-7-[(1R,2S,3R,5R)-2-(4-tert-Butyl-phenyl)-5-chloro-3-hydroxy-cyclopentyl]-hept-5-enoic acid methyl ester. A sequence analogous to the one used to prepare 6-3 (FIG. 6) was followed.

(Z)-7-[(1R,2S,3R,5R)-2-(4-tert-Butyl-phenyl)-5-chloro-3-hydroxy-cyclopentyl]-hept-5-enoic acid. The representative LiOH procedure was used, starting with the corresponding methyl ester.

7-[(1R,2S,3R,5R)-2-(4-tert-Butyl-phenyl)-5-chloro-3-hydroxy-cyclopentyl]-heptanoic acid methyl ester. The representative hydrogenation procedure was followed, stirring the reaction overnight.

7-[(1R,2S,3R,5R)-2-(4-tert-Butyl-phenyl)-5-chloro-3-hydroxy-cyclopentyl]-heptanoic acid. The representative LiOH procedure was used, starting with the corresponding methyl ester.

(Z)-7-[(1R,2S,3R,5R)-2-(4-tert-Butyl-phenyl)-5-chloro-3-hydroxy-cyclopentyl]-hept-5-enoic acid isopropyl ester. A procedure analogous to the one used to prepare 16-6 was followed.

(Z)-7-{(1R,2S,3R,5R)-5-Chloro-3-hydroxy-2-[4-(1-hydroxy-cyclobutyl)-phenyl]-cyclopentyl}-hept-5-enoic acid methyl ester. A sequence analogous to the one used to prepare 6-3 was followed with the exception of the TBS deprotection step, which was done using a procedure analogous to the one used to prepare e1-2.

(Z)-7-{(1R,2S,3R,5R)-5-Chloro-3-hydroxy-2-[4-(1-hydroxy-cyclobutyl)-phenyl]-cyclopentyl}-hept-5-enoic acid. The representative LiOH procedure was used, starting with the corresponding methyl ester.

7-{(1R,2S,3R,5R)-5-Chloro-3-hydroxy-2-[4-(1-hydroxy-cyclobutyl)-phenyl]-cyclopentyl)-heptanoic acid methyl ester. The representative hydrogenation procedure was followed, using ethyl acetate as solvent and stirring overnight.

7-{(1R,2S,3R,5R)-5-Chloro-3-hydroxy-2-[4-(1-hydroxy-cyclobutyl)-phenyl]-cyclopentyl}-heptanoic acid. The representative LiOH procedure was used, starting with the corresponding methyl ester.

(Z)-7-{(1R,2S,3R,5R)-5-Chloro-3-hydroxy-2-[4-(2-hydroxy-1,1-dimethyl-ethyl)-phenyl]-cyclopentyl}-hept-5-enoic acid methyl ester. A sequence analogous to the one used to prepare 6-3 (FIGS. 2,5,6) was followed, starting from 2-3 instead of 5-1.

(Z)-7-{(1R,2S,3R,5R)-5-Chloro-3-hydroxy-2-[4-(2-hydroxy-1,1-dimethyl-ethyl)-phenyl]-cyclopentyl}-hept-5- enoic acid. The representative LiOH procedure was used, starting with the corresponding methyl ester.

7-{(1R,2S,3R,5R)-5-Chloro-3-hydroxy-2-[4-(2-hydroxy-1,1-dimethyl-ethyl)-phenyl]-cyclopentyl}-heptanoic acid methyl ester. The representative hydrogenation procedure was followed, using ethyl acetate as solvent and stirring overnight.

7-{(1R,2S,3R,5R)-5-Chloro-3-hydroxy-2-[4-(2-hydroxy-1,1-dimethyl-ethyl)-phenyl]-cyclopentyl}-heptanoic acid. The representative LiOH procedure was used, starting with the corresponding methyl ester.

7-{(1R,2S,3R,5R)-5-Chloro-3-hydroxy-2-[4-(2-hydroxy-1,1-dimethyl-ethyl)-phenyl]-cyclopentyl}-heptanoic acid isopropyl ester. A procedure analogous to the one used to prepare 16-6 was followed, starting from the corresponding acid.

4-Bromobenzyl (4-methoxybenzyl) ether (7-2). A solution of 4-bromobenzyl alcohol (2.011 g, 10.7 mmol) in THF (42 mL) was added to a mixture of NaH (663 mg, 16.6 mmol, 60% in oil) in DMF (13 mL). The mixture was stirred for 1.5 h and 4-methoxybenzyl chloride (MPMCl, 2 mL, 14.8 mmol) was added. After 24 h, 100 mL saturated NH$_4$Cl solution was added. The resulting mixture was extracted with ethyl acetate (3×60 mL) and the combined ethyl acetate solution was washed with water and brine. The solution was then dried (Na$_2$SO$_4$), filtered and evaporated. Purification of the residue by flash chromatography on silica gel (5% ethyl acetate/hexanes) gave 7-2 (2.43 g, 98%).

(Z)-7-{(1R,2S,3R)-3-(tert-Butyl-dimethyl-silanyloxy)-2-[4-(4-methoxy-benzyloxymethyl)-phenyl]-5-oxo-cyclopentyl}-hept-5-enoic acid methyl ester (7-3). The representative 2-component-coupling procedure, as described for 5-3, was followed and resulted in 7-3 (1.548 g, 73%).

Representative procedure for DDQ deprotection of MPM ethers: (Z)-7-[(1R,2S,3R)-3-(tert-Butyl-dimethyl-silanyloxy)-2-(4-hydroxymethyl-phenyl)-5-oxo-cyclopentyl]-hept-5-enoic acid methyl ester (7-4): DDQ (24 mg, 0.10 mmol) was added to a mixture of 7-3 (47 mg, 0.08 mmol) in dichloromethane (1.6 mL)/H$_2$O (80 μL). After 1.5 h, 10 mL saturated NaHCO$_3$ solution was added. The resulting mixture was extracted with ethyl acetate (3×30 mL) and the combined ethyl acetate solution was washed with brine. The solution was then dried (Na$_2$SO$_4$), filtered and evaporated. Purification by flash chromatography on silica gel (25% ethyl acetate/hexanes) gave 7-4 (25 mg, 67%).

(Z)-7-[(1R,2S,3R)-3-Hydroxy-2-(4-hydroxymethyl-phenyl)-5-oxo-cyclopentyl]-hept-5-enoic acid methyl ester (7-5). The representative HF-pyridine deprotection procedure was used to give 7-5 (165 mg, 65%).

(Z)-7-[(1R,2S,3R)-3-Hydroxy-2-(4-hydroxymethyl-phenyl)-5-oxo-cyclopentyl]-hept-5-enoic acid (7-6). The representative rabbit liver esterase procedure was used.

7-[(1R,2S,3R)-3-Hydroxy-2-(4-hydroxymethyl-phenyl)-5-oxo-cyclopentyl]-heptanoic acid methyl ester (7—7). A mixture of 7-5 (17 mg, 0.05 mmol) and Wilkinson's catalyst (12 mg, 0.01 mmol) in 1 mL THF was stirred for 5 h under 1 atm H$_2$ (balloon). The mixture was then filtered through Celite and the volatiles evaporated. Purification of the residue by flash chromatography on silica gel (65% ethyl acetate/hexanes) gave 7—7 (11 mg, 62%).

7-((1R,2S,3R)-3-Hydroxy-5-oxo-2-p-tolyl-cyclopentyl)-heptanoic acid methyl ester (7-9). The representative H$_2$, Pd/C procedure was used, replacing methanol with ethyl acetate as solvent and stirring overnight. This afforded 7-9 (43 mg, 79%).

7-[(1R,2S,3R)-3-Hydroxy-2-(4-hydroxymethyl-phenyl)-5-oxo-cyclopentyl]-heptanoic acid (7-8). The representative rabbit liver esterase procedure was used.

7-((1R,2S,3R)-3-Hydroxy-5-oxo-2-p-tolyl-cyclopentyl)-heptanoic acid (7-10). The representative rabbit liver esterase procedure was used.

(Z)-7-{(1R,2S,3R,5S)-3-(tert-Butyl-dimethyl-silanyloxy)-5-hydroxy-2-[4-(4-methoxy-benzyloxymethyl)-phenyl]-cyclopentyl}-hept-5-enoic acid methyl ester (8-1). The representative L-selectride procedure was used.

(Z)-7-{(1R,2S,3R,5R)-3-(tert-Butyl-dimethyl-silanyloxy)-5-chloro-2-[4-(4-methoxy-benzyloxymethyl)-phenyl]-cyclopentyl}-hept-5-enoic acid methyl ester (8-2) and (Z)-7-{(1R,2S,3R,5R)-5-Chloro-3-hydroxy-2-[4-(4-methoxy-benzyloxymethyl)-phenyl]-cyclopentyl}-hept-5-enoic acid methyl ester (8-3). The representative procedure was used which gave 8-2 (365 mg, 39%) and 8-3 (290 mg, 38%).

(Z)-7-[(1R,2S,3R,5R)-5-Chloro-3-hydroxy-2-(4-hydroxymethyl-phenyl)-cyclopentyl]-hept-5-enoic acid methyl ester (8-4). The representative DDQ procedure was used resulting in 8-4 (184 mg, 84%).

(Z)-7-[(1R,2S,3R,5R)-5-Chloro-3-hydroxy-2-(4-hydroxymethyl-phenyl)-cyclopentyl]-hept-5-enoic acid (8-5). The representative LiOH hydrolysis procedure was used.

7-[(1R,2S,3R,5R)-5-Chloro-3-hydroxy-2-(4-hydroxymethyl-phenyl)-cyclopentyl]-heptanoic acid methyl ester (8-6). The representative H$_2$, Pd/C procedure was followed using ethyl acetate as solvent.

7-[(1R,2S,3R,5R)-5-Chloro-3-hydroxy-2-(4-hydroxymethyl-phenyl)-cyclopentyl]-heptanoic acid (8-7). The representative LiOH hydrolysis procedure was used.

(Z)-7-[(1R,2S,3R,5R)-3-(tert-Butyl-dimethyl-silanyloxy)-5-chloro-2-(4-hydroxymethyl-phenyl)-cyclopentyl]-hept-5-enoic acid methyl ester (9-1). The representative DDQ procedure was used.

(Z)-7-[(1R,2S,3R,5R)-3-(tert-Butyl-dimethyl-silanyloxy)-5-chloro-2-(4-formyl-phenyl)-cyclopentyl]-hept-5-enoic acid methyl ester (9-2). An ice cold mixture of 9-1 (43 mg, 0.089 mmol), 4 Å molecular sieves (56 mg) and NMO (16 mg, 0.14 mmol) in dichloromethane (0.5 mL) was treated with TPAP (3 mg, 0.009 mmol). The mixture was stirred for 5 min. at 0° C. and then for 1 h at room temperature. The mixture was then filtered through a pad of silica gel, washing with ethyl acetate. The solvents were evaporated and the residue was purified by flash chromatography on silica gel (10% ethyl acetate/hexanes) to give 9-2 (34 mg, 79%).

(Z)-7-{(1R,2S,3R,5R)-3-(tert-Butyl-dimethyl-silanyloxy)-5-chloro-2-[4-(1-hydroxy-2-methyl-propyl)-phenyl]-cyclopentyl}-hept-5-enoic acid methyl ester (9-3). i-Propylmagnesium chloride (335 μL, 0.67 mmol, 2 M/THF) was added to an ice cold solution of 9-2 (161 mg 0.34 mmol) in THF (1.4 mL). The reaction was stirred for 3 h at 0° C. and then was quenched by addition of 20 mL saturated NH$_4$Cl solution. The mixture was extracted with ethyl acetate (3×30 mL) and the combined ethyl acetate solution was washed with brine. The solution was then dried (Na$_2$SO$_4$), filtered and evaporated. Purification of the residue by flash chromatography on silica gel (5%→7%→9% ethyl acetate/hexanes) gave 9-3 (76 mg, 43%).

(Z)-7-{(1R,2S,3R,5R)-3-(tert-Butyl-dimethyl-silanyloxy)-5-chloro-2-[4-(1-hydroxy-2,2-dimethyl-propyl)-phenyl]-cyclopentyl}-hept-5-enoic acid methyl ester (9-4). The above procedure was followed using t-BuMgCl in place of i-Propylmagnesium chloride to give 9-4 (60 mg, 62%).

(Z)-7-{(1R,2S,3R,5R)-5-Chloro-3-hydroxy-2-[4-(1-hydroxy-2-methyl-propyl)-phenyl]-cyclopentyl}-hept-5-enoic acid methyl ester (9-5). The representative HF-pyridine deprotection procedure was followed to give 9-5 (45 mg, 81%).

(Z)-7-{(1R,2S,3R,5R)-5-Chloro-3-hydroxy-2-[4-(1-hydroxy-2,2-dimethyl-propyl)-phenyl]-cyclopentyl}-hept-5-enoic acid methyl ester (9-6). The representative HF-pyridine deprotection procedure was followed to give 9-6 (84 mg, 96%).

(Z)-7-{(1R,2S,3R,5R)-5-Chloro-3-hydroxy-2-[4-(1-hydroxy-2-methyl-propyl)-phenyl]-cyclopentyl}-hept-5-enoic acid (9-7). The representative LiOH mediated hydrolysis procedure was followed.

(Z)-7-{(1R,2S,3R,5R)-5-Chloro-3-hydroxy-2-[4-(1-hydroxy-2,2-dimethyl-propyl)-phenyl]-cyclopentyl}-hept-5-enoic acid (9-8). The representative LiOH mediated hydrolysis procedure was followed.

7-{(1R,2S,3R,5R)-5-Chloro-3-hydroxy-2-[4-(1-hydroxy-2-methyl-propyl)-phenyl]-cyclopentyl}-heptanoic acid methyl ester (9—9). The representative hydrogenation procedure was followed using ethyl acetate as the solvent.

7-{(1R,2S,3R,5R)-5-Chloro-3-hydroxy-2-[4-(1-hydroxy-2,2-dimethyl-propyl)-phenyl]-cyclopentyl}-heptanoic acid methyl ester (9-10). The representative hydrogenation procedure was followed using ethyl acetate as the solvent.

7-{(1R,2S,3R,5R)-5-Chloro-3-hydroxy-2-[4-(1-hydroxy-2-methyl-propyl)-phenyl]-cyclopentyl}-heptanoic acid (9-11). The representative LiOH procedure was used.

7-{(1R,2S,3R,5R)-5-Chloro-3-hydroxy-2-[4-(1-hydroxy-2,2-dimethyl-propyl)-phenyl]-cyclopentyl}-heptanoic acid (9-12). The representative LiOH procedure was used.

Representative three component coupling procedure: [4-((1R,2S,3R)-3-(tert-Butyl-dimethyl-silanyloxy)-2-{4-[(tert-butyl-dimethyl-silanyloxy)-cyclohexyl-methyl]-phenyl}-5-oxo-cyclopentyl)-but-2-ynyloxy]-acetic acid methyl ester (10-3). t-BuLi (3.3 mL, 5.6 mmol, 1.7 M/pentane) was added to a −78° C. THF (4.0 mL) solution of 5-1 (990 mg, 2.58 mmol). After 30 min., Me$_2$Zn (1.5 mL, 3.0 mmol, 2 M/toluene) was added and the flask was placed in an ice bath for 15 min. The reaction was recooled to −78° C. and a solution of enone 10-1 (387 mg, 1.83 mmol, obtained from Evotec OAI, 151 Milton Park, Abington, Oxon, OX 14 4SD, UK) in THF (2.0 mL) was added by syringe pump over 1.75 h., rinsing with 0.5 mL THF. The reaction was allowed to stir for 30 min. and then HMPA (2.8 mL, 16.1 mmol) was added followed by iodide 10-2 (2.487 g, 9.3 mmol, prepared according to U.S. patent application Ser. No. 10/861,957, filed Jun. 3, 2004). The reaction was stirred at −40° C. for 19 h and then was quenched by addition of saturated NH$_4$Cl solution (40 mL). A little H$_2$O was added to dissolve solids and the mixture was extracted with dichloromethane (3×30 mL). The combined dichloromethane solution was dried (Na$_2$SO$_4$), filtered and evaporated. Purification by flash chromatography on silica gel gave the title ketone (563 mg, 0.86 mmol, 47%).

[4-((1R,2S,3R,5S)-3-(tert-Butyl-dimethyl-silanyloxy)-2-{4-[(tert-butyl-dimethyl-silanyloxy)-cyclohexyl-methyl]-phenyl}-5-hydroxy-cyclopentyl)-but-2-ynyloxy]-acetic acid methyl ester (10-4). L-selectride (0.76 mL, 0.76 mmol, 1 M/THF) was added to a −78° C. THF (20 mL) solution of 10-3 (415 mg, 0.63 mmol). The reaction was stirred for 1 h and then 3% H$_2$O$_2$ (14 mL) was added. The resulting mixture was stirred at room temperature for 45 min. and then saturated NH$_4$Cl solution (60 mL) was added. The resulting mixture was extracted with ethyl acetate (3×40 mL) and the combined ethyl acetate solution was washed with brine. The solution was then dried (Na$_2$SO$_4$), filtered and evaporated. Purification by flash chromatography on silica gel (25% ethyl acetate/hexanes) gave the title alcohol (255 mg, 0.39 mmol, 61%).

[4-((1R,2S,3R,5R)-3-(tert-Butyl-dimethyl-silanyloxy)-2-{4-[(tert-butyl-dimethyl-silanyloxy)-cyclohexyl-methyl]-phenyl}-5-chloro-cyclopentyl)-but-2-ynyloxy]-acetic acid methyl ester (10-5). MsCl (0.13 mL, 1.7 mmol) was added to a dichloromethane (2 mL) solution of the alcohol (255 mg, 0.39 mmol) and triethylamine (0.27 mL, 1.9 mmol). After 2.5 h, 20 mL saturated NaHCO$_3$ solution was added and the resulting mixture was extracted with dichloromethane (3×15 mL). The combined dichloromethane solution was then dried (Na$_2$SO$_4$), filtered and evaporated.

A mixture of the crude mesylate and (n-Bu)$_4$NCl (1.032 g, 3.7 mmol) in toluene (3.5 mL) was stirred at 40° C. for 22 h. The mixture was allowed to cool to room temperature and then was filtered through silica gel eluting with ethyl acetate. The solvent was evaporated and the residue taken on to the next step.

(4-{(1R,2S,3R,5R)-5-Chloro-2-[4-(cyclohexyl-hydroxy-methyl)-phenyl]-3-hydroxy-cyclopentyl}-but-2-ynyloxy)-acetic acid methyl ester (10-6). HF-pyridine (1.7 mL) was added to a 0° C. CH$_3$CN (10 mL) solution of the crude chloride from above (0.39 mmol). The reaction was stirred at 0° C. for 21 h and then saturated NaHCO$_3$ solution (255 mL) was added. The resulting mixture was extracted with dichloromethane (3×100 mL) and the combined dichloromethane solution was dried (Na$_2$SO$_4$), filtered and evaporated. Purification by flash chromatography on silica gel (40% ethyl acetate/hexanes→45%→50%) gave the title diol (152 mg, 0.34 mmol, 87% from 10-4).

(4-{(1R,2S,3R,5R)-5-Chloro-2-[4-(cyclohexyl-hydroxy-methyl)-phenyl]-3-hydroxy-cyclopentyl}-but-2-ynyloxy)-acetic acid (10-7). A mixture of the ester (11 mg, 0.024 mmol) and rabbit liver esterase (5 mg) in CH$_3$CN (0.2 mL)/pH 7.2 phosphate buffer (2 mL) was stirred for 24 h. The mixture was then coevaporated with CH$_3$CN (2×50 mL) and the residue was taken into 10% methanol/dichloromethane and filtered through glass wool. Purification by preparative thin layer chromatography (20% methanol/dichloromethane) gave the title acid (6 mg, 0.014 mmol, 57%).

((Z)-4-{(1R,2S,3R,5R)-5-Chloro-2-[4-(cyclohexyl-hydroxy-methyl)-phenyl-3-hydroxy-cyclopentyl}-but-2-enyloxy)-acetic acid methyl ester (11-1). Ethanol (95%, 2 mL) was added to NiCl$_2$ (47 mg, 0.36 mmol) and NaBH$_4$ (5 mg, 0.13 mmol). The resulting black mixture was stirred for 5 min. and then ethylenediamine (35 µL, 0.52 mmol) was added. After 15 min., a solution of alkyne 10-6 (29 mg, 0.065 mmol) in 0.5 mL 95% ethanol was added, rinsing with 0.5 mL ethanol. The flask was purged with H$_2$ and allowed to stir under 1 atm H$_2$ for 24 h. The mixture was then filtered through celite, evaporated and the residue was purified by flash chromatography on silica gel (45→50% ethyl acetate/hexanes) to give 17 mg (0.038 mmol, 58%) of 11-1.

((Z)-4-{(1R,2S,3R,5R)-5-Chloro-2-[4-(cyclohexyl-hydroxy-methyl)-phenyl]-3-hydroxy-cyclopentyl}-but-2-enyloxy)-acetic acid (11-2). The representative rabbit liver esterase procedure was followed, starting with the corresponding methyl ester.

(4-{(1R,2S,3R,5R)-5-Chloro-2-[4-(cyclohexyl-hydroxy-methyl)-phenyl]-3-hydroxy-cyclopentyl}-butoxy)-acetic acid methyl ester (11-3). A mixture of 10-6 (11 mg, 0.024 mmol) and 5% Pd/C (6 mg, 0.003 mmol) in ethyl acetate (1 mL) was stirred under 1 atm H$_2$ (balloon) for 18 h. The mixture was filtered and evaporated. The residue was purified by preparative TLC on silica gel (45% ethyl acetate/ hexanes) to give 11-3 (8 mg, 0.018 mmol, 75%).

(4-{(1R,2S,3R,5R)-5-Chloro-2-[4-(cyclohexyl-hydroxy-methyl)-phenyl]-3-hydroxy-cyclopentyl}-butoxy)-acetic acid (11-4). The representative rabbit liver esterase procedure was followed, starting with the corresponding methyl ester.

(3-Hydroxymethyl-phenoxy)-acetic acid methyl ester (12-2). A mixture of 12-1 (5.031 g, 40.5 mmol) and $K_2CO_3$ (5.750 g, 41.6 mmol) in 10 mL methanol was treated with methyl bromoacetate (3.9 mL, 42.4 mmol). The reaction was stirred in a 50° C. oil bath for 23 h and then was allowed to cool to room temperature. HCl (100 mL, 1 M) was then added and the mixture was extracted with dichloromethane (3×75 mL). The combined dichloromethane solution was dried ($Na_2SO_4$), filtered and evaporated and the residue was purified by flash chromatography on silica gel (10%→15%→20%→25% ethyl acetate/hexanes) to give 12-2 (5.795 g, 29.5 mmol, 73%).

(3-Iodomethyl-phenoxy)-acetic acid methyl ester (12-3). Dichloromethane (85 mL) was added to $Ph_3P$ (4.942 g, 18.8 mmol), imidazole (1.311 g, 19.3 mmol) and $I_2$ (4.735 g, 18.7 mmol). The mixture was stirred for 5 min. and then a solution of 12-2 (2.937 g, 15.0 mmol) in 15 mL dichloromethane was added by cannula. The reaction was stirred for 3 h, silica gel was added and the mixture evaporated. The residue was purified by flash chromatography on silica gel (10%→20%→30% ethyl acetate/hexanes) to give 12-3 (4.246 g, 13.9 mmol, 93%).

[3-((1R,2S,3R)-3-(tert-Butyl-dimethyl-silanyloxy)-2-{3-[(tert-butyl-dimethyl-silanyloxy)-(1-propyl-cyclobutyl)-methyl]-phenyl}-5-oxo-cyclopentylmethyl)-phenoxy]-acetic acid methyl ester (13-2). The representative three component coupling method, as described for 10-3, was used giving 13-2 (278 mg, 43%).

[3-((1R,2S,3R)-3-Hydroxy-2-{3-[(S)-hydroxy-(1-propyl-cyclobutyl)-methyl]-phenyl}-5-oxo-cyclopentylmethyl)-phenoxy]-acetic acid methyl ester (13-3). The representative HF-pyridine deprotection procedure was used.

[3-((1R,2S,3R)-3-Hydroxy-2-{3-[(S)-hydroxy-(1-propyl-cyclobutyl)-methyl]-phenyl}-5-oxo-cyclopentylmethyl)-phenoxy]-acetic acid (13-4). The representative rabbit liver esterase procedure was followed, starting with 13-3.

[3-((1R,2S,3R,5S)-3-(tert-Butyl-dimethyl-silanyloxy)-2-{3-[(S)-(tert-butyl-dimethyl-silanyloxy)-(1-propyl-cyclobutyl)-methyl]-phenyl}-5-hydroxy-cyclopentylmethyl)-phenoxy]-acetic acid methyl ester (14-1). The representative L-selectride procedure was used.

[3-((1R,2S,3R,5R)-3-(tert-Butyl-dimethyl-silanyloxy)-2-{3-[(S)-(tert-butyl-dimethyl-silanyloxy)-(1-propyl-cyclobutyl)-methyl]-phenyl}-5-chloro-cyclopentylmethyl)-phenoxy]-acetic acid methyl ester (14-2). The representative method for conversion of the C9 alcohol to the C9 chloride, as described for 6-2, was used.

[3-((1R,2S,3R,5R)-5-Chloro-3-hydroxy-2-{3-[(S)-hydroxy-(1-propyl-cyclobutyl)-methyl]-phenyl}-cyclopentylmethyl)-phenoxy]-acetic acid methyl ester (14-3). The representative HF-pyridine deprotection procedure was used.

[3-((1R,2S,3R,5R)-5-Chloro-3-hydroxy-2-{3-[(S)-hydroxy-(1-propyl-cyclobutyl)-methyl]-phenyl}-cyclopentylmethyl)-phenoxy]-acetic acid (14-4). The representative rabbit liver esterase procedure was followed.

5-Bromo-indan-1-ol (15-2). $NaBH_4$ (350 mg, 9.25 mmol) was added to an ice cold solution of ketone 15-1 (1.632 g, 7.73 mmol) in methanol (15 mL). The reaction was allowed to warm to room temperature and after 45 min., 50 mL 1 M HCl was added. The resulting mixture was extracted with ethyl acetate (3×60 mL) and the combined ethyl acetate solution was washed with brine. The solution was then dried ($Na_2SO_4$), filtered and evaporated. The residue was purified by flash chromatography on silica gel (25% ethyl acetate/hexanes) to give 15-2 (1.607 g, 98%).

5-Bromo-1-(4-methoxy-benzyloxy)-indan (15-3). A similar procedure as for 7-2 was used.

(Z)-7-{(1R,2S,3R)-3-(tert-Butyl-dimethyl-silanyloxy)-2-[1-(4-methoxy-benzyloxy)-indan-5-yl]-5-oxo-cyclopentyl}-hept-5-enoic acid methyl ester (15-4). A −78° C. solution of thiophene (240 µL, 3.0 mmol) in ether (2.5 mL) was treated with n-BuLi (2.1 mL, 3.36 mmol, 1.6 M/hexanes). The reaction was stirred at 0° C. for 1 h and then was recooled to −78° C. The resulting mixture was then cannula transferred to a −78° C. mixture of CuCN (306 mg, 3.4 mmol) in 2.5 mL ether. The reaction was stirred at room temperature for 30 min. and then was recooled to −78° C.

In another flask, a −78° C. solution of aryl bromide 15-3 (833 mg, 2.5 mmol) in 5 mL ether was teated with t-BuLi (3.2 mL, 5.4 mmol, 1.7 M/pentane). The resulting mixture was stirred for 1 h at −78° C. and then was added to the 2-thienylCuCNLi mixture from above, rinsing with 1 mL ether. The reaction was stirred for 15 min. at 0° C. and then recooled to −78° C. at which time a solution of the enone 5-2 (893 mg, 2.5 mmol, obtained from Nissan Chemical Industries, LTD, Chemicals Division 3-7-1 Kanda-Nishiki-cho, Chiyoda-ku, Tokyo 101-0054, Japan) in 3 mL ether was added by cannula. The reaction was stirred for 15 min. at −78° C. and then allowed to warm to room temperature.

After 1 h, the reaction was quenched by addition of 65 mL 10% $NH_4OH$ (conc.)/saturated $NH_4Cl$ solution. The mixture was extracted with ethyl acetate (3×50 mL) and the combined ethyl acetate solution was dried ($Na_2SO_4$), filtered and evaporated. Purification by flash chromatography on silica gel (15% ethyl acetate/hexanes) gave the title compound (792 mg, 1.3 mmol, 52%).

(Z)-7-{(1R,2S,3R)-3-Hydroxy-2-[1-(4-methoxy-benzyloxy)-indan-5-yl]-5-oxo-cyclopentyl}-hept-5-enoic acid methyl ester (15-5). A mixture of 15-4 (20 mg, 0.032 mmol) in acetic acid (0.3 mL)/water (0.1 mL)/THF (0.1 mL) was stirred at room temperature. After two days, saturated $NaHCO_3$ solution was added and the resulting mixture was extracted with dichloromethane (3×20 mL). The combined dichloromethane solution was dried ($Na_2SO_4$), filtered and evaporated. The residue was purified by flash chromatography on silica gel (20% ethyl acetate/hexanes→30% →40%) which gave the title compound (11 mg, 67%).

(Z)-7-[(1R,2S,3R)-3-Hydroxy-2-(1-hydroxy-indan-5-yl)-5-oxo-cyclopentyl]-hept-5-enoic acid methyl ester (15-6). DDQ (41 mg, 0.18 mmol) was added to a mixture of 15-5 (11 mg, 0.021 mmol) in dichloromethane (3.5 mL)/water (175 µL). After 55 min., saturated $NaHCO_3$ solution was added and the resulting mixture was extracted with dichloromethane (3×50 mL). The combined dichloromethane solution was washed with brine and then was dried ($Na_2SO_4$), filtered and evaporated. Purification by flash chromatography on silica gel (50%→60% ethyl acetate/hexanes) gave 15-6 (34 mg, 60%).

(Z)-7-[(1R,2S,3R)-3-Hydroxy-2-(1-hydroxy-indan-5-yl)-5-oxo-cyclopentyl]-hept-5-enoic acid (15-7). The representative rabbit liver esterase procedure was followed.

(Z)-7-[(1R,2S,3R)-3-Hydroxy-5-oxo-2-(1-oxo-indan-5-yl)-cyclopentyl]-hept-5-enoic acid methyl ester (15-8). DDQ (10 mg, 0.041 mmol) was added to a mixture of 15-5 (11 mg, 0.021 mmol) in dichloromethane (0.5 mL)/water (25 µL). After 1 h, dichloroethane (0.5 mL) was added and the reaction was stirred overnight. Saturated $NaHCO_3$ solution was added and the resulting mixture was extracted with dichloromethane (3×20 mL). The combined dichloromethane solution was washed with brine and then was dried ($Na_2SO_4$), filtered and evaporated. Purification of the residue by flash chromatography on silica gel (60% ethyl acetate/hexanes) gave 15-8 (5 mg, 59%).

Z)-7-[(1R,2S,3R)-3-Hydroxy-5-oxo-2-(1-oxo-indan-5-yl)-cyclopentyl]-hept-5-enoic acid (15-9). The representative rabbit liver esterase procedure was followed.

7-[(1R,2S,3R)-3-Hydroxy-2-(1-hydroxy-indan-5-yl)-5-oxo-cyclopentyl]-heptanoic acid methyl ester (15-10) and 7-((1R,2S,3R)-3-Hydroxy-2-indan-5-yl-5-oxo-cyclopentyl)-heptanoic acid methyl ester (15-12). The representative hydrogenation procedure was followed, using ethyl acetate as solvent, and afforded 15-10 (13 mg, 0.034 mmol, 63%) and 15-12 (3.9 mg, 0.011 mmol, 20%).

7-[(1R,2S,3R)-3-Hydroxy-2-(1-hydroxy-indan-5-yl)-5-oxo-cyclopentyl]-heptanoic acid (15-11). The representative rabbit liver esterase procedure was followed.

7-((1R,2S,3R)-3-Hydroxy-2-indan-5-yl-5-oxo-cyclopentyl)-heptanoic acid (15-13). The representative rabbit liver esterase procedure was followed.

(Z)-7-{(1R,2S,3R,5S)-3-(tert-Butyl-dimethyl-silanyloxy)-5-hydroxy-2-[1-(4-methoxy-benzyloxy)-indan-5-yl]-cyclopentyl}-hept-5-enoic acid methyl ester (16-1). The representative L-selectride procedure was used.

(Z)-7-{(1R,2S,3R,5R)-3-(tert-Butyl-dimethyl-silanyloxy)-5-chloro-2-[1-(4-methoxy-benzyloxy)-indan-5-yl]-cyclopentyl}-hept-5-enoic acid methyl ester (16-2). The representative procedure was used.

(Z)-7-{(1R,2S,3R,5R)-5-Chloro-3-hydroxy-2-[1-(4-methoxy-benzyloxy)-indan-5-yl]-cyclopentyl}-hept-5-enoic acid methyl ester (16-3). A procedure analogous to the one used to prepare 15-5 was used.

(Z)-7-[(1R,2S,3R,5R)-5-Chloro-3-hydroxy-2-(1-hydroxy-indan-5-yl)-cyclopentyl]-hept-5-enoic acid methyl ester (16-4). A procedure analogous to the one used to prepare 15-6 was used.

(Z)-7-[(1R,2S,3R,5R)-5-Chloro-3-hydroxy-2-(1-hydroxy-indan-5-yl)-cyclopentyl]-hept-5-enoic acid (16-5). The representative rabbit liver esterase hydrolysis was used.

Representative procedure for preparation of isopropyl esters: (Z)-7-[(1R,2S,3R,5R)-5-Chloro-3-hydroxy-2-(1-hydroxy-indan-5-yl)-cyclopentyl]-hept-5-enoic acid isopropyl ester (16-6). Isopropyl iodide (32 µL, 0.32 mmol) was added to a solution of 16-5 (12 mg, 0.032 mmol) in acetone (0.5 mL). After 3 days, HCl (10 mL, 1 M) was added and the resulting mixture was extracted with dichloromethane (3×15 mL). The combined dichloromethane solution was dried ($Na_2SO_4$), filtered and evaporated. The residue was purified by flash chromatagraphy on silica gel (50% ethyl acetate/hexanes→53%) to give 16-6 (9 mg, 0.021 mmol, 67%).

7-[(1R,2S,3R,5R)-5-Chloro-3-hydroxy-2-(1-hydroxy-indan-5-yl)-cyclopentyl]-heptanoic acid methyl ester (16-7) and 7-((1R,2S,3R,5R)-5-Chloro-3-hydroxy-2-indan-5-yl-cyclopentyl)-heptanoic acid methyl ester (16-9). A mixture of 16-4 (22 mg, 0.056 mmol) and 5% Pd/C (13 mg, 0.006 mmol) in ethyl acetate (2.5 mL) was stirred under 1 atm $H_2$ (balloon). After 19 h, the mixture was filtered through celite and evaporated. Purification by flash chromatography on silica gel (40%→45% ethyl acetate/hexanes) gave 12 mg (0.030 mmol, 53%) of 16-7 and 10 mg (0.025 mmol, 45%) of 16-9.

7-[(1R,2S,3R,5R)-5-Chloro-3-hydroxy-2-(1-hydroxy-indan-5-yl)-cyclopentyl]-heptanoic acid (16-8). The representative rabbit liver esterase procedure was used.

7-((1R,2S,3R,5R)-5-Chloro-3-hydroxy-2-indan-5-yl-cyclopentyl)-heptanoic acid (16-10). The representative rabbit liver esterase procedure was used.

(Z)-7-{(1R,2S,3R)-3-(tert-Butyl-dimethyl-silanyloxy)-5-fluoro-2-[1-(4-methoxy-benzyloxy)-indan-5-yl]-cyclopentyl}-hept-5-enoic acid methyl ester (17-1) and (Z)-7-{(4R,5R)-4-(tert-Butyl-dimethyl-silanyloxy)-5-[1-(4-methoxy-benzyloxy)-indan-5-yl]-cyclopent-1-enyl}-hept-5-enoic acid methyl ester (17-2). A solution of 16-1 (212 mg, 0.35 mmol) in 1 mL THF was added to a −78° C. solution of (diethylamino)sulfur trifluoride (DAST, 50 µL, 0.38 mmol) in 1 mL THF, rinsing with 0.5 mL THF. The reaction was stirred at room temperature for 1.5 h and the volatiles were evaporated. The residue was purified by flash chromatography on silica gel (5%→8% ethyl acetate/hexanes) to give 17-1 (54 mg, 25%) and 17-2 (54 mg, 26%).

7-[(1R,2S,3R)-5-Fluoro-3-hydroxy-2-(1-hydroxy-indan-5-yl)-cyclopentyl]-heptanoic acid methyl ester (17-3). This compound was prepared by an analogous sequence to the 9-chloro derivative (16-7, FIG. 16).

7-[(1R,2S,3R)-5-Fluoro-3-hydroxy-2-(1-hydroxy-indan-5-yl)-cyclopentyl]-heptanoic acid (17-4). The representative LiOH procedure was used.

(Z)-7-[(1R,2S,3R)-5-Fluoro-3-hydroxy-2-(1-hydroxy-indan-5-yl)-cyclopentyl]-hept-5-enoic acid methyl ester (17-5). This compound was prepared by an analogous sequence to the 9-chloro derivative (16-4, FIG. 16).

(Z)-7-[(1R,2S,3R)-5-Fluoro-3-hydroxy-2-(1-hydroxy-indan-5-yl)-cyclopentyl]-hept-5-enoic acid (17-6). The representative LiOH procedure was used.

EXAMPLE 2

Binding Data

Ki

Competition binding experiments were performed in a medium containing Hank's balanced salt solution, Hepes 20 mM, pH 7.3, membranes (~60 µg protein) or $2\times10^5$ cells from HEK 293 cells stably expressing human EP2 receptors, [$^3$H]PGE2 (10 nM) and various concentrations of test compounds in a total volume of 300 µl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 µM). Binding data fitted to the binding model for a single class of binding sites, using nonlinear regression analysis. $IC_{50}$ values thus obtained were converted to Ki using the equation of Ki=$(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10 N HCl is added to achieve a pH of 7.4).

The cell homogenate was centrifuged at 19000 r.p.m. for 20 min at 40° C. using a Beckman Ti-60 rotor. The resultant pellet was resuspended in TME buffer to give a final 1 mg/ml protein concentration, as determined by Biorad assay. Radioligand binding competition assays vs. [$^3$H-] 17-phenyl PGF$_{2\alpha}$ (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] PGE$_2$ (specific activity 180 Ci mmol) was used as the radioligand for EP receptors. [$^3$H] 17-phenyl PGF$_{2\alpha}$ was employed for FP receptor binding studies. Binding studies employing EP$_1$, EP$_2$, EP$_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-PGE$_2$, or 5 nM [$^3$H] 17-phenyl PGF$_{2\alpha}$ and non-specific binding determined with 10$^{-5}$M of unlabeled PGE$_2$, or 17-phenyl PGF$_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3A}$/Gqi5; hEP$_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of 5×10$^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3A}$/Gqi5; hEP$_4$/Gqs5); PGF$_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of 10$^{-5}$ M. To generate concentration-response curves, four compounds per plate were tested in duplicates in a concentration range between 10$^{-5}$ and 10$^{-11}$ M. The duplicate values were averaged. In either, HTS or CoRe format each compound was tested on at least 3 separate plates using cells from different passages to give an n≧3.

The results of the binding and activity studies, presented in Table 1 below, demonstrate that the compounds disclosed herein are selective prostaglandin EP$_2$ agonists, and are thus useful for the treatment of glaucoma, ocular hypertension, the other diseases or conditions disclosed herein.

| | | BINDING IC50 (nm) | | |
|---|---|---|---|---|
| NUMBER | STRUCTURE | HEP2 | HEP3 | HEP4 |

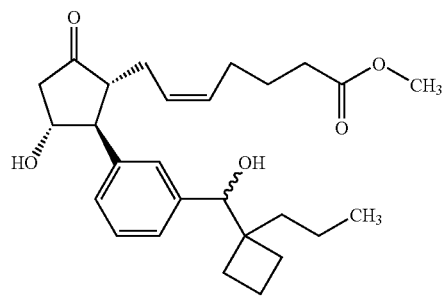

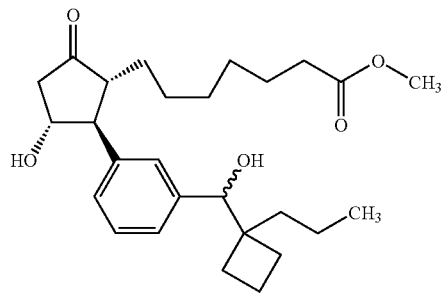
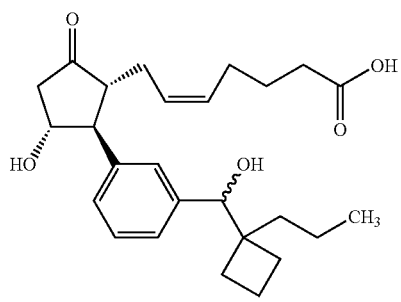
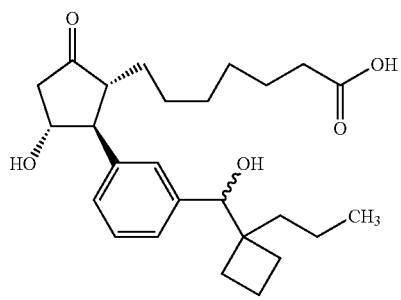
e2-2
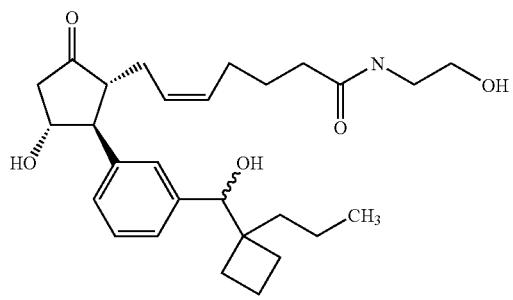
e2-2
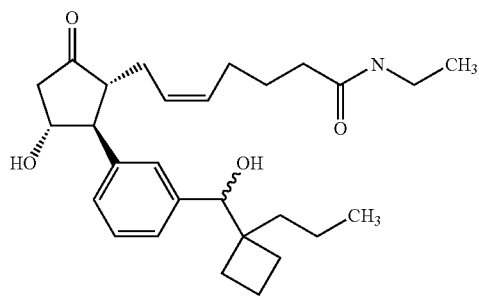

-continued
e2-2
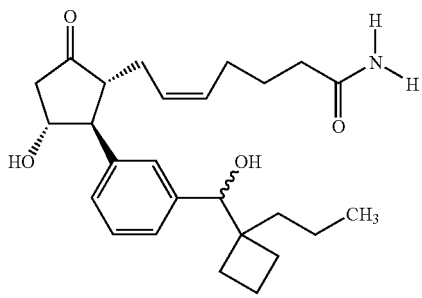
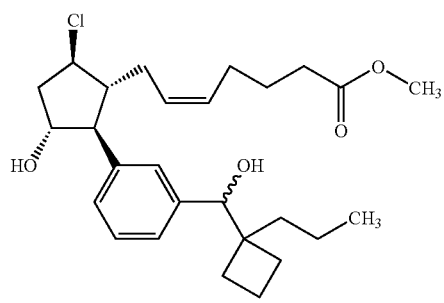
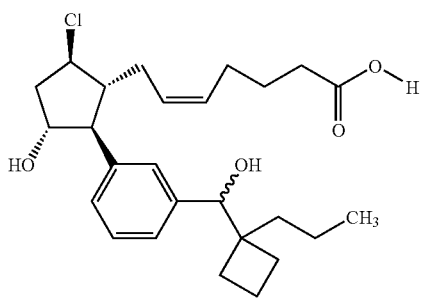
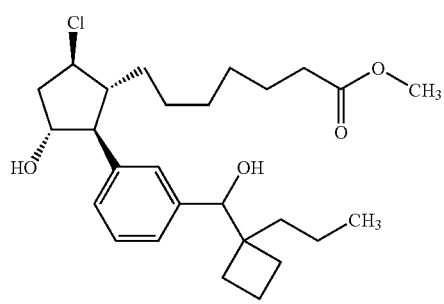
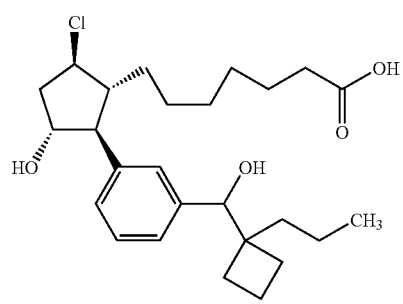

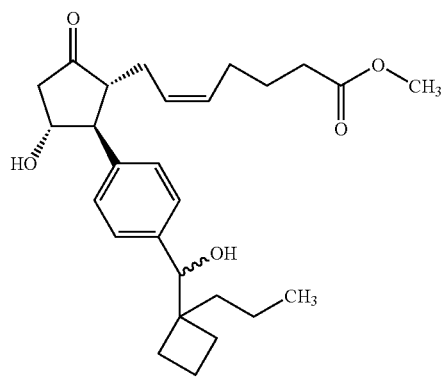
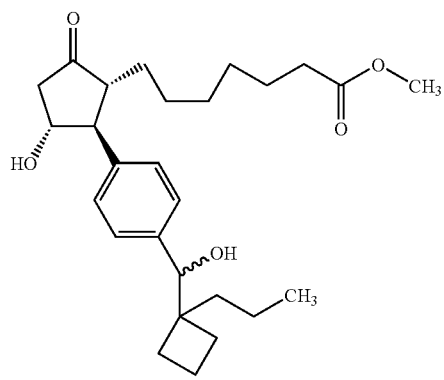
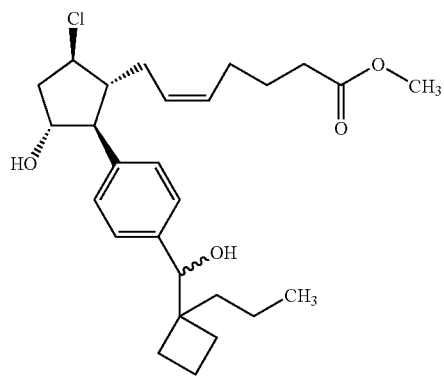
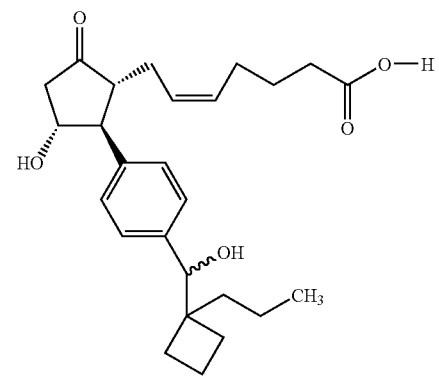

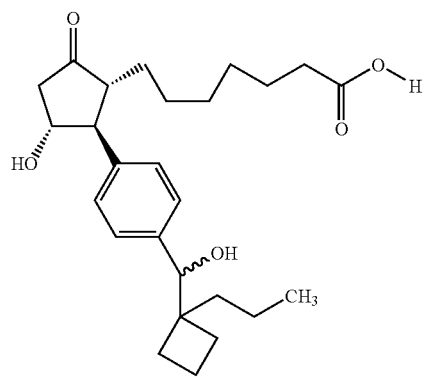
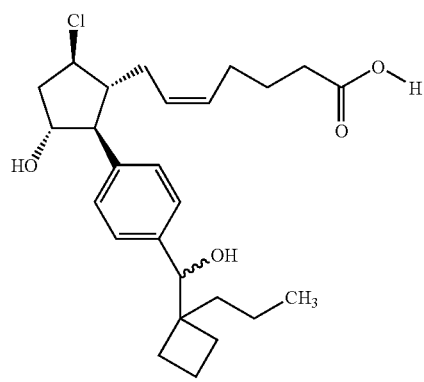
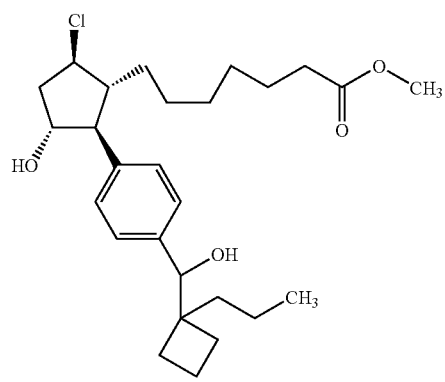
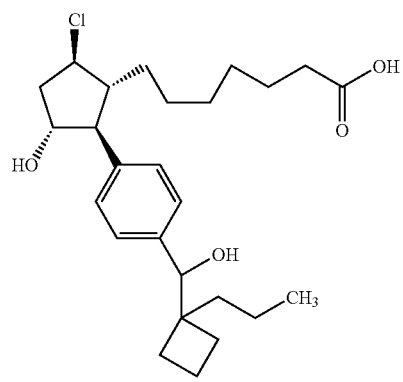

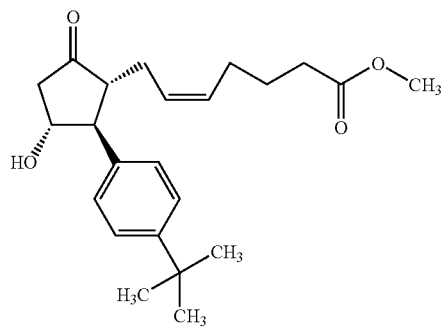
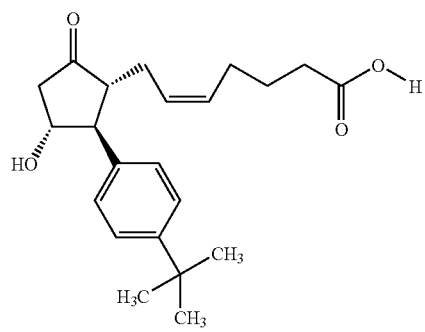
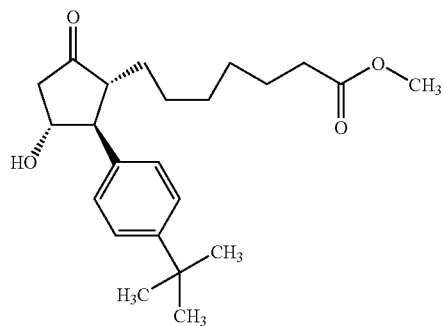
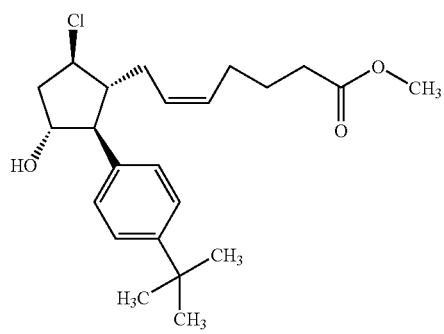

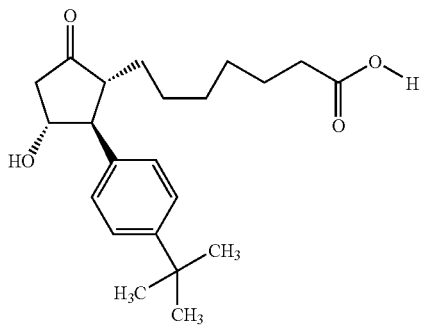
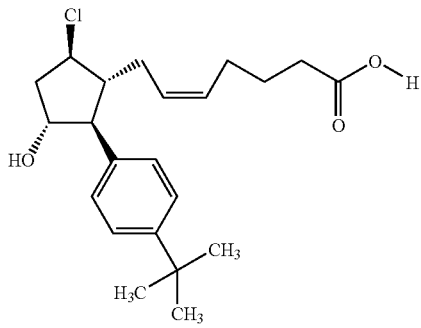
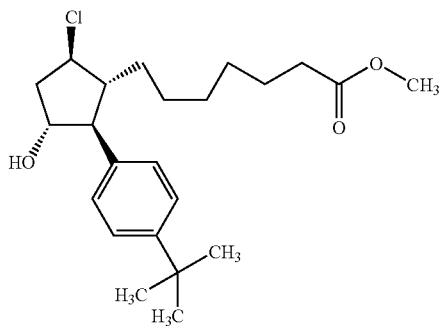
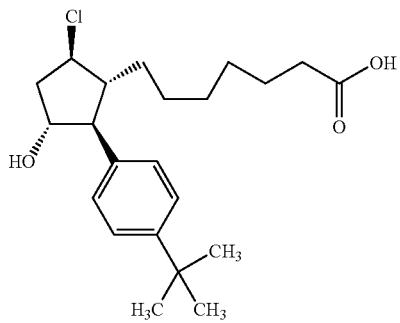

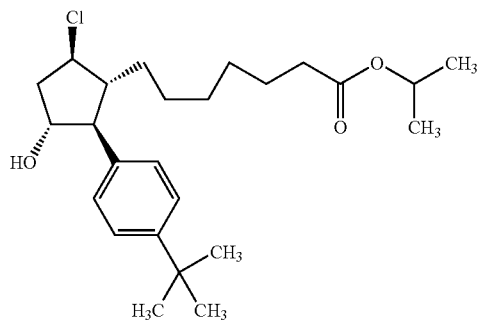
5-4
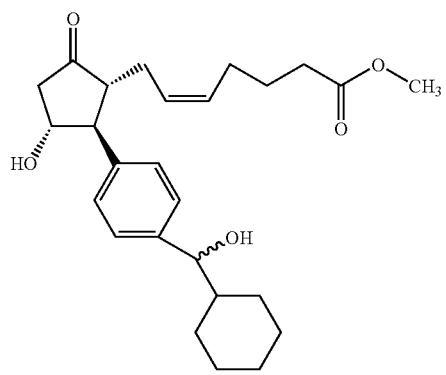
5-5
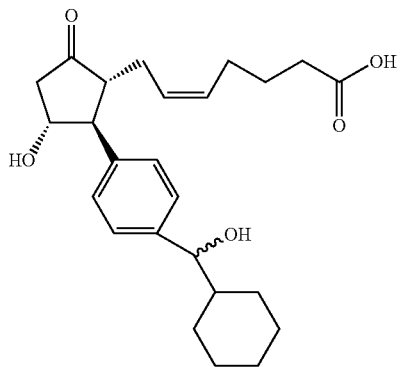
5-7
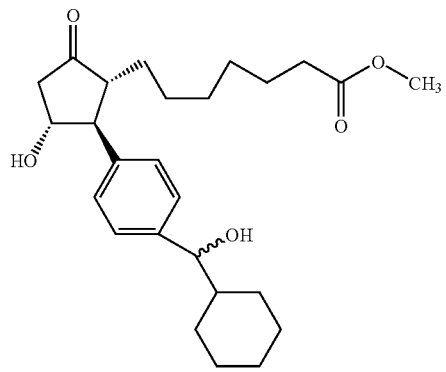

-continued
5-8 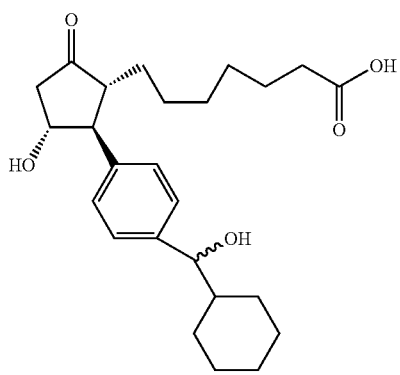
6-3 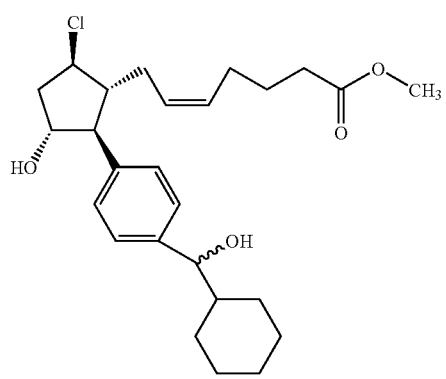
6-4 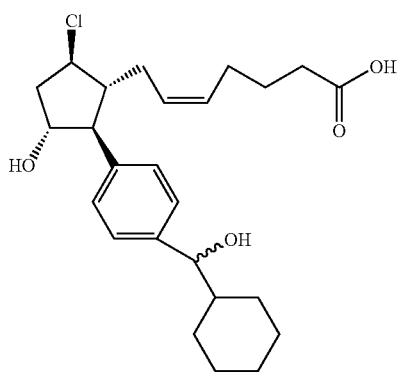
6-6 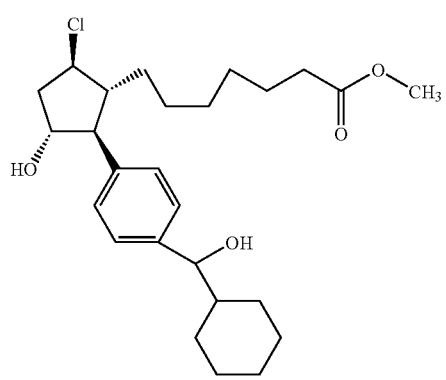

6-8
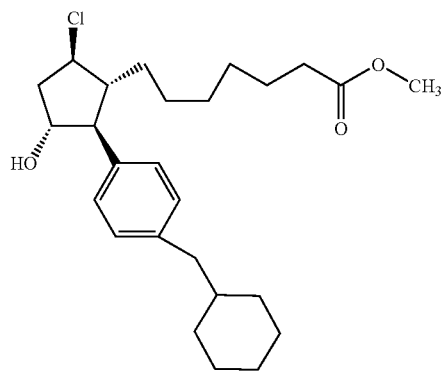
6-9
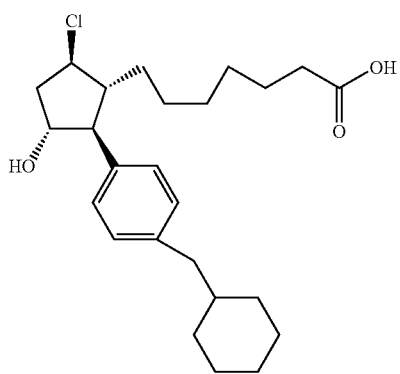
6-7
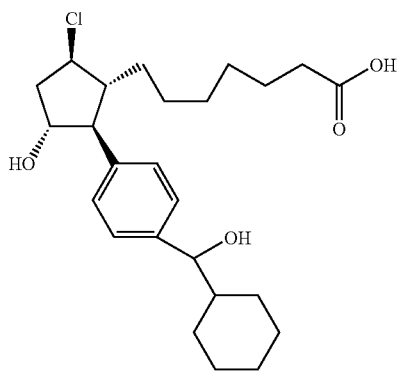
6-5
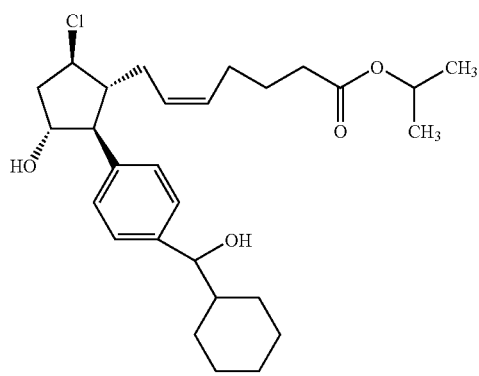

-continued
13-3 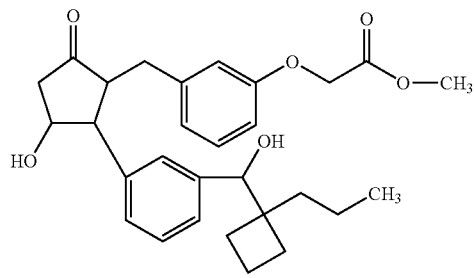
13-4 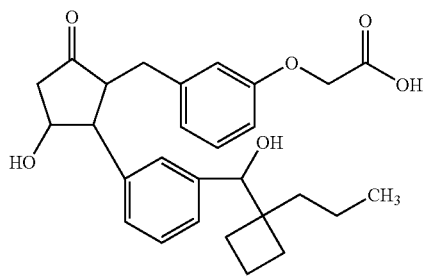
14-3 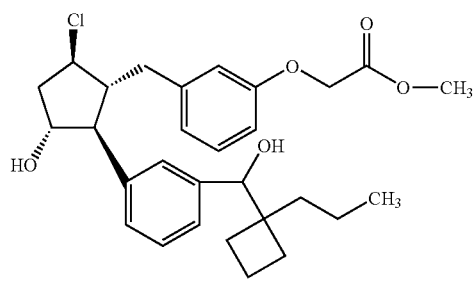
14-4 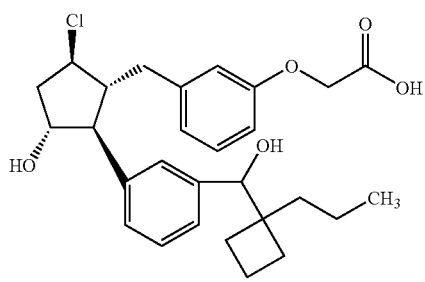  5200  NA  NA
11-2 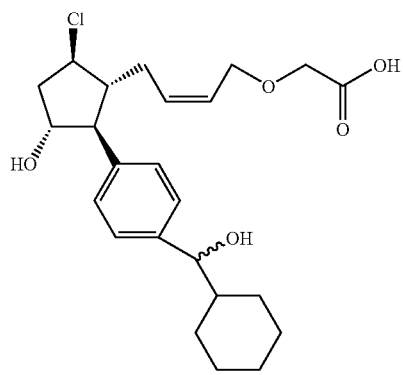

11-1
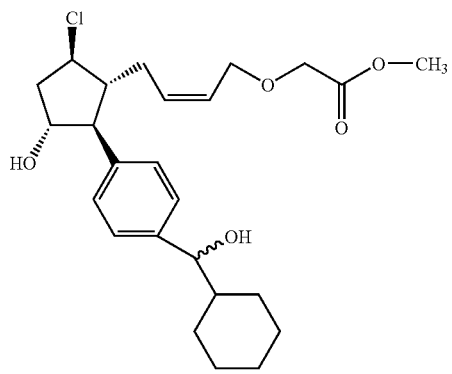
11-3
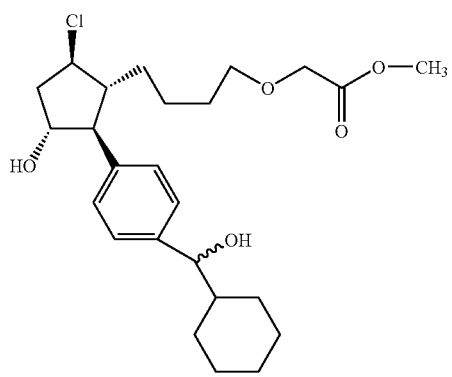
11-4
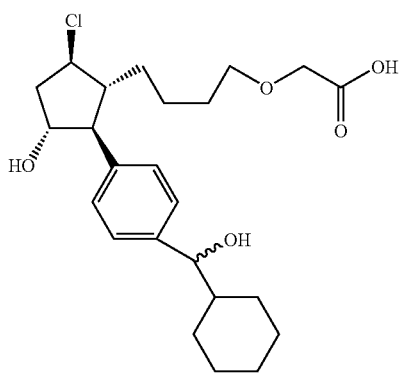
10-7
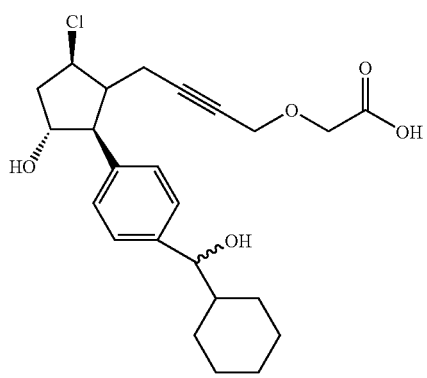

-continued
10-6
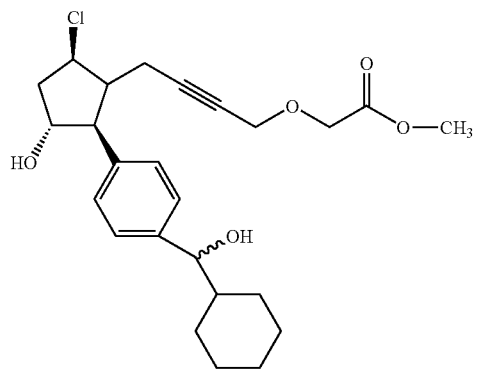
15-7
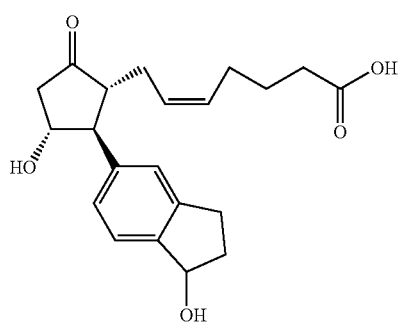
15-12
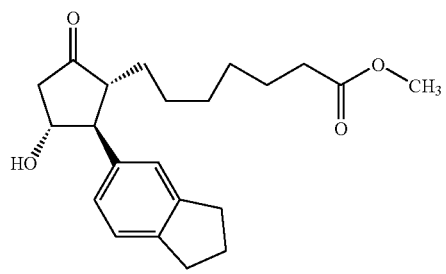
15-10
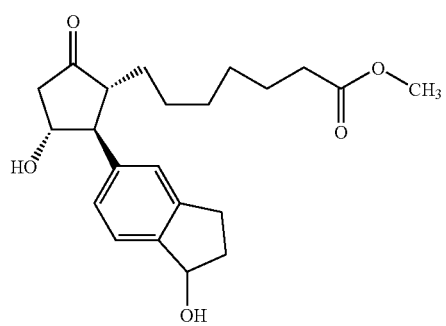
15-11
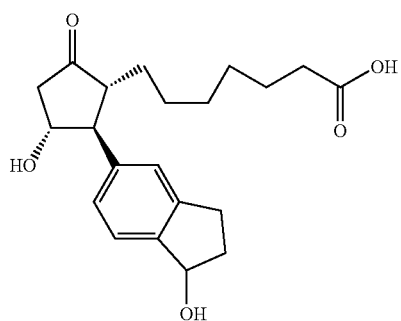

15-6 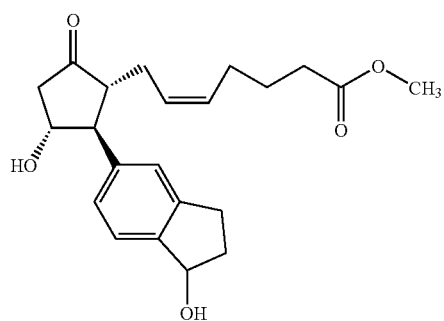
15-8 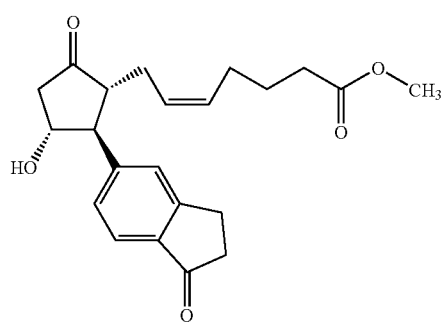
16-4 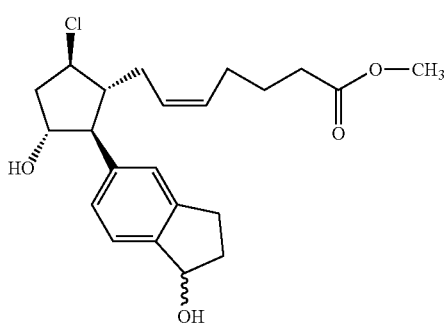
16-5 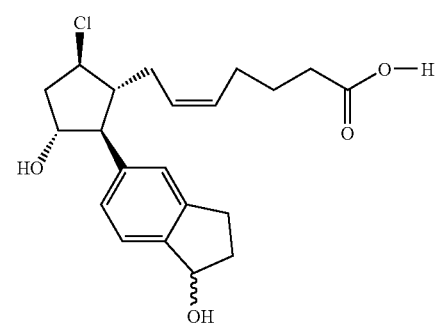
2281
16-8 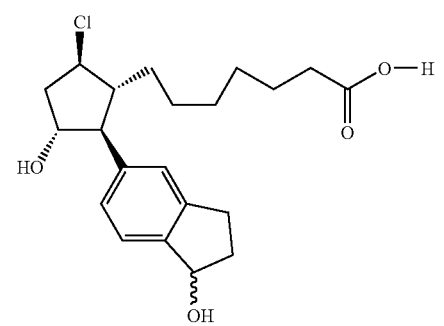
13139

-continued
16-7 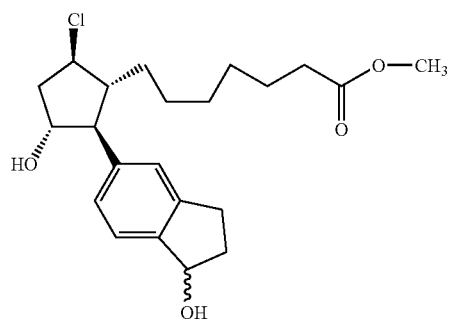
16-9 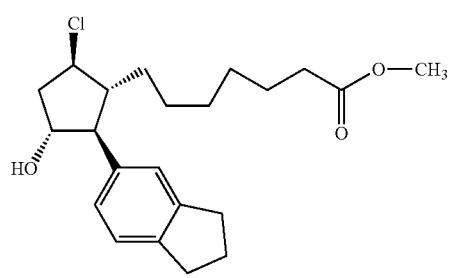 13100
16-10 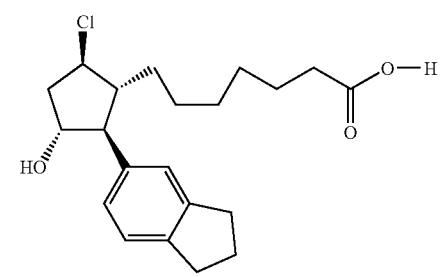 6251
e1-2 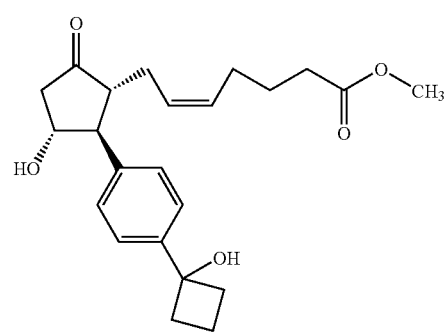
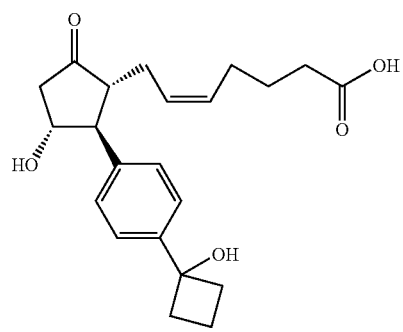

-continued
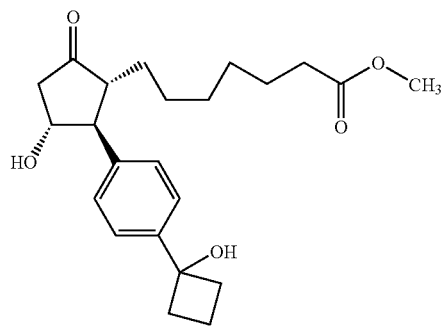
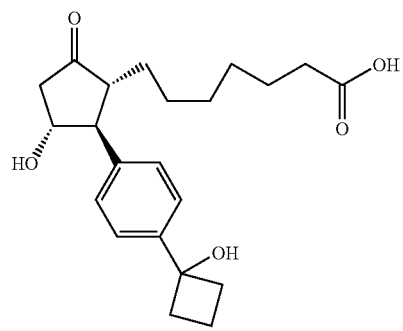
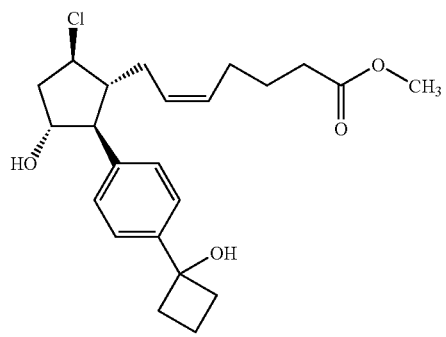
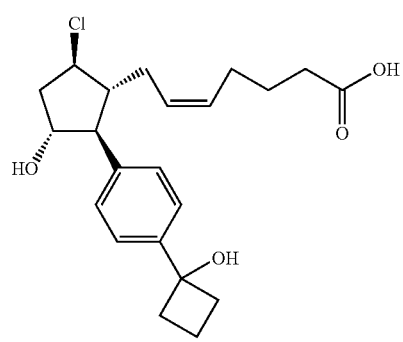

-continued
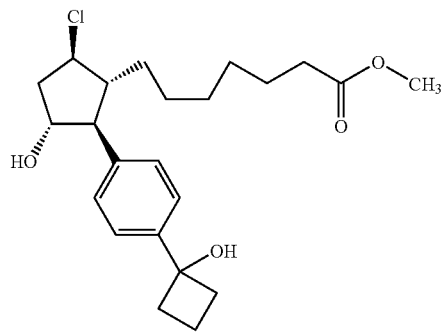
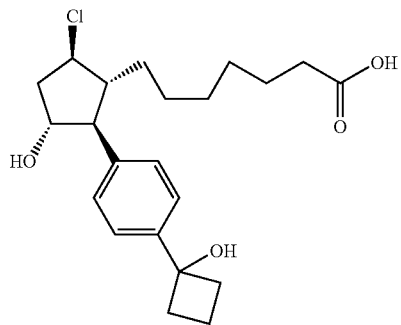
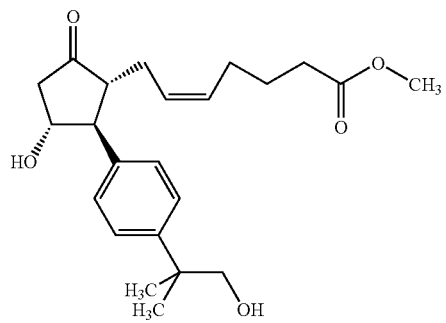
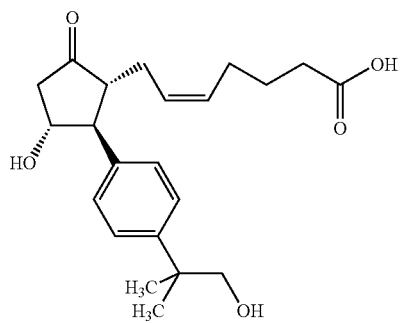

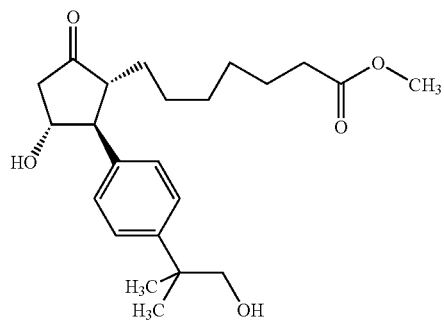
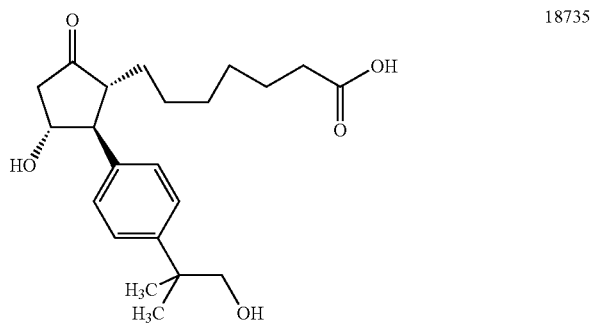
18735
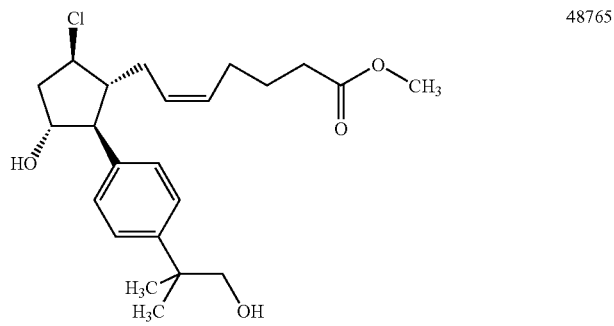
48765
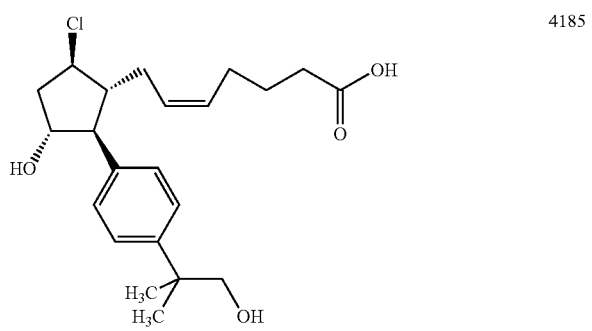
4185

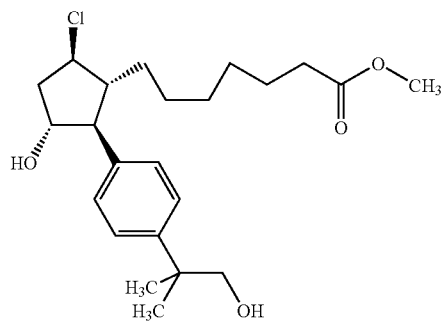
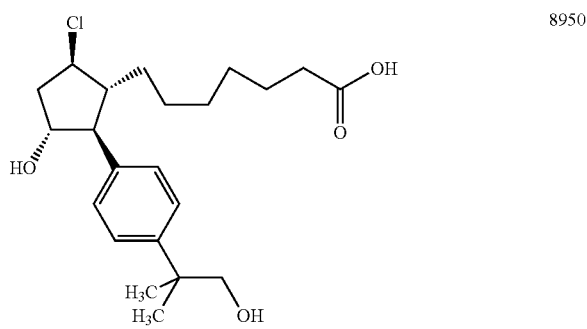
8950
7-5
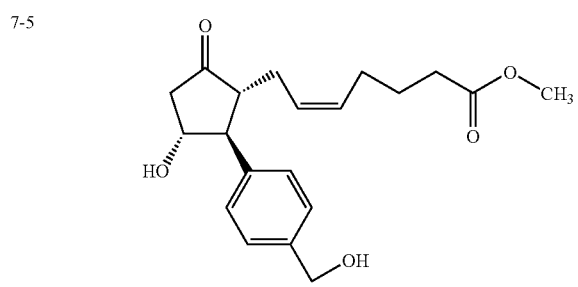
7-6
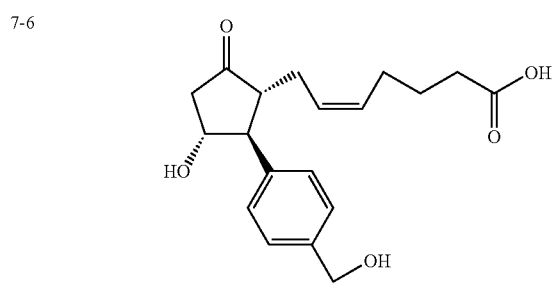
7-9
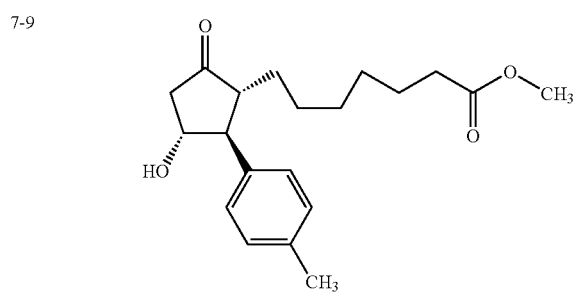

-continued
7-10
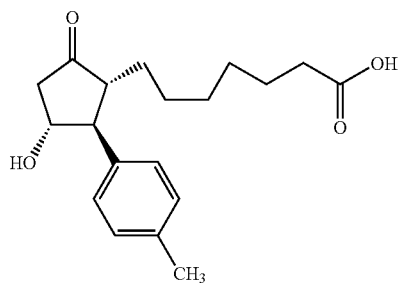
7-7
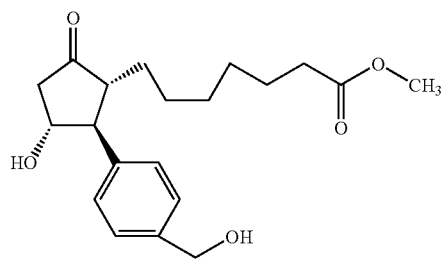
7-8
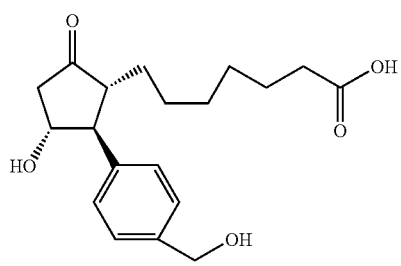
8-4
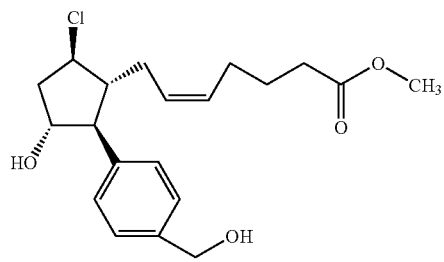
8-5
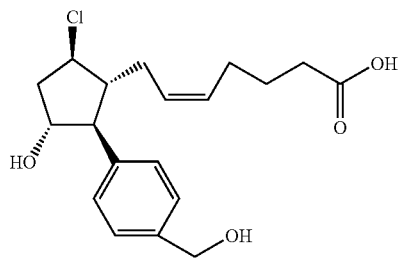
13150
8-6
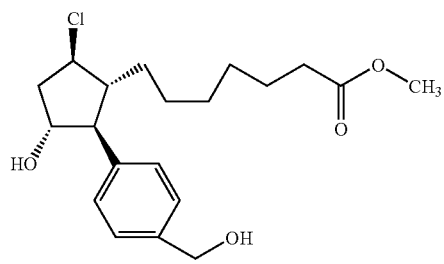

8-7
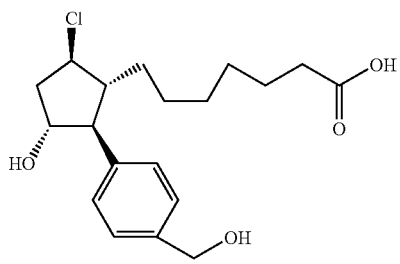
9-6
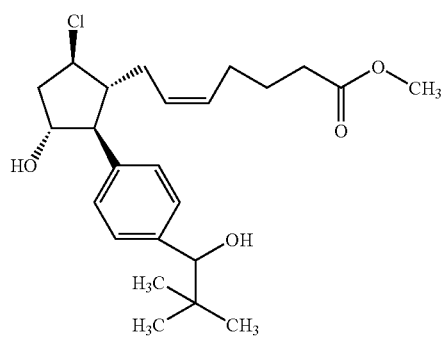
9-8
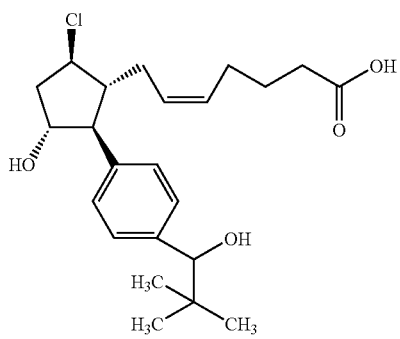
1537
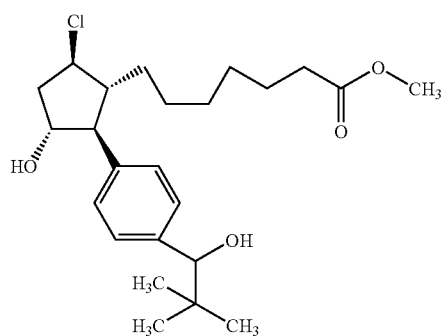

-continued
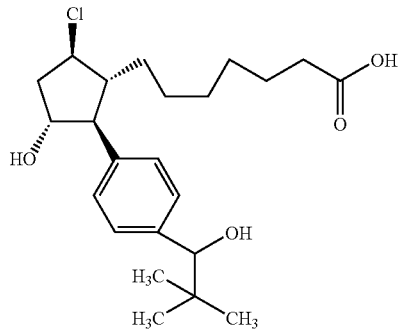
3630
9-5
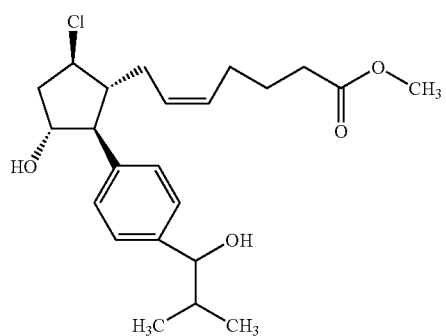
9-7
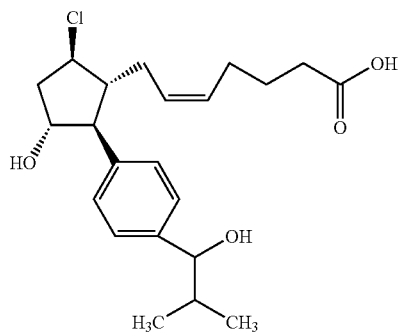
Ki
1340
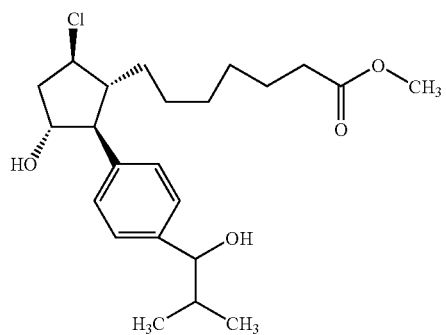

-continued
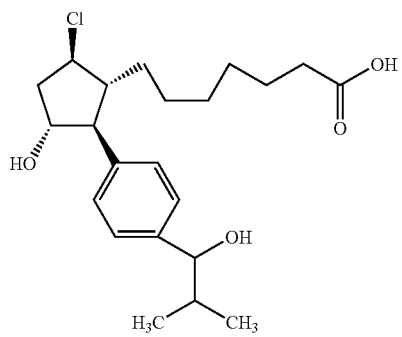
Ki
3022
| NUMBER | STRUCTURE | FUNCTIONAL EC50 (nm) | | | | | | | |
|--------|-----------|------|------|------|-------|------|-----|-----|-----|
| | | HFP | HEP1 | HEP2 | HEP3A | HEP4 | HTP | HIP | HDP |
| 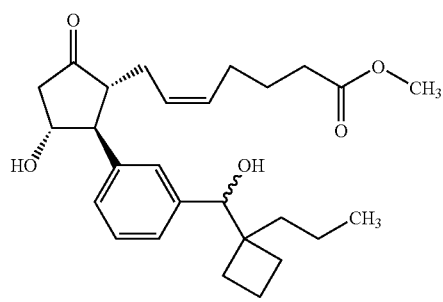 | | NA | NA | >10K | >10K | >10K | NA | NA | NA |
| 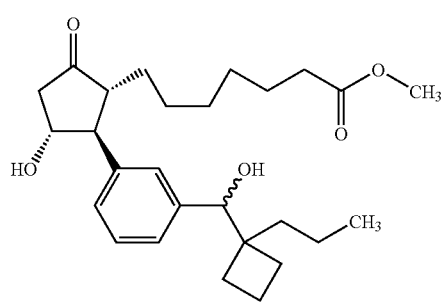 | | NA | NA | >10K | >10K | >10K | NA | >10K | >10K |
| 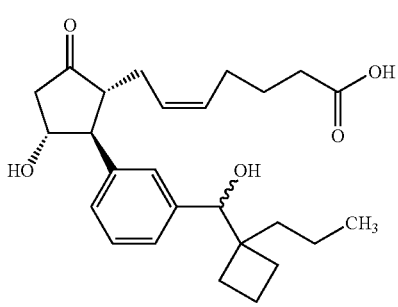 | | NA | NA | 5294 | 1698 | NA | NA | NA | NA |

| | | | | | | | | | |
|---|---|---|---|---|---|---|---|---|---|
| | 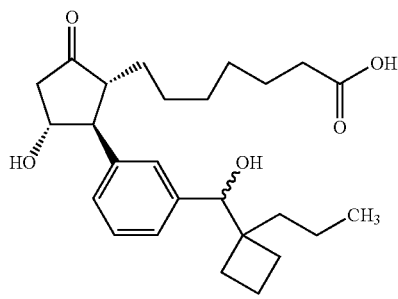 | NA | NA | 5259 | NA | NA | NA | NA | NA |
| e2-2 | 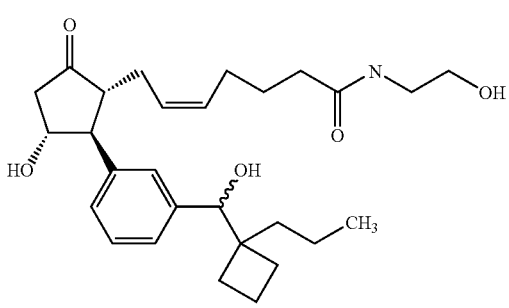 | NA | NA | NA | NA | NA | NA | NA | NA |
| e2-2 | 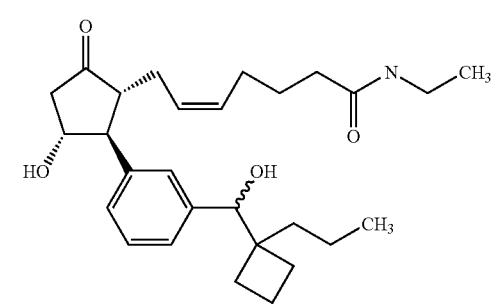 | NA | NA | >10K | NA | >10K | NA | NA | NA |
| e2-2 | 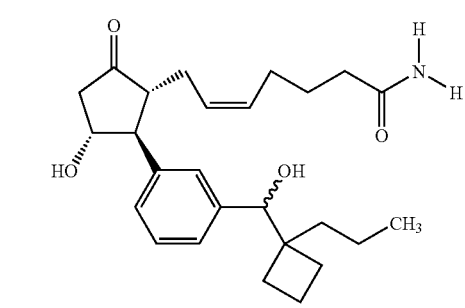 | NA | NA | NA | NA | NA | NA | NA | NA |
| | 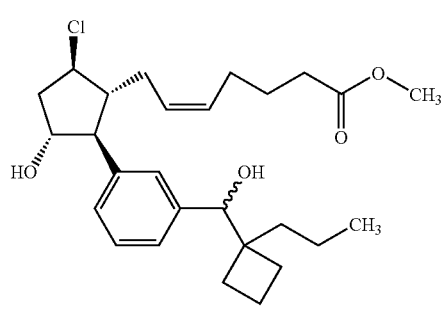 | NA | NA | >10K | >10K | NA | >10K | NA | NA |

-continued
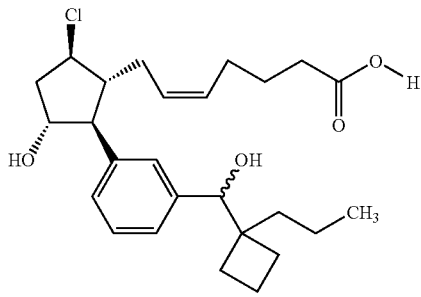
| NA | NA | 322 | 455 | NA | >10K | NA | >10K |
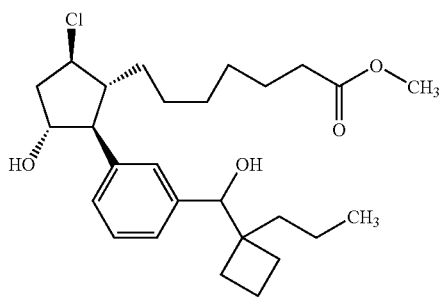
| NA | NA | NA | NA | NA | NA | NA | NA |
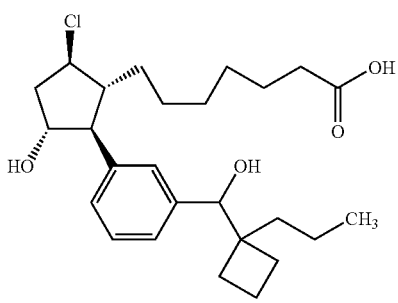
| NA | NA | 1479 | 3118 | NA | NA | NA | NA |
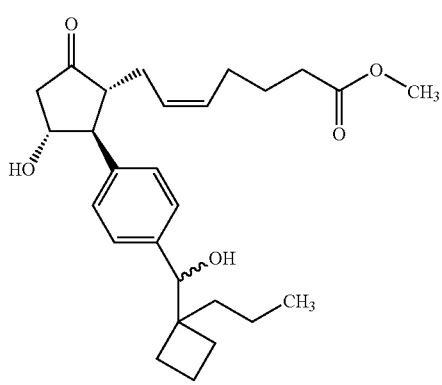
| NA | NA | NA | NA | NA | >10K | NA | NA |

-continued
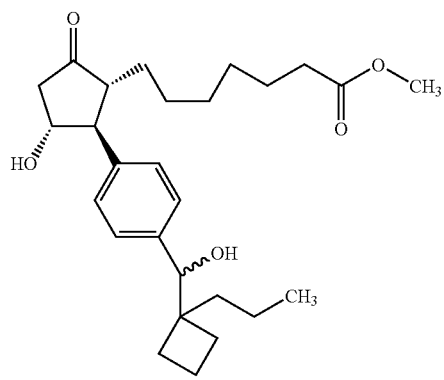
NA NA >10K NA NA NA NA NA
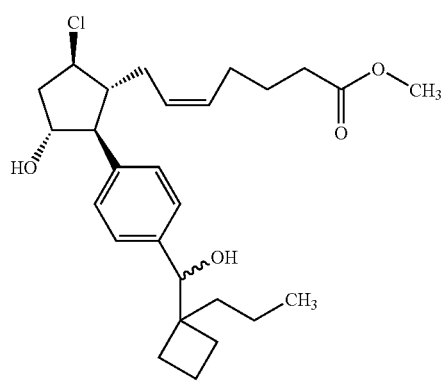
NA NA >10K NA NA NA NA NA
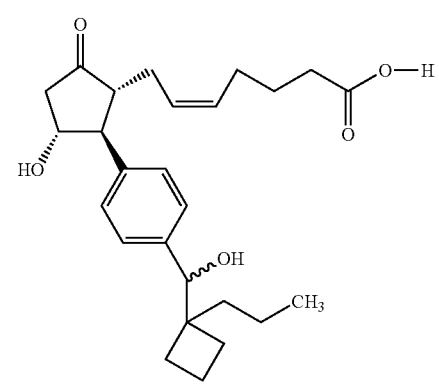
NA NA 3723 NA NA NA NA NA
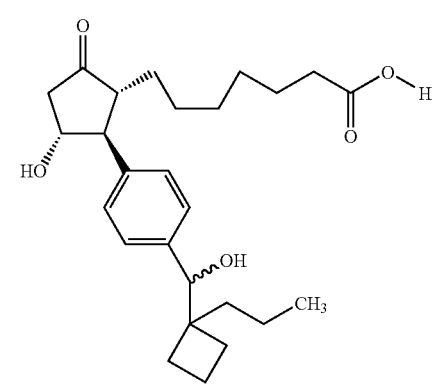
NA NA 635 NA NA NA NA NA -continued

| Structure | | | | | | | | |
|---|---|---|---|---|---|---|---|---|
| (chlorocyclopentane with phenyl-cyclobutyl-propyl group, pent-2-enoic acid chain) | NA | NA | 2270 | NA | NA | NA | NA | NA |
| (chlorocyclopentane with phenyl-cyclobutyl-propyl group, heptanoic acid methyl ester chain) | NA | NA | NA | NA | NA | NA | NA | NA |
| (chlorocyclopentane with phenyl-cyclobutyl-propyl group, heptanoic acid chain) | NA | NA | 546 | NA | NA | NA | NA | NA |
| (ketocyclopentane with t-butylphenyl group, hex-2-enoic acid methyl ester chain) | NA | NA | >10K | NA | NA | >10K | NA | NA |

| | | | | | | | |
|---|---|---|---|---|---|---|---|
| 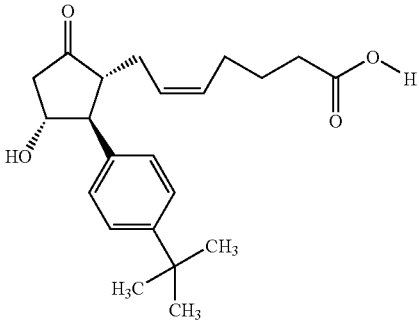 | NA | >10K | 1709 | NA | NA | NA | NA |
| 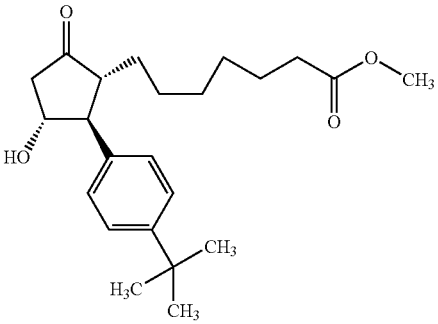 | NA | NA | 936 | >10K | >10K | >10K | NA |
| 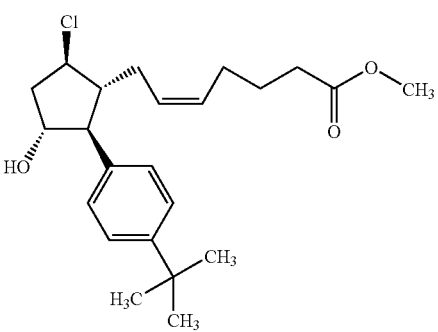 | NA | NA | >10K | >10K | NA | NA | NA |
| 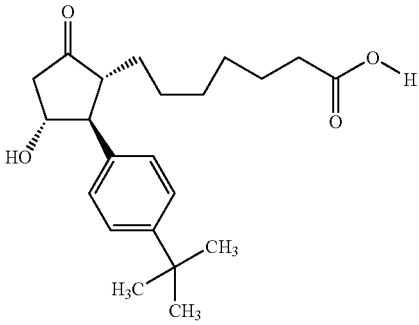 | NA | >10K | 102 | 3390 | NA | 4273 | >10K | NA |

-continued
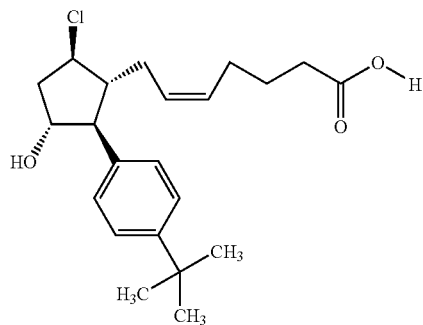 NA >10K 118 2053 >10K 1269 NA >10K
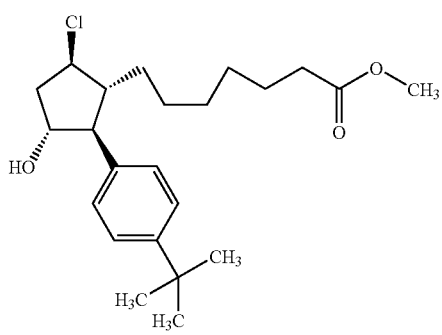 NA NA >10K NA NA NA NA NA
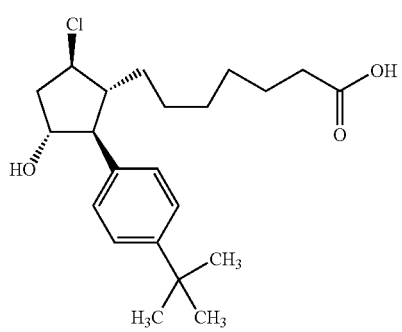 NA >10K 264 >10K NA >10K NA >10K
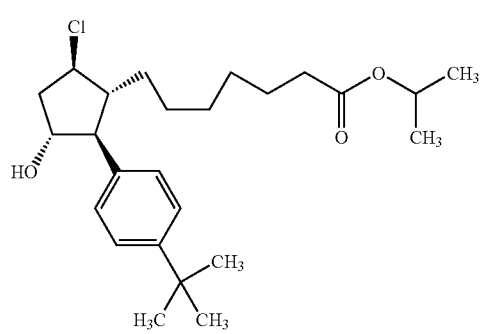 NA NA NA NA NA NA NA -continued
| | | | | | | | | | |
|---|---|---|---|---|---|---|---|---|---|
| 5-4 | 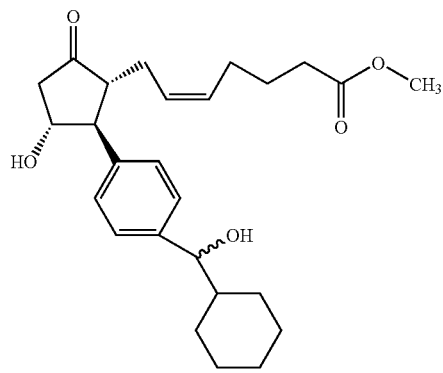 | NA | NA | >10K | NA | >10K | NA | NA | NA |
| 5-5 | 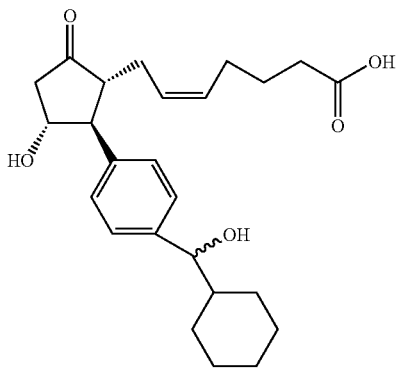 | NA | NA | >10K | NA | NA | NA | NA | NA |
| 5-7 | 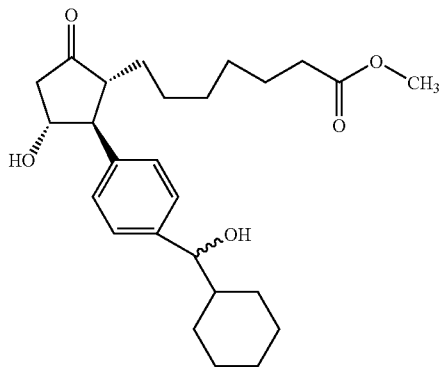 | NA | NA | >10K | NA | NA | NA | NA | NA |
| 5-8 | 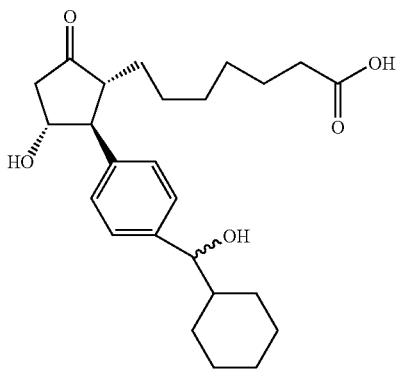 | NA | NA | 450 | NA | NA | NA | NA | NA |

-continued
| | | | | | | | | | |
|---|---|---|---|---|---|---|---|---|---|
| 6-3 | 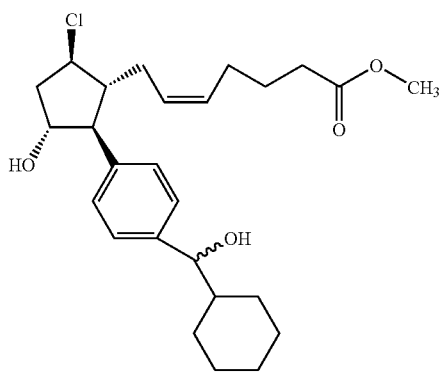 | NA | NA | >10K | NA | NA | NA | NA | NA |
| 6-4 | 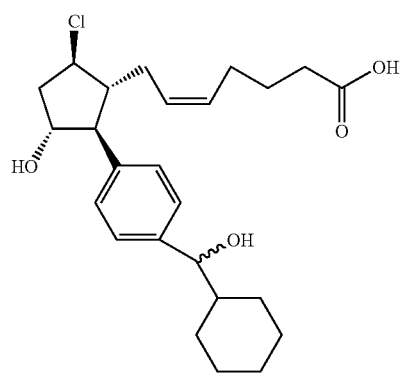 | NA | NA | 392 | NA | NA | NA | NA | NA |
| 6-6 | 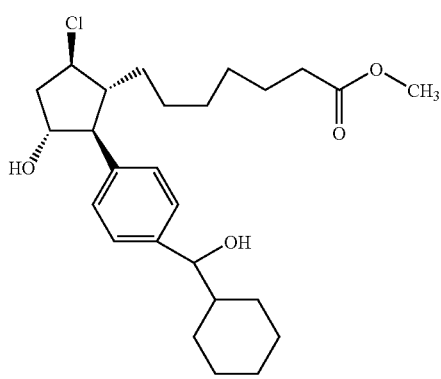 | NA | NA | NA | NA | NA | NA | NA | NA |
| 6-8 | 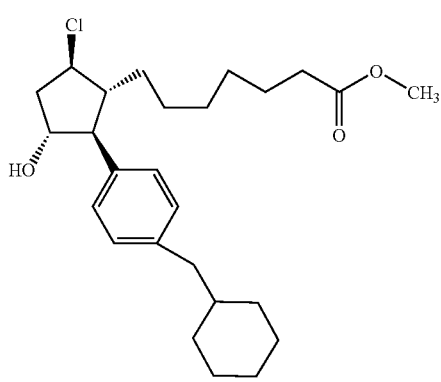 | NA | NA | NA | NA | NA | NA | NA | NA |

-continued
| | | | | | | | | | |
|---|---|---|---|---|---|---|---|---|---|
| 6-9 | 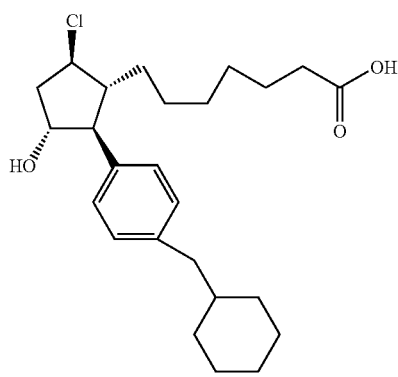 | NA | NA | 3445 | NA | NA | NA | NA | >10K |
| 6-7 | 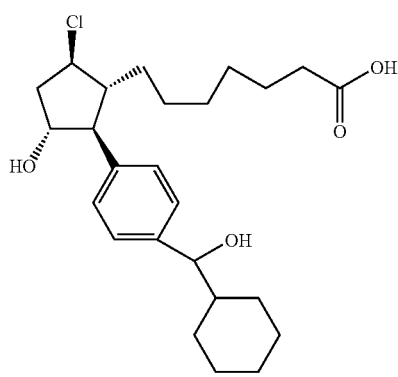 | NA | NA | 2813 | NA | NA | NA | NA | NA |
| 6-5 | 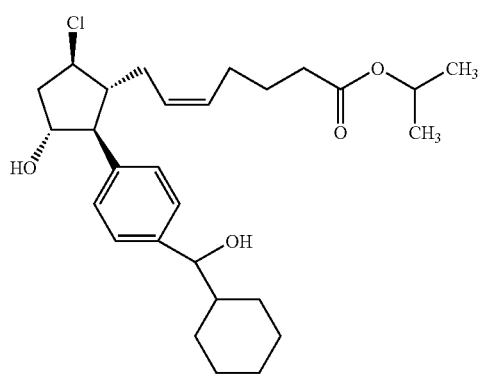 | NA | NA | NA | NA | NA | NA | NA | NA |
| 13-3 | 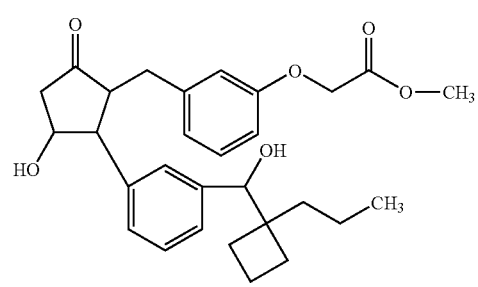 | NA | NA | NA | NA | NA | NA | NA | NA |

-continued

| | | | | | | | | | |
|---|---|---|---|---|---|---|---|---|---|
| 13-4 | (structure) | NA | NA | NA | NA | NA | NA | NA | >10K |
| 14-3 | (structure) | NA | NA | NA | NA | NA | NA | NA | |
| 14-4 | (structure) | NA | NA | 266 | NA | NA | NA | NA | |
| 11-2 | (structure) | NA | NA | 3844 | NA | NA | NA | NA | |
| 11-1 | (structure) | NA | NA | NA | NA | NA | NA | NA | NA |

-continued
| | | | | | | | | | |
|---|---|---|---|---|---|---|---|---|---|
| 11-3 | 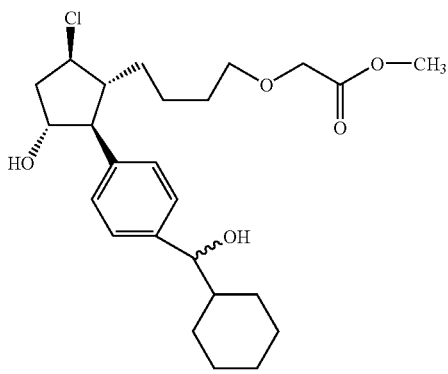 | NA | NA | NA | NA | NA | NA | NA | NA |
| 11-4 | 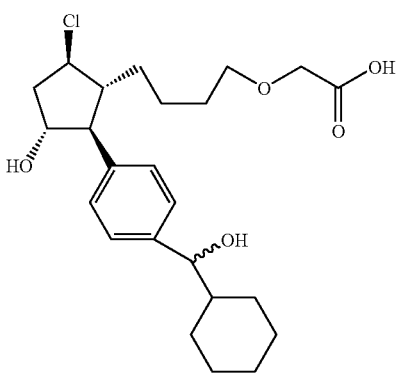 | NA | NA | 20773 | NA | NA | NA | NA | NA |
| 10-7 | 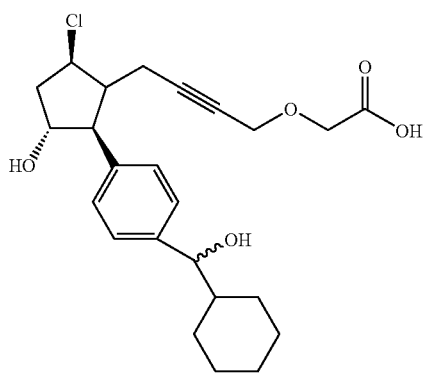 | NA | NA | 1550 | NA | NA | NA | NA | NA |
| 10-6 | 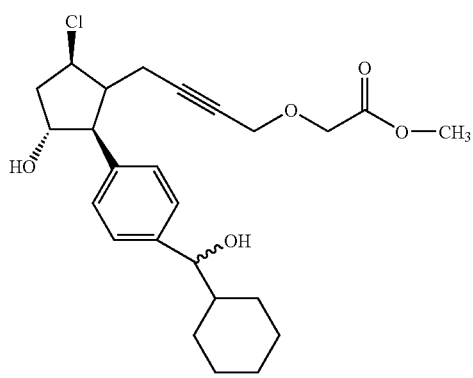 | NA | NA | NA | NA | NA | NA | NA | NA |

-continued
| | | | | | | | | | |
|---|---|---|---|---|---|---|---|---|---|
| 15-7 | 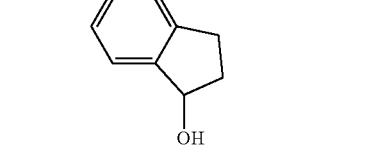 | NA | NA | NA | NA | NA | NA | NA | NA |
| 15-12 | 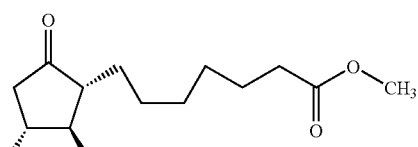 | NA | NA | >10K | >10K | >10K | >10K | NA | NA |
| 15-10 | 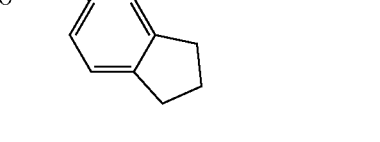 | NA | NA | NA | NA | NA | NA | NA | NA |
| 15-11 | 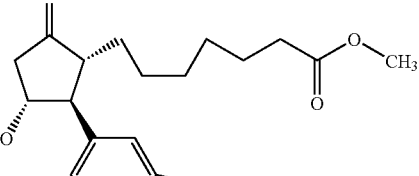 | NA | NA | NA | NA | >10K | NA | NA | |
| 15-6 | 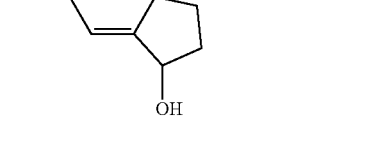 | NA | NA | NA | NA | NA | NA | NA | NA |

-continued

| | | | | | | | | | |
|---|---|---|---|---|---|---|---|---|---|
| 15-8 | (structure) | NA | NA | NA | NA | NA | NA | NA | NA |
| 16-4 | (structure) | | | NA | | NA | | | |
| 16-5 | (structure) | NA | NA | 405 | NA | NA | NA | NA | NA |
| 16-8 | (structure) | NA | NA | 529 | NA | NA | 2993 | NA | NA |
| 16-7 | (structure) | NA | NA | NA | NA | 22457 | 17525 | NA | NA |

-continued

| | | | | | | | | | |
|---|---|---|---|---|---|---|---|---|---|
| 16-9 | (structure) | NA | NA | NA | NA | NA | 506 | NA | NA |
| 16-10 | (structure) | NA | 221 | 818 | NA | NA | 200 | NA | |
| e1-2 | (structure) | NA | NA | NA | NA | NA | NA | NA | NA |
| | (structure) | NA | NA | >10K | NA | NA | NA | NA | NA |
| | (structure) | NA | NA | NA | NA | NA | NA | NA | NA |

-continued
| | | | | | | | |
|---|---|---|---|---|---|---|---|
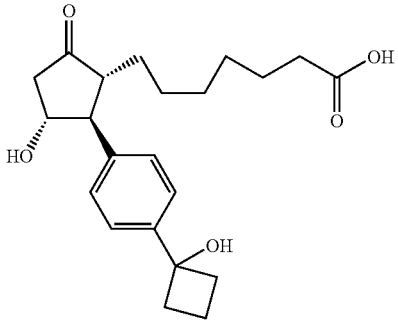
| NA | NA | >10K | NA | NA | NA | >10K | NA |
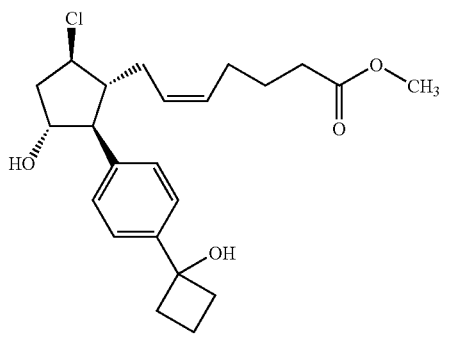
| NA | NA | >10K | NA | NA | NA | NA | NA |
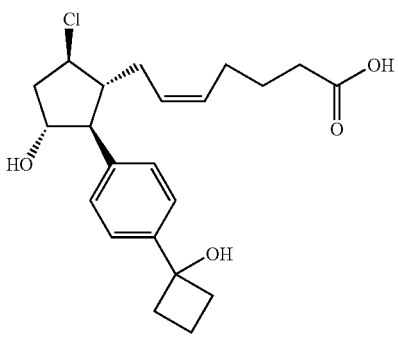
| NA | NA | 513 | NA | NA | >10K | NA | NA |
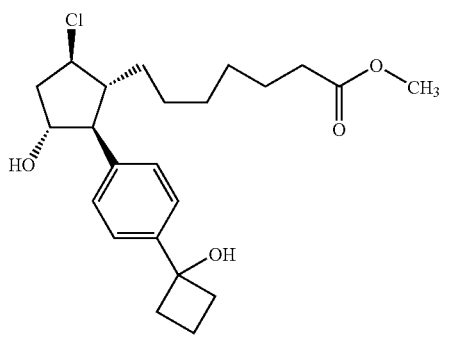
| NA | NA | >10K | NA | NA | >10K | NA | NA |

-continued

| | | | | | | | |
|---|---|---|---|---|---|---|---|
| NA | NA | 743 | NA | NA | >10K | NA | NA |
| | | NA | | >10K | | | |
| NA | NA | >10K | NA | | NA | NA | NA |
| NA | NA | >10K | NA | 26289 | NA | NA | NA |

-continued
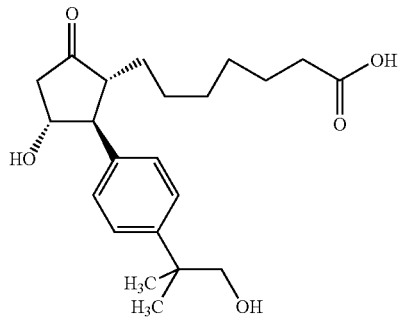
| | | | | | | | |
|---|---|---|---|---|---|---|---|
| NA | NA | 526 | NA | NA | NA | NA |
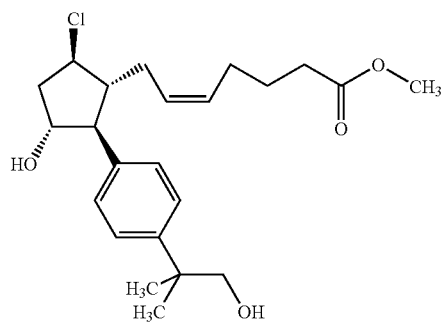
| | | | |
|---|---|---|---|
| >10K | >10K | | |
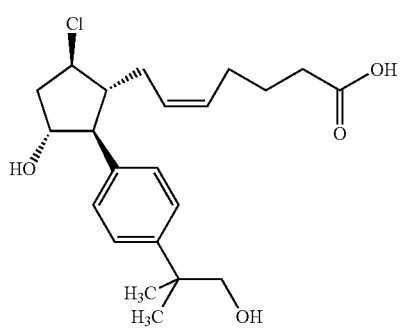
| | | | | | | |
|---|---|---|---|---|---|---|
| NA | NA | 173 | NA | NA | NA | NA |
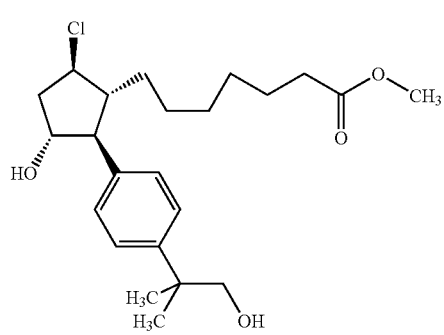
| | | | |
|---|---|---|---|
| >10K | >10K | | |

-continued

| | | | | | | | | | |
|---|---|---|---|---|---|---|---|---|---|
| | (structure with Cl, HO, OH, phenyl-C(CH₃)₂-CH₂OH, carboxylic acid chain) | NA | NA | 708 | NA | >10K | NA | NA | NA |
| 7-5 | (cyclopentanone, HO, phenyl-CH₂OH, methyl ester with cis-alkene) | | | NA | | NA | | | |
| 7-6 | (cyclopentanone, HO, phenyl-CH₂OH, carboxylic acid with cis-alkene) | | | NA | | NA | | | |
| 7-9 | (cyclopentanone, HO, p-tolyl, methyl ester) | NA | NA | >10K | NA | NA | NA | NA | NA |
| 7-10 | (cyclopentanone, HO, p-tolyl, carboxylic acid) | NA | 1873 | 3128 | NA | NA | 94 | NA | NA |

-continued
| | | | |
|---|---|---|---|
| 7-7 | 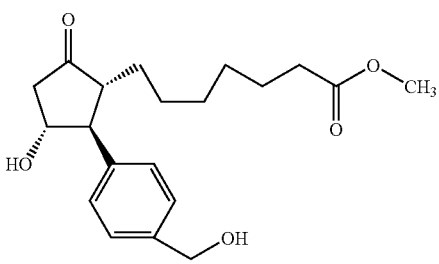 | NA | NA |
| 7-8 | 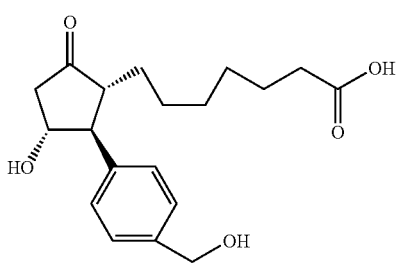 | NA | NA |
| 8-4 | 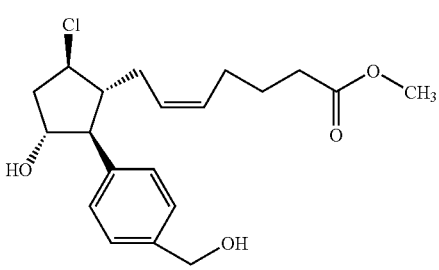 | >10K | NA |
| 8-5 | 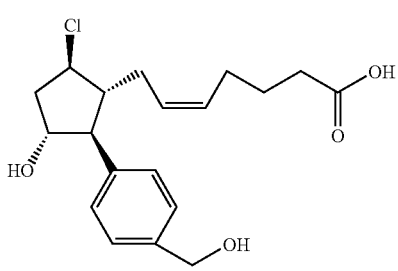 | NA NA NA NA NA NA NA | |
| 8-6 | 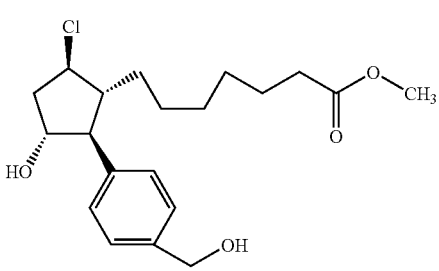 | NA | >10K |
| 8-7 | 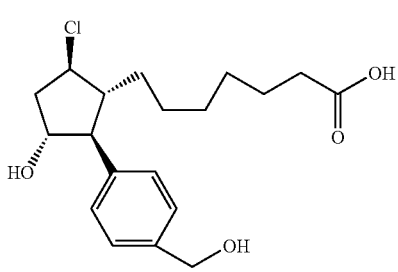 | >10K | NA |

-continued
| | | | | | | | | |
|---|---|---|---|---|---|---|---|---|
| 9-6 | 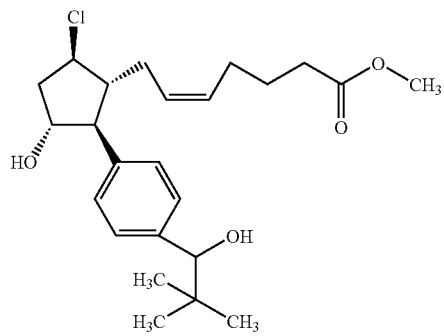 | NA | NA | 4995 | NA | >10K | NA | NA | NA |
| 9-8 | 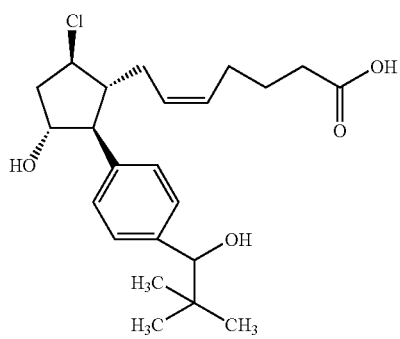 | NA | NA | 779 | NA | >10K | NA | NA | NA |
| | 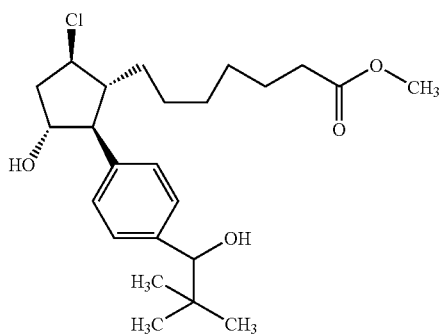 | NA | NA | 6575 | NA | >10K | NA | NA | NA |
| | 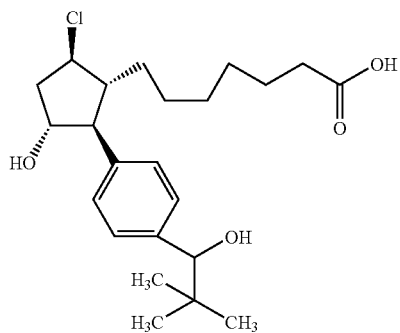 | NA | NA | 1265 | NA | >10K | NA | NA | NA |

-continued

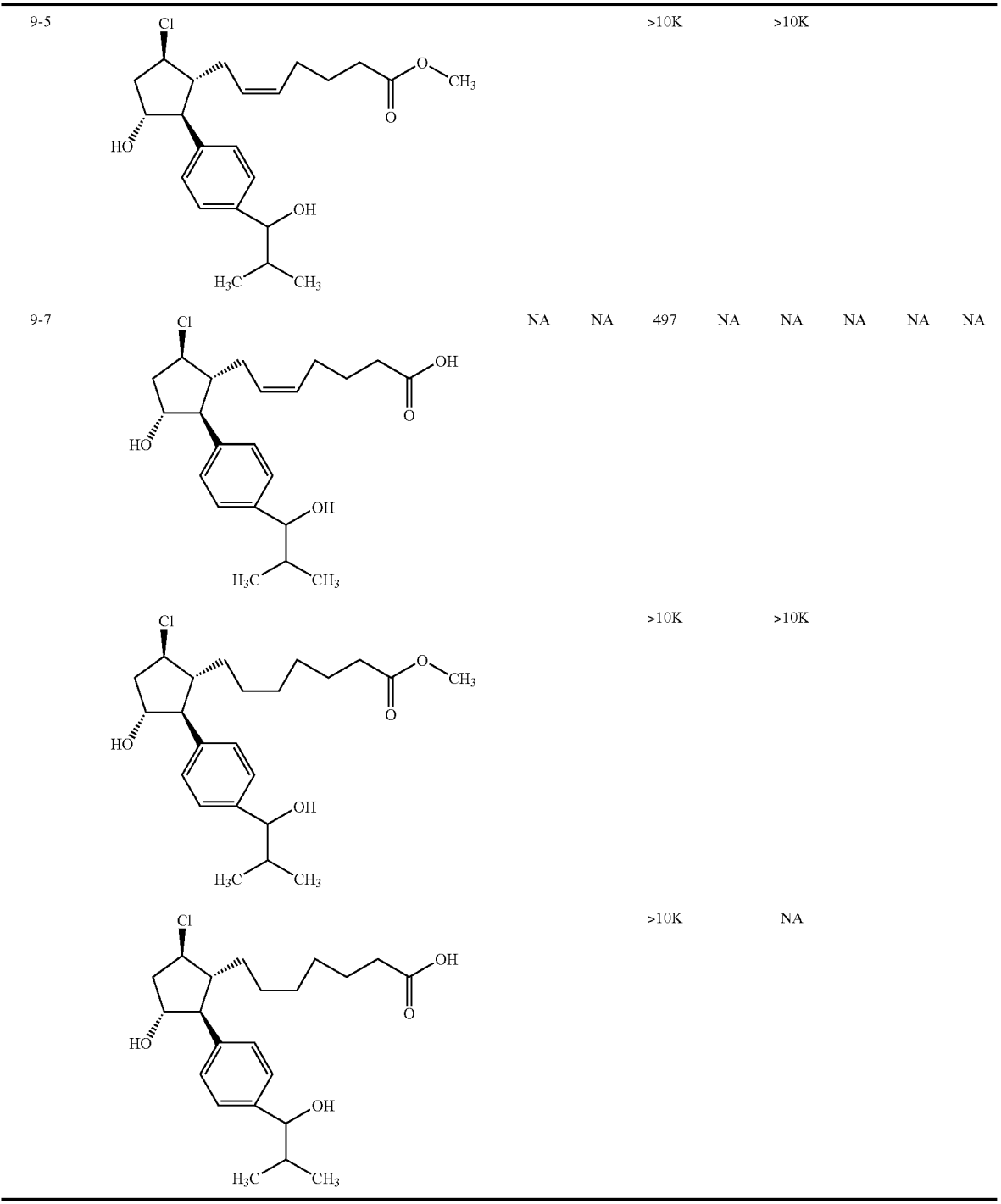

In Vivo Testing

Intraocular Pressure (IOP)

Intraocular pressure studies in dogs involved pneumatonometry performed in conscious, Beagle dogs of both sexes (10–15 kg). The animals remained conscious throughout the study and were gently restrained by hand. Drugs were administered topically to one eye as a 25 μL volume drop, the other eye received 25 μL vehicle (0.1% polysorbate 80:10 mM TRIS) as a control. Proparacaine (0.1%) was used for corneal anesthesia during tonometry. Intraocular pressure was determined just before drug administration and at 2, 4 and 6 hr thereafter on each day of the 5 day study. Drug was administered immediately after the first IOP reading.

Ocular Surface Hyperemia

Ocular surface hyperemia was visually assessed and scored according to a system typically used clinically.

| Hyperemia Score | Assigned Value |
|---|---|
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range. Similar tests were used to determine ocular surface hyperemia on monkeys and rabbits.

| NUMBER | STRUCTURE | Conc. (g/100 mL) | DOG Max. ΔIOP (mm Hg) | DOG Max. hyperemia | MONKEY Max. ΔIOP (mm Hg) | RABBIT Max. hyperemia |
|---|---|---|---|---|---|---|
| | *[cyclopentane with Cl, OH, 4-tert-butylphenyl, and hexanoic acid]* | 0.10% | −4 | 0.9 | | 0 |
| | *[cyclopentane with Cl, OH, 4-tert-butylphenyl, and isopropyl hexanoate]* | 0.01% | | | 8 | 0.1 |
| 6-4 | *[cyclopentane with Cl, OH, 4-(hydroxy(cyclohexyl)methyl)phenyl, and hexenoic acid]* | 0.10% | −4 | 1 | | 0 |

-continued

| NUMBER | STRUCTURE | Conc. (g/100 mL) | DOG Max. ΔIOP (mm Hg) | Max. hyperemia | MONKEY Max. ΔIOP (mm Hg) | RABBIT Max. hyperemia |
|---|---|---|---|---|---|---|
| 6-5 | 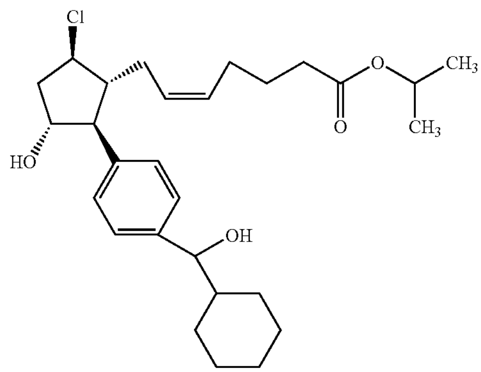 | 0.01% | −4 | 0.6 | 5 | |
| 16-5 | 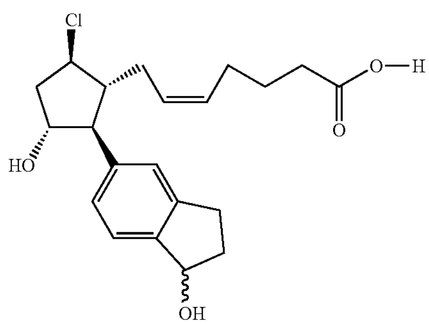 | 0.30% | −7 | 1 | 7 | |
| 16-6 | 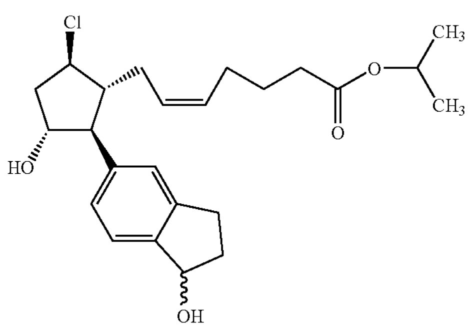 | 0.10% | −12 | | | 0.25 |
| | | 0.30% | −8 | 0.9 | | |

-continued

| NUMBER | STRUCTURE | Conc. (g/100 mL) | DOG Max. ΔIOP (mm Hg) | DOG Max. hyperemia | MONKEY Max. ΔIOP (mm Hg) | RABBIT Max. hyperemia |
|---|---|---|---|---|---|---|
| | | 0.10% | −5 | 0.7 | 6 | 0.1 |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

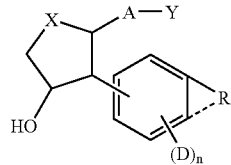

or a pharmaceutically acceptable salt or a prodrug thereof, wherein a dashed line represents the presence or absence of a covalent bond;

Y is a carboxylic acid, sulfonic acid, or phosphonic acid; or an amide or ester thereof having from 0 to 12 carbon atoms; or Y is a hydroxymethyl, or tetrazolyl functional group provided that when X is C=O, Y is not an amide of a carboxylic acid;

A is —(CH$_2$)$_6$—, cis—CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is substituted or unsubstituted phenyl or monocyclic heteroaryl, the sum of m and o is from 1 to 4, and wherein one CH$_2$ may be substituted with S or O;

X is C=O, CHF, CF$_2$, CHCl, or CHOH; wherein if X is CHOH, then OH is in the β-configuration;

R is a hydrocarbyl or a hydroxyhydrocarbyl moiety having from 1 to 12 carbon atoms;

D is independently a moiety having from 1 to 6 non-hydrogen atoms; and n is an integer from 0 to 4.

2. The compound of claim 1 wherein n is 0.

3. The compound of claim 1 wherein R has from 6 to 9 carbon atoms and a cyclic structure.

4. The compound of claim 3 wherein R is a 1-hydroxyhydrocarbyl moiety.

5. The compound of claim 1 wherein R has from 1 to 5 carbon atoms.

6. The compound of claim 5 wherein R consists of t-butyl.

7. The compound of claim 1 of the formula

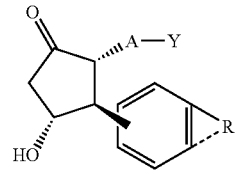

or a pharmaceutically acceptable salt, or a prodrug thereof.

8. The compound of claim 1 of the formula

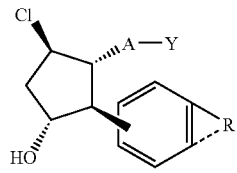

or a pharmaceutically acceptable salt, or a prodrug thereof.

9. The compound of claim 4 of the formula

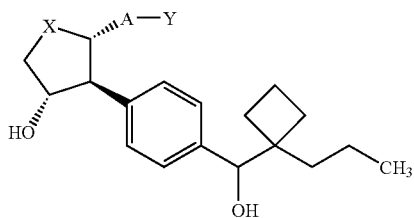

or a pharmaceutically acceptable salt, or a prodrug thereof.

10. The compound of claim 4 of the formula

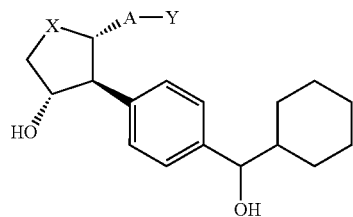

or a pharmaceutically acceptable salt, or a prodrug thereof.

11. The compound of claim 1 of the formula

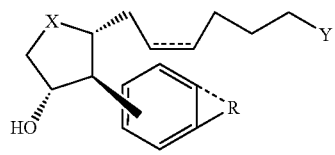

or a pharmaceutically acceptable salt, or a prodrug thereof.

12. The compound of claim 11 of the formula

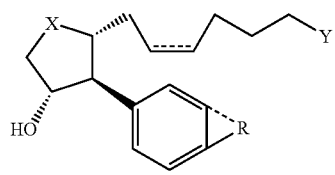

wherein X is C=O or CHCl; and
R is alkyl having from 3 to 6 carbon atoms.

13. The compound of claim 11 of the formula

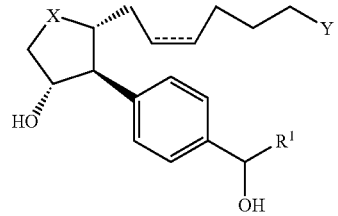

or a pharmaceutically acceptable salt, or a prodrug thereof, wherein $R^1$ is a cycloalkyl having from 3 to 10 carbon atoms; and X is C=O or CHCl.

14. The compound of claim 13 of the formula

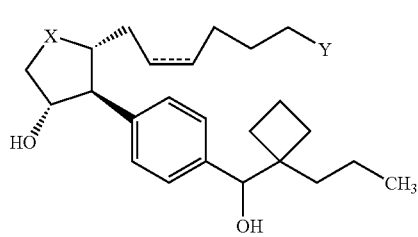

or a pharmaceutically acceptable salt, or a prodrug thereof.

15. The compound of claim 13 of the formula

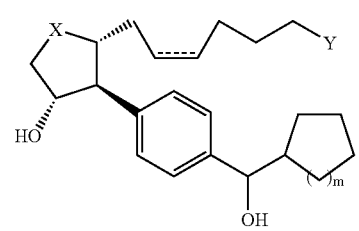

or a pharmaceutically acceptable salt, or a prodrug thereof
wherein m is an integer having a value of from 0 to 3.

16. The compound of claim 15 of the formula

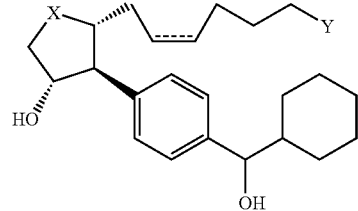

or a pharmaceutically acceptable salt, or a prodrug thereof.

17. The compound of claim 12 of the formula

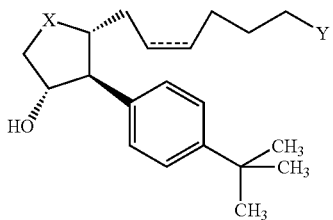

or a pharmaceutically acceptable salt, or a prodrug thereof.

18. The compound of claim 11 of the formula

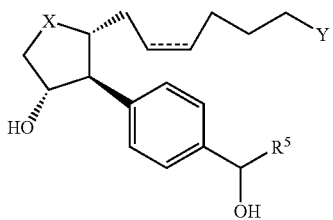

or a pharmaceutically acceptable salt, or a prodrug thereof,
wherein $R^6$ is branched alkyl having from 3 to 10 carbon atoms; and
X is C=O or CHCl.

19. The compound of claim 11 selected from the group consisting of (Z)-7-{(1R,2S,3R)-2-[4-(Cyclohexyl-hydroxy-methyl)-phenyl]-3-hydroxy-5-oxo-cyclopentyl}-hept-5-enoic acid methyl ester;

(Z)-7-{(1R,2S,3R)-2-[4-(Cyclohexyl-hydroxy-methyl)-phenyl]-3-hydroxy-5-oxo-cyclopentyl}-hept-5-enoic acid;

7-{(1R,2S,3R)-2-[4-(Cyclohexyl-hydroxy-methyl)-phenyl]-3-hydroxy-5-oxo-cyclopentyl}-heptanoic acid methyl ester;

7-{(1R,2S,3R)-2-[4-(Cyclohexyl-hydroxy-methyl)-phenyl]-3-hydroxy-5-oxo-cyclopentyl]-heptanoic acid;

(Z)-7-((1R,2S,3R)-3-Hydroxy-2-{4-[hydroxy-(1-propyl-cyclobutyl)-methyl]-phenyl}-5-oxo-cyclopentyl)-hept-5-enoic acid methyl ester;

(Z)-7-((1R,2S,3R)-3-Hydroxy-2-{4-[hydroxy-(1-propyl-cyclobutyl)-methyl]-phenyl}-5-oxo-cyclopentyl)-hept-5-enoic acid;

7-((1R,2S,3R}3-Hydroxy-2-{4-[hydroxy-(1-propyl-cyclobutyl)-methyl]-phenyl}-5-oxo-cyclopentyl)-heptanoic acid methyl ester;

7-((1R,2S,3R)-3-Hydroxy-2-{4-[hydroxy-(1-propyl-cyclobutyl)-methyl]-phenyl}-5-oxo-cyclopentyl)-heptanoic acid;

(Z)-7-[(1R,2S,3R)-2-(4-tert-Butyl-phenyl)-3-hydroxy-5-oxo-cyclopentyl]-hept-5-enoic acid methyl ester;

(Z)-7-[(1R,2S,3R)-2-(4-tert-Butyl-phenyl)-3-hydroxy-5-oxo-cyclopentyl]-hept-5-enoic acid;

7-[(1R,2S,3R)-2-(4-tert-Butyl-phenyl)-3-hydroxy-5-oxo-cyclopentyl]-heptanoic acid methyl ester;

7-[(1R,2S,3R)-2-(4-tert-Butyl-phenyl)-3-hydroxy-5-oxo-cyclopentyl]-heptanoic acid;

(Z)-7-{(1R,2S,3R}3-Hydroxy-2-[4-(2-hydroxy-1,1-dimethyl-ethyl)-phenyl]-5-oxo-cyclopentyl}-hept-5-enoic acid methyl ester;

(Z)-7-{(1R,2S,3R)-3-Hydroxy-2-[4-(2-hydroxy-1,1-dimethyl-ethyl)-phenyl]-5-oxo-cyclopentyl}-hept-5-enoic acid;

7-{(1R,2S,3R)-3-Hydroxy-2-[4 (2-hydroxy-1,1-dimethyl-ethyl)-phenyl]-5-oxo-cyclopentyl}-heptanoic acid methyl ester;

7-{(1R,2S,3R)-3-Hydroxy-2-[4-(2-hydroxy-1,1-dimethylethyl)-phenyl]-5-oxo-cyclopentyl}-heptanoic acid;

(Z)-7-{(1R,2S,3R)-3-Hydroxy-2-[4-(1-hydroxy-cyclobutyl)-phenyl]-5-oxo-cyclopentyl}-hept-5-enoic acid methyl ester;

7-{(1R,2S,3R)-3-Hydroxy-2-[4-(1-hydroxy-cyclobutyl)-phenyl]-5-oxo-cyclopentyl}-heptanoic acid methyl ester;

7-{(1R,2S,3R)-3-Hydroxy-2-[4-(1-hydroxy-cyclobutyl)-phenyl]-5-oxo-cyclopentyl}-heptanoic acid;

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid methyl ester;

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid;

7-((1R,2S,3R)-3-Hydroxy-2-{3-[hydroxy-(1-propyl-cyclobutyl)-methyl]-phenyl}-5-oxo-cyclopentyl)-heptanoic acid methyl ester;

7-((1R,2S,3R)-3-Hydroxy-2-{3[hydroxy-(1-propyl-cyclobutyl)-methyl]-phenyl}-5-oxo-cyclopentyl)-heptanoic acid;

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid (2-hydroxy-ethyl)-amide;

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid ethyl amide;

(Z)-7-((1R,2S,3R)-3-Hydroxy-2-{3-[hydroxy-(1-propyl-cyclobutyl)-methyl]-phenyl}-5-oxo-cyclopentyl)-hept-5-enoic acid ethyl amide;

(Z)-7-{(1R,2S,3R,5R)-5-Chloro-2-[4-(cyclohexyl-hydroxy-methyl)-phenyl]-3-hydroxy-cyclopentyl}-hept-5-enoic acid methyl ester;

(Z)-7-{(1R,2S,3R,5R)-5-Chloro-2-[4-(cyclohexyl-hydroxy-methyl)-phenyl]-3-hydroxy-cyclopentyl}-hept-5-enoic acid;

(Z)-7-{(1R,2S,3R,5R)-5-Chloro-2-[4-(cyclohexyl-hydroxy-methyl)-phenyl]-3-hydroxy-cyclopentyl}-hept-5-enoic acid isopropyl ester;

7-{(1R,2S,3R,5R)-5-Chloro-2-[4-(cyclohexyl-hydroxy-methyl)-phenyl]-3-hydroxy-cyclopentyl}-heptanoic acid methyl ester;

7-[(1R,2S,3R,5R)-5-Chloro-2-(4-cyclohexylmethyl-phenyl)-3-hydroxy-cyclopentyl]-heptanoic acid methyl ester;

7-{(1R,2S,3R,5R)-5-Chloro-2-[4-(cyclohexyl-hydroxy-methyl)-phenyl]-3-hydroxy-cyclopentyl}-heptanoic acid;

7-[(1R,2S,3R,5R)-5-Chloro-2-(4-cyclohexylmethyl-phenyl)-3-hydroxy-cyclopentyl]-heptanoic acid;

(Z)-7-((1R,2S,3R,5R)-5-Chloro-3-hydroxy-2-{3-[hydroxy-(1-propyl-cyclobutyl)-methyl]-phenyl}-cyclopentyl)-hept-5-enoic acid methyl ester;

(Z)-7-((1R,2S,3R,5R)-5-Chloro-3-hydroxy-2-{3-[hydroxy-(1-propyl-cyclobutyl)-methyl]-phenyl}-cyclopentyl)-hept-5-enoic acid;

7-((1R,2S,3R,5R)-5-Chloro-3-hydroxy-2-{3-[hydroxy-(1-propyl-cyclobutyl)-methyl]-phenyl}-cyclopentyl)-heptanoic acid methyl ester;

7-((1R,2S,3R,5R)-5-Chloro-3-hydroxy-2-{3-[hydroxy-(1-propyl-cyclobutyl)-methyl]-phenyl}-cyclopentyl)-heptanoic acid;

(Z)-7-((1R,2S,3R,5R)-5-Chloro-3-hydroxy-2-{4-[hydroxy-(1-propyl-cyclobutyl)-methyl]-phenyl}-cyclopentyl)-hept-5-enoic acid methyl ester;

(Z)-7-((1R,2S,3R,5R)-5-Chloro-3-hydroxy-2-{4-[hydroxy-(1-propyl-cyclobutyl)-methyl]-phenyl}-cyclopentyl)-hept-5-enoic acid;

7-((1R,2S,3R,5R)-5-Chloro-3-hydroxy-2-{4-[hydroxy-(1-propyl-cyclobutyl)-methyl]-phenyl}-cyclopentyl)-heptanoic acid methyl ester;

7-((1R,2S,3R,5R)-5-Chloro-3-hydroxy-2-{4-hydroxy-(1-propyl-cyclobutyl)-methyl]-phenyl}-cyclopentyl)-heptanoic acid;

(Z)-7-[(1R,2S,3R,5R)-2-(4-tert-Butyl-phenyl)-5-chloro-3-hydroxy-cyclopentyl]-hept-5-enoic acid methyl ester;

(Z)-7-[(1R,2S,3R,5R)-2-(4-tert-Butyl-phenyl)-5-chloro-3-hydroxy-cyclopentyl]-hept-5-enoic acid;

7-[(1R,2S,3R,5R)-2-(4-tert-Butyl-phenyl)-5-chloro-3-hydroxy-cyclopentyl]-heptanoic acid methyl ester;

7-[(1R,2S,3R,5R)-2-(4-tert-Butyl-phenyl)-5-chloro-3-hydroxy-cyclopentyl]-heptanoic acid;

(Z)-7-[(1R,2S,3R,5R)-2-(4-tert-Butyl-phenyl)-5-chloro-3-hydroxy-cyclopentyl]-hept-5-enoic acid isopropyl ester;

(Z)-7-{(1R,2S,3R,5R)-5-Chloro-3-hydroxy-2-[4-(1-hydroxy-cyclobutyl)-phenyl]-cyclopentyl}-hept-5-enoic acid methyl ester;

(Z)-7-{(1R,2S,3R,5R)-5-Chloro-3-hydroxy-2-[4-(1-hydroxy-cyclobutyl)-phenyl]-cyclopentyl}-hept-5-enoic acid;

7-{(1R,2S,3R,5R)-5-Chloro-3-hydroxy-2-[4-(1-hydroxy-cyclobutyl)-phenyl]-cyclopentyl}-heptanoic acid methyl ester;

7-{(1R,2S,3R,5R)-5-Chloro-3-hydroxy-2-[4-(1-hydroxy-cyclobutyl)-phenyl]-cyclopentyl}-heptanoic acid;

(Z)-7-{(1R,2S,3R,5R)-5-Chloro-3-hydroxy-2-[4-(2-hydroxy-1,1-dimethylethyl)-phenyl]-cyclopentyl}-hept-5-enoic acid methyl ester;

(Z)-7-{(1R,2S,3R,5R)-5-Chloro-3-hydroxy-2-[(4-(2-hydroxy-1,1-dimethyl-ethyl)-phenyl]-cyclopentyl}-hept-5-enoic acid;

7-{(1R,2S,3R,5R)-5-Chloro-3-hydroxy-2-[4-(2-hydroxy-1,1-dimethyl-ethyl)-phenyl]-cyclopentyl}-heptanoic acid methyl ester;

7-{(1R,2S,3R,5R)-5-Chloro-3-hydroxy-2-[4-(2-hydroxy-1,1-dimethyl-ethyl)-phenyl]-cyclopentyl}-heptanoic acid;

7-{(1R,2S,3R,5R)-5-Chloro-3-hydroxy-2-[4-(2-hydroxy-1,1-dimethyl-ethyl)-phenyl]-cyclopentyl}-heptanoic acid isopropyl ester;

(Z)-7-[(1R,2S,3R)-3-Hydroxy-2-(4-hydroxymethyl-phenyl)-5-oxo-cyclopentyl]-hept-5-enoic acid methyl ester;

(Z)-7-[(1R,2S,3R)-3-Hydroxy-2-(4-hydroxymethyl-phenyl)-5-oxo-cyclopentyl]-hept-5-enoic acid;

7-[(1R,2S,3R)-3-Hydroxy-2-(4-hydroxymethyl-phenyl)-5-oxo-cyclopentyl]-heptanoic acid methyl ester;

7-((1R,2S,3R)-3-Hydroxy-5-oxo-2-p-tolyl-cyclopentyl)-heptanoic acid methyl ester;

7-[(1R,2S,3R)-3-Hydroxy-2-(4-hydroxymethyl-phenyl)-5-oxo-cyclopentyl]-heptanoic acid;

(Z)-7-[(1R,2S,3R,5R)-5-Chloro-3-hydroxy-2-(4-hydroxymethyl-phenyl)-cyclopentyl]-hept-5-enoic acid methyl ester;

(Z)-7-[(1R,2S,3R,5R)-5-Chloro-3-hydroxy-2-(4-hydroxymethyl-phenyl)-cyclopentyl]-hept-5-enoic acid;

7-[(1R,2S,3R,5R)-5-Chloro-3-hydroxy-2-(4-hydroxymethyl-phenyl)-cyclopentyl]-heptanoic acid methyl ester;

7-[(1R,2S,3R,5R)-5-Chloro-3-hydroxy-2-(4-hydroxymethyl-phenyl)-cyclopentyl]-heptanoic acid;

(Z)-7-{(1R,2S,3R,5R)-5-Chloro-3-hydroxy-2-[4-(1-hydroxy-2-methyl-propyl)-phenyl]-cyclopentyl}-hept-5-enoic acid methyl ester;

(Z)-7-{(1R,2S,3R,5R)-5-Chloro-3-hydroxy-2-[4-(1-hydroxy-2,2-dimethyl-propyl)-phenyl]-cyclopentyl}-hept-5-enoic acid methyl ester;

(Z)-7-{(1R,2S,3R,5R)-5-Chloro-3-hydroxy-2-[4-(1-hydroxy-2-methyl-propyl)-phenyl]-cyclopentyl}-hept-5-enoic acid;

(Z)-7-{(1R,2S,3R,5R)-5-Chloro-3-hydroxy-2-[4-(1-hydroxy-2,2-dimethyl-propyl)-phenyl]-cyclopentyl}-hept-5-enoic acid;

7-{(1R,2S,3R,5R)-5-Chloro-3-hydroxy-2-[4-(1-hydroxy-2-methyl-propyl)-phenyl]-cyclopentyl}-heptanoic acid methyl ester;

7-{(1R,2S,3R,5R)-5-Chloro-3-hydroxy-2-[4-(1-hydroxy-2,2-dimethyl-propyl)-phenyl]-cyclopentyl}-heptanoic acid methyl ester;

7-{(1R,2S,3R,5R)-5-Chloro-3-hydroxy-2-[4-(1-hydroxy-2-methyl-propyl)-phenyl]-cyclopentyl}-heptanoic acid;

7-{(1R,2S,3R,5R)-5-Chloro-3-hydroxy-2-[4-(1-hydroxy-2,2-dimethyl-propyl)-phenyl]-cyclopentyl}-heptanoic acid;

(4-{(1R,2S,3R,5R)-5-Chloro-2-[4-(cyclohexyl-hydroxy-methyl)-phenyl]-3-hydroxy-cyclopentyl}-but-2-enyloxy)-acetic acid methyl ester;

(4-{(1R,2S,3R,5R)-5-Chloro-2-[4-(cyclohexyl-hydroxy-methyl)-phenyl]-3-hydroxy-cyclopentyl}-but-2-ynyloxy)-acetic acid;

((Z)-4-{(1R,2S,3R,5R)-5-Chloro-2-[4-(cyclohexyl-hydroxy-methyl)-phenyl]-3-hydroxy-cyclopentyl}-but-2-enyloxy)-acetic acid methyl ester;

((Z)-4-{(1R,2S,3R,5R)-5-Chloro-2-[4-(cyclohexyl-hydroxy-methyl)-phenyl]-3-hydroxy-cyclopentyl}-but-2-enyloxy)-acetic acid;

(4-{(1R,2S,3R,5R)-5-Chloro-2-[(4-(cyclohexyl-hydroxy-methyl)-phenyl]-3-hydroxy-cyclopentyl}-butoxy)-acetic acid methyl ester;

(4-{(1R,2S,3R,5R)-5-Chloro-2-[4-(cyclohexyl-hydroxy-methyl)-phenyl]-3-hydroxy-cyclopentyl}-butoxy)-acetic acid;

[3-((1R,2S,3R)-3-Hydroxy-2-{3-[(S)-hydroxy-(1-propyl-cyclobutyl)-methyl]-phenyl}-5-oxo-cyclopentylmethyl)-phenoxy]-acetic acid methyl ester;

[3-((1R,2S,3R)-3-Hydroxy-2-{3-[(S)-hydroxy-(1-propyl-cyclobutyl)-methyl]-phenyl}-5-oxo-cyclopentylmethyl)-phenoxy]-acetic acid;

[3-((1R,2S,3R,5R)-5-Chloro-3-hydroxy-2-{3-[(S)-hydroxy-(1-propyl-cyclobutyl)-methyl]-phenyl}-cyclopentylmethyl)-phenoxy]-acetic acid methyl ester;

[3-((1R,2S,3R,5R)-5-Chloro-3-hydroxy-2-{3-[(S)-hydroxy-(1-propyl-cyclobutyl)-methyl]-phenyl}-cyclopentylmethyl)-phenoxy]-acetic acid;

(Z)-7-[(1R,2S,3R)-3-Hydroxy-2-(1-hydroxy-indan-5-yl)-5-oxo-cyclopentyl]-hept-5-enoic acid methyl ester;

(Z)-7-[(1R,2S,3R)-3-Hydroxy-2-(1-hydroxy-indan-5-yl)-5-oxo-cyclopentyl]-hept-5-enoic acid;
(Z)-7-[(1R,2S,3R)-3-Hydroxy-5-oxo-2-(1-oxo-indan-5-yl)-cyclopentyl]-hept-5-enoic acid methyl ester;
(Z)-7-[(1R,2S,3R)-3-Hydroxy-5-oxo-2-(1-oxo-indan-5-yl)-cyclopentyl]-hept-5-enoic acid;
7-[(1R,2S,3R)-3-Hydroxy-2-(1-hydroxy-indan-5-yl)-5-oxo-cyclopentyl]-heptanoic acid methyl ester;
7-((1R,2S,3R)-3-Hydroxy-2-indan-5-yl-5-oxo-cyclopentyl)-heptanoic acid methyl ester;
7-[(1R,2S,3R)-3-Hydroxy-2-(1-hydroxy-indan-5-yl)-5-oxo-cyclopentyl]-heptanoic acid;
7-((1R,2S,3R)-3-Hydroxy-2-indan-5-yl-5-oxo cyclopentyl)-heptanoic acid;
(Z)-7-[(1R,2S,3R,5R)-5-Chloro-3-hydroxy-2-(1-hydroxy-indan-5-yl)-cyclopentyl]-hept-5-enoic acid methyl ester;
(Z)-7-[(1R,2S,3R,5R)-5-Chloro-3-hydroxy-2-(1-hydroxy-indan-5-yl)-cyclopentyl]-hept-5-enoic acid;
(Z)-7-[(1R,2S,3R,5R)-5-Chloro-3-hydroxy-2-(1-hydroxy-indan-5-yl)-cyclopentyl]-hept-5-enoic acid isopropyl ester;
7-[(1R,2S,3R,5R)-5-Chloro-3-hydroxy-2-(1-hydroxy-indan-5-yl)-cyclopentyl]-heptanoic acid methyl ester;
7-((1R,2S,3R,5R)-5-Chloro-3-hydroxy-2-indan-5-yl-cyclopentyl)-heptanoic acid methyl ester;
7-[(1R,2S,3R,5R)-5-Chloro-3-hydroxy-2-(1-hydroxy-indan-5-yl)-cyclopentyl]-heptanoic acid;
7-((1R,2S,3R,5R)-5-Chloro-3-hydroxy-2-indan-5-yl-cyclopentyl)-heptanoic acid;
7-[(1R,2S,3R)-5-Fluoro-3-hydroxy-2-(1-hydroxy-indan-5-yl)-cyclopentyl]-heptanoic acid methyl ester;
7-[(1R,2S,3R)-5-Fluoro-3-hydroxy-2-(1-hydroxy-indan-5-yl)-cyclopentyl]-heptanoic acid;
(Z)-7-[(1R,2S,3R)-5-Fluoro-3-hydroxy-2-(1-hydroxy-indan-5-yl)-cyclopentyl]-hept-5-enoic acid methyl ester; or
(Z)-7-[(1R,2S,3R)-5-Fluoro-3-hydroxy-2-(1-hydroxy-indan-5-yl)-cyclopentyl]-hept-5-enoic acid.

20. The compound of claim 14 of the formula

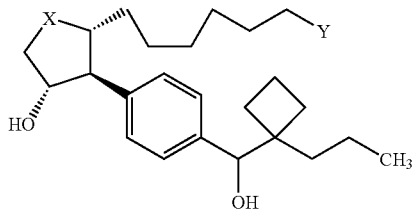

or a pharmaceutically acceptable salt, or a prodrug thereof.

21. The compound of claim 12 of the formula

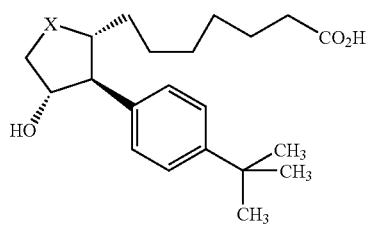

or a pharmaceutically acceptable salt, or a prodrug thereof.

22. The compound of claim 20 of the formula

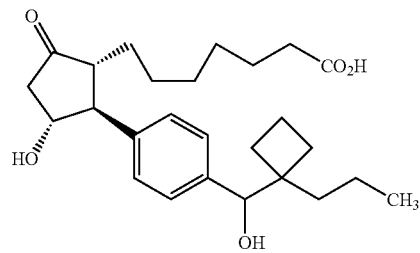

or a pharmaceutically acceptable salt, or a prodrug thereof.

23. The compound of claim 20 of the formula

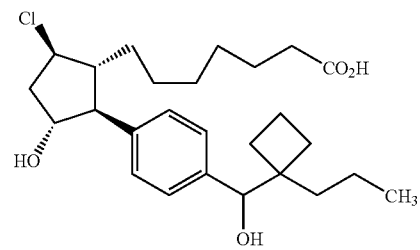

or a pharmaceutically acceptable salt, or a prodrug thereof.

24. The compound of claim 21 of the formula

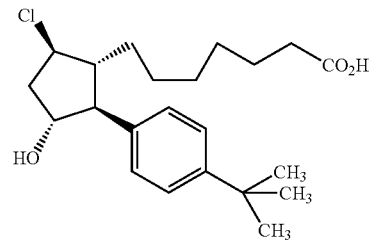

or a pharmaceutically acceptable salt, or a prodrug thereof.

25. The compound of claim 16 of the formula

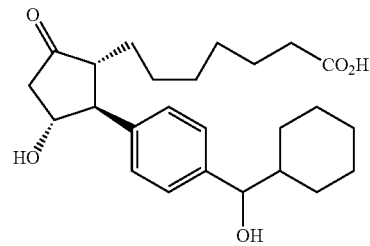

or a pharmaceutically acceptable salt, or a prodrug thereof.

26. The compound of claim 16 of the formula

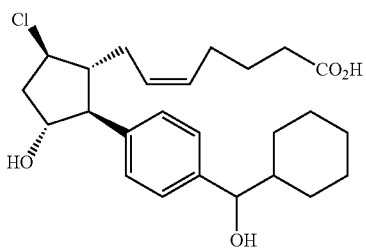

or a pharmaceutically acceptable salt, or a prodrug thereof.

27. The compound of claim 1 of the formula

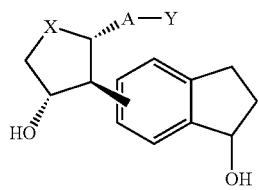

or a pharmaceutically acceptable salt or a prodrug thereof.

28. The compound of claim 27 wherein A is —(CH$_2$)$_6$—, cis —CH$_2$CH=CH—(CH$_2$)$_3$—, or —CH$_2$C≡C—(CH$_2$)$_3$—.

29. The compound of claim 28 of the formula

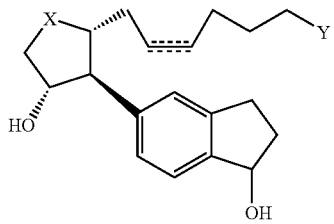

or a pharmaceutically acceptable salt or a prodrug thereof.

30. The compound of claim 29 of the formula

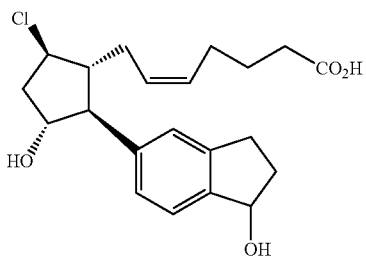

or a pharmaceutically acceptable salt or a prodrug thereof.

31. The compound of claim 5 wherein R is 1-hydroxy-alkyl having from 1 to 5 carbon atoms.

32. The compound of claim 31 of the formula

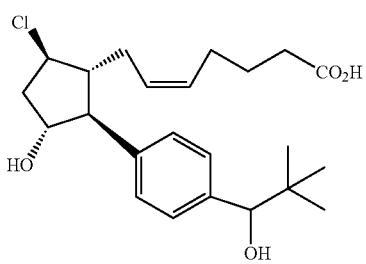

or a pharmaceutically acceptable salt or a prodrug thereof.

33. The compound of claim 1 wherein Y is selected from the group consisting of CO$_2$(R$^3$), CH$_2$OH, P(O)(OH)$_2$, SO$_2$N(R$^3$)$_2$, SO$_2$NHR$^3$, and tetrazolyl-R$^3$; wherein R$^3$ is independently H, C$_1$–C$_6$ alkyl, phenyl, or biphenyl.

34. The compound of claim 1 wherein R is 2-hydroxy-hydrocarbyl.

35. The compound of claim 34 of the formula

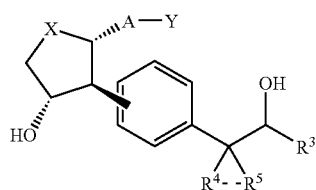

or a pharmaceutically acceptable salt or a prodrug thereof; wherein R$^3$, R$^4$, and R$^5$ are independently H or C$_{1-6}$ alkyl.

36. The compound of claim 35 wherein R$^4$ and R$^5$ are methyl.

37. The compound of claim 36 of the formula

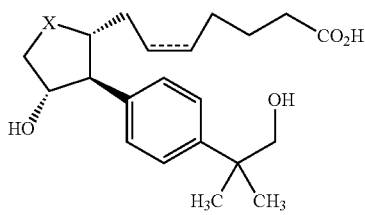

or a pharmaceutically acceptable salt or a prodrug thereof, wherein X is C=O or CHCl.

38. The compound of claim 1 wherein A is —(CH$_2$)$_m$—Ar—(CH$_2$)$_o$— wherein Ar is phenyl, the sum of m and o is from 1 to 4, and wherein one CH$_2$ may be substituted with S or O.

39. The compound of claim 38 wherein A is —CH$_2$—Ar—O—CH$_2$—.

40. The compound of claim 39 of the formula

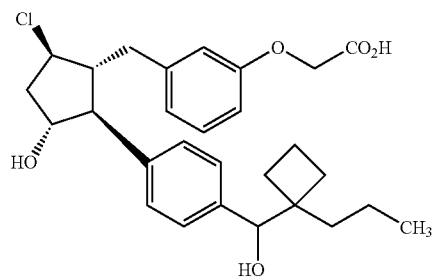

or a pharmaceutically acceptable salt or a prodrug thereof.

41. The compound of claim 29 of the formula

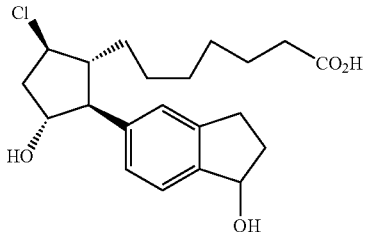

or a pharmaceutically acceptable salt or a prodrug thereof.

42. The compound of claim 31 of the formula

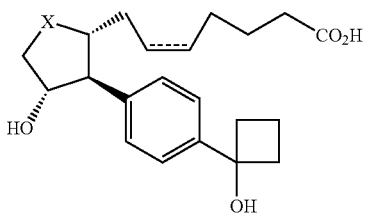

or a pharmaceutically acceptable salt or a prodrug thereof wherein X is C=O or CHCl.

43. The compound of claim 42 of the formula

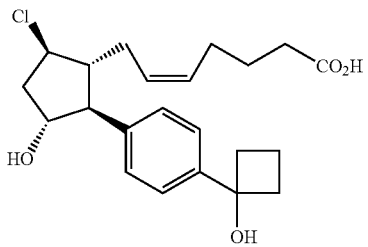

or a pharmaceutically acceptable salt or a prodrug thereof.

44. The compound of claim 37 of the formula

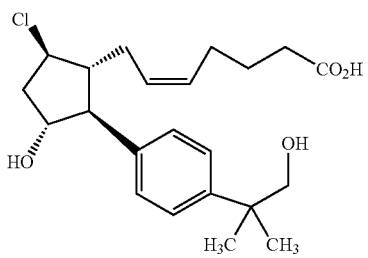

or a pharmaceutically acceptable salt or a prodrug thereof.

45. A method of treating glaucoma or reducing intraocular pressure comprising administering a compound of claim 1 to a mammal in need thereof.

46. A liquid composition having a compound of claim 1 wherein said liquid is ophthalmically acceptable.

* * * * *

UNITED STATES PATENT AND TRADEMARK OFFICE
CERTIFICATE OF CORRECTION

PATENT NO. : 7,091,231 B2  Page 1 of 1
APPLICATION NO. : 11/009298
DATED : August 15, 2006
INVENTOR(S) : Yariv Donde and Jeremiah H. Nguyen It is certified that error appears in the above-identified patent and that said Letters Patent is hereby corrected as shown below:

Column 137, claim 18 in the structure "R5" is replaced with "R6."

Signed and Sealed this

Twenty-first Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,091,231 B2
APPLICATION NO. : 11/009298
DATED : August 15, 2006
INVENTOR(S) : Donde et al.

It is certified that error appears in the above-identified patent and that said Letters Patent is hereby corrected as shown below:

In Column 8, line 31, delete "CH$_2$)$_m$" and insert -- (CH$_2$)$_m$ --, therefor.

In Column 8, line 40, delete "CH$_2$)$_2$" and insert -- (CH$_2$)$_2$ --, therefor.

In Column 12, line 50, delete "comprise." and insert -- comprise --, therefor.

In column 20, line 6, delete "R==H" and insert -- R=H --, therefor.

In column 23, line 14, delete "(ω-chain" and insert -- ω-chain --, therefor.

In column 23, line 15, delete "(ω-chain" and insert -- ω-chain --, therefor.

In column 23, line 23, delete "(ω-chain" and insert -- ω-chain --, therefor.

In column 25, line 50, delete "The" and insert -- the --, therefor.

In column 28, line 1, delete "prodecure" and insert -- procedure --, therefor.

In column 31, line 3, delete "(n-Bu)$_4$NCl" and insert -- (n-Bu)$_4$NCl --, therefor.

In column 32, line 15, delete "chloro" and insert -- Chloro --, therefor.

In column 32, line 16, delete "phenyl)-cyclopentyl}" and insert
-- phenyl}-cyclopentyl) --, therefor.

In column 36, line 14, delete "(n-Bu)$_4$NCl" and insert -- (n-Bu)$_4$NCl --, therefor, In column 36, line 45, delete "phenyl-3" and insert -- phenyl]-3 --, therefor.

In column 38, line 19, delete "teated" and insert -- treated --, therefor.

In column 39, line 7, delete "Z)" and insert -- (Z) --, therefor.

In column 39, line 52, delete "chromotagraphy" and insert -- chromatography --, therefor.

In column 40, line 63, delete "10 N" and insert -- 10N --, therefor.

In Column 40, line 66, delete "40°" and insert -- 4° --, therefor.

UNITED STATES PATENT AND TRADEMARK OFFICE
CERTIFICATE OF CORRECTION

PATENT NO.         : 7,091,231 B2
APPLICATION NO.    : 11/009298
DATED              : August 15, 2006
INVENTOR(S)        : Donde et al.

It is certified that error appears in the above-identified patent and that said Letters Patent is hereby corrected as shown below:

In column 134, line 36, in Claim 1, delete "cis–$CH_2CH=CH_r$–$(CH_2)_3$–" and insert -- cis–$CH_2CH=CH$–$(CH_2)_3$– --, therefor.

In Column 137, line 24, in Claim 18, delete "$R^5$" and insert -- $R^6$ --, therefor.

In column 137, line 46, in Claim 19, after "cyclopentyl" delete "]" and insert -- } --, therefor.

In column 137, line 53, in Claim 19, after "1R,2S,3R" delete "}" and insert -- ) --, therefor.

In column 138, line 1, in Claim 19. after "1R,2S,3R" delete "}" and insert -- ) --, therefor.

In column 138, line 7, in Claim 19, delete "[4 (2-hydroxy" and insert -- [4-(2-hydroxy --, therefor.

In column 138, lines 10-11, in Claim 19, delete "1-dimethylethyl)" and insert -- 1-dimethyl-ethyl) --, therefor.

In column 138, line 36, in Claim 19, after "methyl" delete ")" and insert -- ] --, therefor.

In column 139, line 16, in Claim 19, delete "4-hydroxy" and insert -- 4-[hydroxy --, therefor.

In column 139, line 43, in Claim 19, delete "1-dimethylethyl)" and insert -- 1-dimethyl-ethyl) --, therefor.

In column 140, lines 36-37, in Claim 19, delete "but-2-enyloxy)" and insert -- but-2-ynyloxy) --, therefor.

In column 141, lines 13-14, in Claim 19, delete "oxo cyclopentyl)" and insert -- oxo-cyclopentyl) --, therefor.

UNITED STATES PATENT AND TRADEMARK OFFICE
CERTIFICATE OF CORRECTION

PATENT NO.        : 7,091,231 B2
APPLICATION NO.   : 11/009298
DATED             : August 15, 2006
INVENTOR(S)       : Donde et al.

It is certified that error appears in the above-identified patent and that said Letters Patent is hereby corrected as shown below:

In column 143, line 26, in Claim 28, delete "cis–$CH_2CH\equiv CH-(CH_2)_3-$" and insert -- cis–$CH_2CH=CH-(CH_2)_3-$ --, therefor.

Signed and Sealed this

Thirty-first Day of July, 2007

JON W. DUDAS
*Director of the United States Patent and Trademark Office*